(12) United States Patent
Dana et al.

(10) Patent No.: US 10,105,441 B2
(45) Date of Patent: *Oct. 23, 2018

(54) METHOD FOR INHIBITING OR REDUCING DRY EYE DISEASE BY IL-1RA

(75) Inventors: Reza Dana, Newton, MA (US); Mohammad Dastjerdi, Prairie Village, KS (US)

(73) Assignee: The Schepens Eye Research Institute, Inc., Boston, MA (US)

(*) Notice: Subject to any disclaimer, the term of this patent is extended or adjusted under 35 U.S.C. 154(b) by 684 days.

This patent is subject to a terminal disclaimer.

(21) Appl. No.: 12/298,380

(22) PCT Filed: Aug. 15, 2008

(86) PCT No.: PCT/US2008/009776
§ 371 (c)(1),
(2), (4) Date: Apr. 28, 2010

(87) PCT Pub. No.: WO2009/025763
PCT Pub. Date: Feb. 26, 2009

(65) Prior Publication Data
US 2010/0203103 A1    Aug. 12, 2010

Related U.S. Application Data

(60) Provisional application No. 60/965,135, filed on Aug. 16, 2007, provisional application No. 61/130,687, filed on Jun. 2, 2008.

(51) Int. Cl.
| | | |
|---|---|---|
| *A61K 38/00* | (2006.01) |
| *A61K 49/00* | (2006.01) |
| *A61K 38/19* | (2006.01) |
| *A61K 38/20* | (2006.01) |
| *A61K 38/21* | (2006.01) |
| *A61K 39/395* | (2006.01) |
| *A61K 9/00* | (2006.01) |
| *A61K 31/7105* | (2006.01) |
| *A61K 38/06* | (2006.01) |
| *A61K 38/13* | (2006.01) |
| *A61K 38/18* | (2006.01) |
| *A61K 45/06* | (2006.01) |
| *A61K 36/82* | (2006.01) |
| *A61K 36/87* | (2006.01) |
| *A61K 36/16* | (2006.01) |
| *A61K 36/258* | (2006.01) |
| *A61K 36/45* | (2006.01) |
| *A61K 36/537* | (2006.01) |
| *A61K 31/7088* | (2006.01) |
| *A61K 38/17* | (2006.01) |

(52) U.S. Cl.
CPC ........ *A61K 39/3955* (2013.01); *A61K 9/0051* (2013.01); *A61K 31/7088* (2013.01); *A61K 31/7105* (2013.01); *A61K 36/16* (2013.01); *A61K 36/258* (2013.01); *A61K 36/45* (2013.01); *A61K 36/537* (2013.01); *A61K 36/82* (2013.01); *A61K 36/87* (2013.01); *A61K 38/063* (2013.01); *A61K 38/13* (2013.01); *A61K 38/1709* (2013.01); *A61K 38/1816* (2013.01); *A61K 38/2006* (2013.01); *A61K 38/21* (2013.01); *A61K 45/06* (2013.01)

(58) Field of Classification Search
CPC .. A61K 2300/00; A61K 38/13; A61K 9/0048; A61K 31/65; A61K 38/2006; A61K 8/64; A61K 47/42; C07K 14/54; C07K 14/545; C07K 16/244; C07K 16/245; A61L 2300/252; A61L 2300/41; A61L 2300/426; A61L 27/54; A61L 29/16; A61L 31/16

See application file for complete search history.

(56) References Cited

U.S. PATENT DOCUMENTS

| | | | |
|---|---|---|---|
| 5,075,222 A | 12/1991 | Hannum et al. | 435/69.1 |
| 5,340,572 A | 8/1994 | Patel et al. | 424/78.04 |
| 5,453,490 A | 9/1995 | Hageman et al. | 530/350 |
| 5,770,401 A | 6/1998 | Mullarkey | 435/69.2 |
| 5,895,812 A | 4/1999 | Laurie et al. | |
| 6,096,728 A | 8/2000 | Collins et al. | 514/62 |
| 6,159,460 A | 12/2000 | Thompson et al. | 424/85.1 |
| 6,416,753 B1 | 6/2002 | Yuan et al. | 424/85.2 |
| 6,471,961 B1 | 10/2002 | Tobinick | 424/134.1 |
| 6,599,873 B1 | 5/2003 | Dawkins et al. | 345/862 |
| 6,623,736 B2 | 9/2003 | Tobinick | 424/134.1 |

(Continued)

FOREIGN PATENT DOCUMENTS

| | | |
|---|---|---|
| CA | 2648223 | 10/2007 |
| EP | 0343684 B1 | 11/1989 |

(Continued)

OTHER PUBLICATIONS

Yamada et al. "Interleukin 1 Receptor Antagonist Suppresses Allosensitization in Corneal Transplantation." *Arch. Ophthalmol.* 116(1998):1351-1357.

(Continued)

*Primary Examiner* — Chang-Yu Wang
(74) *Attorney, Agent, or Firm* — Mintz, Levin, Cohn, Ferris, Glovsky and Popeo, P.C.; Ingrid A. Beattie

(57) ABSTRACT

The present invention comprises a composition with means to inhibit the function of the inflammatory cytokine IL-1 and methods for using this composition to treat inflammatory disease of ocular and adnexal tissues by topical administration. The present invention also discloses devices for delivering this composition to target tissues.

12 Claims, 6 Drawing Sheets
Specification includes a Sequence Listing.

(56) References Cited

U.S. PATENT DOCUMENTS

| | | | |
|---|---|---|---|
| 6,858,409 B1 | 2/2005 | Thompson et al. | 435/69.7 |
| 6,927,044 B2 | 8/2005 | Stahl et al. | 435/69.7 |
| 6,974,682 B1 | 12/2005 | Bednarik | 435/69.1 |
| 7,087,224 B2 | 8/2006 | Kay et al. | 424/85.1 |
| 7,988,294 B2 | 8/2011 | Korb et al. | |
| 8,252,945 B2 * | 8/2012 | Seike et al. | 548/361.1 |
| 2001/0041792 A1 | 11/2001 | Donda et al. | 530/399 |
| 2001/0042304 A1 | 11/2001 | Sato | 29/831 |
| 2003/0007971 A1 | 1/2003 | Hara et al. | 424/145.1 |
| 2003/0026806 A1 | 2/2003 | Witte et al. | 424/145.1 |
| 2004/0022718 A1 | 2/2004 | Stupp et al. | 423/445 |
| 2004/0044001 A1 | 3/2004 | Bendele et al. | 514/251 |
| 2004/0208874 A1 | 10/2004 | Khare | 424/145.1 |
| 2005/0023872 A1 | 2/2005 | Hetzel et al. | 297/256.16 |
| 2005/0033694 A1 | 2/2005 | Perrin | 705/44 |
| 2005/0059589 A1 | 3/2005 | Mullarkey | 514/12 |
| 2005/0105830 A1 | 5/2005 | Chung et al. | 382/300 |
| 2005/0143333 A1 | 6/2005 | Richards et al. | 514/44 |
| 2006/0088600 A1 | 4/2006 | Thornion et al. | 424/523 |
| 2006/0094663 A1 | 5/2006 | Chemtob et al. | 514/16 |
| 2006/0275801 A1 * | 12/2006 | Henkin | 435/6 |
| 2007/0098684 A9 | 5/2007 | Raibekas et al. | 424/85.2 |
| 2007/0248597 A1 | 10/2007 | Henley, III et al. | 424/133.1 |
| 2007/0280924 A1 | 12/2007 | Daniels et al. | |
| 2008/0132475 A1 | 6/2008 | Connor et al. | |
| 2008/0286378 A1 | 11/2008 | Behrens et al. | |
| 2008/0312194 A1 | 12/2008 | Ousler, III et al. | |
| 2009/0012123 A1 * | 1/2009 | Seike et al. | 514/322 |
| 2009/0136445 A1 * | 5/2009 | Wong et al. | 424/85.2 |
| 2009/0234005 A1 * | 9/2009 | Ishida et al. | 514/559 |
| 2010/0047204 A1 | 2/2010 | Yoo et al. | |
| 2010/0203103 A1 * | 8/2010 | Dana et al. | 424/429 |
| 2011/0104236 A1 * | 5/2011 | Dana et al. | 424/429 |
| 2012/0014970 A1 * | 1/2012 | Dana et al. | 424/158.1 |

FOREIGN PATENT DOCUMENTS

| | | |
|---|---|---|
| EP | 0541920 B1 | 5/1993 |
| JP | 2002154985 A | 5/2002 |
| JP | 2002514194 A | 5/2002 |
| JP | 2002514602 A | 5/2002 |
| JP | 2003523925 A | 8/2003 |
| JP | 2005524393 A | 8/2005 |
| JP | 2006517191 A | 7/2006 |
| JP | 2009505500 A | 2/2009 |
| WO | WO 98/22130 | 5/1998 |
| WO | WO-9958131 A1 | 11/1999 |
| WO | WO-0007601 A1 | 2/2000 |
| WO | WO-03070918 A2 | 8/2003 |
| WO | WO-2004060911 A2 | 7/2004 |
| WO | WO-2005097195 A2 | 10/2005 |
| WO | WO2007056812 * | 5/2007 |
| WO | WO-2007120828 A1 | 10/2007 |
| WO | WO 2007/145618 A1 | 12/2007 |

OTHER PUBLICATIONS

Accession No. AF_057168.1, Apr. 1998.
Accession No. DB00026, Jun. 2005.
Accession No. M55646.1, Jan. 1995.
Accession No. NM_000575.3, Feb. 2009.
Accession No. NM_000576.2, Feb. 2009.
Accession No. NM_000577.3, Mar. 2009.
Accession No. NM_000877.2, Mar. 2009.
Accession No. NM_001025242.1, Feb. 2009.
Accession No. NM_001025243.1, Feb. 2009.
Accession No. NM_001569.3, Feb. 2009.
Accession No. NM_002182.2, Dec. 2008.
Accession No. NM_004633.3, Feb. 2009.
Accession No. NM_134470.2, Dec. 2008.
Accession No. NM_173343.1, Feb. 2009.
Accession No. NM_173841.1, Mar. 2009.
Accession No. NM_173842.1, Mar. 2009.
Accession No. NM_173843.1, Mar. 2009.
A.D.A.M., Glaucoma Diagnosis; created Mar. 3, 2007 [online], [retrieved on Feb. 3, 2009] retrieved from the internet URL:http://www.umm.edu/cgi-bin/printpage.cgi, pp. 2-3 section entitled "Tonometry and Pressure Tests", 5 pages.
Antin et al., "Recombinant human interleukin-1 receptor antagonist in the treatment of steroid-resistant graft-versus-host disease", Blood, 84:1342-1348 (1994).
Arend, W.P., "Interleukin-I Receptor Antagonist", Adv. Immunol., 54:167-223 (1993).
Barton et al., "Inflammatory cytokines in the tears of patients with ocular rosacea", Opthalmol, 104:1868-1874 (1997).
Benoist et al., "In vivo sequence requirements of the sv40 early promoter region", Nature, 290:304-310 (1981).
Bresnihan et al., "Interleukin-1 receptor antagonist", Rheum. Dis. Clin. North Am,., 24(3):615-628 (1998).
Brignole et al., "Flow cytobetric analysis of inflammatory markers in conjunctival epithelial cells of patients with dry eyes", Invest. Ophtalmol. Vis. Sci., 41(6):1356-1362 (2000).
Brinster et al., "Regulation of metallothionein-thymidine kinase fusion plasmids injected into mouse eggs", Nature, 296:39-42 (1982).
Bron et al., "The Contribution of Meibomian Disease to Dry Eye", Ocul. Surf., 2:149-165 (2004).
Caron et al., "Chondroprotective effect of intraarticular injections of interleukin-1 receptor antagonist in experimental osteoarthritis", Arthritis Rheum., 39:1535-1544 (1996).
Dana et al., "Topical interleukin 1 receptor antagonist promotes corneal transplant survival", Transplantation, 63(10):1501-1507 (1997).
Dana et al., "Topical Modulation of interleukin-1 activity in corneal neovascularization", Cornea, 17(4):403-409 (1998).
Dana, R., "Comparison of topical interleukin-1 vs tumor necrosis factor-alpha blockade with corticosteroid therapy on murine corneal inflammation, neovascularization, and transplant survival (an American Ophthalmological society thesis)", Trans. Am. Ophthalmol. Soc., 105:1-14 (2007).
Dayer et al., "Anti-interleukin-1 therapy in rheumatic diseases", Curr. Opin. Rheumatol., 13:170-176 (2001).
Dekaris et al., "Effect of topical interleukin-1 receptor antagonist (IL-1ra) on corneal allograft survival in presensitized hosts", Curr. Eye Res., 19(5):456-459 (1999).
Dinarello, C.A., "Biologic basis for interleukin", Blood, 87(6):2095-2147 (1996).
Dinarello, C.A., "The role of the interleukin-1-receptor antagonist in blocking inflammation mediated by interleukin-1", N. Engl. J. Med., 343(10):732-734 (2000).
Edwards, C.K., "Combination cytokine therapy in rheumatoid arthritis: the next generation", J. Clin. Rheumatol., 7:S17-S24 (2001).
Fabre et al., "Binding sites for human interleukin 1α, gamma interferon and tumor necrosis factor on cultures fibroblasts of normal cornea and keratoconus", Curr. Eye. Res., 10:585-592 (1991).
Fini et al., "Express of Collagenolytic / Gelatinolytic Metalloproteinases by Normal Cornea", Invest. Opthalmol. Vis. Sci., 31:1779-1788 (1990).
Fisher et al., "Recombinant human interleukin 1 receptor antagonist in the treatment of patients with sepsis syndrome: results from a randomized, double-blind, placebo-controlled trial", JAMA., 271(23):1836-1843 (1994).
Foulks et al., "Meibomian gland dysfunction: A clinical scheme for description, diagnosis, classification, and grading", Ocul. Surf., 1(3):107-126 (2003).
Fu, Y.A., "Ocular manifestation of polychlorinated biphenyls intoxication", Am. J. Ind. Med., 5:127-132 (1984).
Fukushima et al., "Ag-specific recognition, activation, and effector function of T cells in the conjunctiva with experimental immune-mediated blepharoconjunctivitis", Invest. Opthalmol. Vis. Sci., 44:4366-4374 (2003).
Gabay et al., "Mouse IL-1 receptor antagonist isoforms: complementary DNA cloning and protein expression of intracellular isoform

(56) References Cited

OTHER PUBLICATIONS and tissue distribution of secreted and intracellular IL-1 receptor antagonist in vivo", *J. Immunol.*, 159:5905-5913 (1997).
Glynn et al., "Comparison of alternative regression models for paired binary data", *Stat. Med.*, 13(10):1023-1036 (1994).
Goto et al., "Impaired functional visual acuity of dry eye patients", *Am. J. Opthalmol.*, 133:181-186 (2002).
Hynninen et al., "Interleukin 1 receptor antagonist and E-selectin concentrations: A comparison in patients with severe acute pancreatitis and severe sepsis", *J. Crit Care.*, 14(2):63-68 (1999).
Jiang et al., "A multicenter, double-blind, dose-ranging, randomized, placebo-controlled study of recombinant human interleukin-1 receptor antagonist in patients with rheumatoid arthritis", *Arthritis Rheum.*, 43(5):1001-1009 (2000).
Jones et al., "Sjögren's syndrome: Cytokine and Epstein-Barr viral gene expression within the Conjunctival Epithelium", *Invest. Ophtalmol. Vis. Sci.*, 35(9):3493-3503 (1994).
Keane-Meyers et al., "Prevention of allergic eye disease by treatment with IL-1 receptor antagonist", *Invest. Opthalmol. Vis. Sci.*, 40(12):3041-3046 (1999).
Kocak-Altintas et al., "Impression cytology and ocular characteristics in ocular rosacea", *Eur. J. Opthalmol.*, 13:351-359 (2003).
Larsen et al., "Interleukin-1-receptor antagonist in type 2 diabetes mullitus", *N. Engl. J. Med.*, 356:1517-1526 (2007).
Marsh et al., "Tropical nonpreserved methylprednisolone therapy for keratocojunctivitis sicca in sjögren syndrome", *Opthalmol.*, 106:811-816 (1999).
Martinsen et al., "Alginate as immobilization material: I. Correlation between chemical and physical properties of alginate gel beads", *Biotech. Bioeng.*, 33:79-89 (1989).
McCulley et al., "Changing concepts in the diagnosis and management of blephartis", *Cornea*, 19:650-658 (2000).
McCulley et al., "Meibomian Keratoconjunctivitis", *A. J. Opthalmol.*, 84:788-793 (1977).
McDevitt et al., "Interleukin-1 genetic association with periodontitis in clinical practice", *J. Periodontol.* 71:156-163 (2000).
Miljanovic et al., "Impact of dry eye syndrome on vision-related quality of life", *Am. J Opthalmol.*, 143:409-415 (2007).
O'Neill et al., "Signal transduction pathways activated by the IL-1 receptor family: ancient signaling machinery in mammals, insects, and plants", J. Leukocyte Biol., 63:650-657 (1998).
Okusawa et al., "Interleukin 1 induces a shock-like state in rabbits", *J. Clin. Invest.*, 81:1162-1172 (1988).
Pflugfelder et al., "Altered cytokine balance in the tear fluid and conjunctiva of paitients with sjögren's syndrome keratoconjunctivitis sicca", Curr. Eye Res., 19:201-211 (1999).
Pflugfelder et al., "Conjunctival cytologic features of primary sjögren's syndrome", *Ophthalmol.*, 97(8):985-991 (1990).
Pisella et al., "Flow Cytometric Analysis of Conjunctival Epithelium in Ocular Rosacea and Keratoconjunctivitis Sicca", *Opthalmol.*, 107:1841-1849 (2000).
Reiff, A., "The use of anakinra in juvenile arthritis", *Curr. Rheumatol. Rep.*, 7:434-440 (2005).
Rosenbaum et al., "Detection of mRNA for the Cytokines, Interleukin-1α and interleukin-8, in corneas from patients with pseudophakic bullous keratopathy", *Invest. Opthalmol. Vis. Sci.*, 36:2151-2155 (1995).
Rosner et al., "Incorporation of clustering effects for the Wilcoxon rank sum test: A Large-Sample Approach", *Biometrics*, 59(4):1089-1098 (2003).
Sall et al., "Two multicenter, randomized studies of Efficacy and safety of cyclosporine ophthalmic emulsion in moderate to severe dry eye disease", *Ophthalmol.*, 107:631-639 (2000).

Schiffman et al., "Reliability and Validity of the Ocular Surface Disease index", *Arch. Ophthalmol.*, 118:615-621 (2000).
Shimazaki et al., "Meibomian gland dysfunction in patients with sjögren syndrome", *Opthalmol.*, 105:1485-1488 (1998).
Smith et al., "Doxycycline—a role in ocular surface repair", *Br. J. Ophthalmol.*, 88:619-625 (2004).
Solomon et al., "Doxycycline inhibition of interleukin-1 in the corneal epithelium", *Invest. Opthalmol. Vis. Sci.*, 41:2544-2557 (2000).
Solomon et al., "Pro- and Anti-imflammatory forms of interleukin-1 in the tear fluid and conjunctiva of patients with dry-eye disease", *Invent. Opthalmol. Vis. Sci.*, 42:2283-2292 (2001).
Stevenson et al., "Efficacy and safety of cyclosporine a ophthalmic emulsion in the treatment of moderate-to-severe dry eye disease", *Opthalmol.*, 107(5):967-974 (2000).
Sullivan et al., "Robustness and power of analysis of covariance applied to ordinal scaled data as arising in randomized controlled trials", *Stat. Med.*, 22(8):1317-1334 (2003).
Teoh et al., "Tailoring biological treatment: anakinra treatment of posterior uveitis associated with the CINCA syndrome", *Br. J. Opthalmol.*, 91:263-264 (2007).
Wagner et al., "Nucleotide sequence of the thymidine kinase gene of herpes simplex virus type 1", *Proc. Natl. Acad. Sci. U.S.A.*, 78(3):1441-1445 (1980).
Yamada et al., "Interleukin-1 receptor antagonist therapy and induction of anterior chamber-associated immune deviation-type tolerance after corneal transplantation", *Invest. Opthalmol. Vis. Sci.*, 41:4203-4208 (2000).
Yamada et al., "Local suppression of IL-1 by receptor antagonist in the rat model of corneal alkali injury", *Exp. Eye Res.*, 76:161-167 (2003).
Yamamoto et al., "Identification of a functional promoter in the long terminal repeat of rous sarcoma virus", *Cell*, 22:787-797 (1980).
Yamasaki et al., "Interleukin-1 as a pathogenetic mediator of ischemic brain damage in rats", *Stroke*, 26:676-681 (1995).
International Search Report for PCT/US08/09776, dated Feb. 26, 2009.
Auw-Haedrich et al. "Chronic Blepharitis. Phatogenesis, Clinical Features, and Therapy." *Der Ophthalmologe.* 104.9(Sep. 2007):2007-2009.
"Eyelid Disorders." *The Merck Manual of Diagnosis and Therapy.* 2006:885-886.
Macsai. "The Role of Omega-3 Dietary Supplementation in Blephartis and Meibomian Gland Dysfunction (an AOS Thesis)." *Transactions of the American Ophthalmological Society.* 106(2008):336-356.
Dana et al., "Randomized Phase II Trial of Safety and Efficacy of Topical Interleukin-1 Receptor Antagonist (IL-1Ra) for Treatment of Melbomian Gland Dysfunction (MGD)-Associated Occular Surface Disease." (2012).
Carter S., Eyelid disorders: diagnosis and management. Am Fam Physician. Jun. 1998:57(11):2695-702.
DEWS. The definition and classification of dry eye disease: report of the Definition and Classification Subcommittee of the International Dry Eye WorkShop (2007). Ocul Surf. Apr. 2007;5(2):75-92.
Heiting, G. Ocular Hypertension (High Eye Pressure). All About Vision. <http://www.allaboutvision.com/conditions/hypertension.htm>.
Kabat, G., Chapter 29: Uveitis. pp. 587-599. In: Clinical Ocular Pharmacology, 5th Ed., 2008.
Rashid et al., Topical omega-3 and omega-6 fatty acids for treatment of dry eye. Arch Ophthalmol. Feb. 2008;126(2):219-25.

\* cited by examiner

FIGURE 1

Ocular Surface Disease Index (OSDI)
Circle the number in the box that best represents each answer.
Have you experienced any of the following during the last week:

|  | All of the time | Most of the time | Half of the time | Some of the time | None of the time |
|---|---|---|---|---|---|
| 1. Eyes that are sensitive to light? | 4 | 3 | 2 | 1 | 0 |
| 2. Eyes that feel gritty? | 4 | 3 | 2 | 1 | 0 |
| 3. Painful or sore eyes? | 4 | 3 | 2 | 1 | 0 |
| 4. Blurred vision? | 4 | 3 | 2 | 1 | 0 |
| 5. Poor vision? | 4 | 3 | 2 | 1 | 0 |

Have problems with your eyes limited you in performing any of the following during the last week:

|  | All of the time | Most of the time | Half of the time | Some of the time | None of the time |  |
|---|---|---|---|---|---|---|
| 6. Reading? | 4 | 3 | 2 | 1 | 0 | N/A |
| 7. Driving at night? | 4 | 3 | 2 | 1 | 0 | N/A |
| 8. Working with a computer or bank machine (ATM)? | 4 | 3 | 2 | 1 | 0 | N/A |
| 9. Watching TV? | 4 | 3 | 2 | 1 | 0 | N/A |

Have your eyes felt uncomfortable in any of the following situations during the last week:

|  | All of the time | Most of the time | Half of the time | Some of the time | None of the time |  |
|---|---|---|---|---|---|---|
| 10. Windy conditions? | 4 | 3 | 2 | 1 | 0 | N/A |
| 11. Places or areas with low humidity (very dry)? | 4 | 3 | 2 | 1 | 0 | N/A |
| 12. Areas that are air conditioned? | 4 | 3 | 2 | 1 | 0 | N/A |

Total score for answers 1 to 12 _____

Total number of questions answered _____
(Do not include questions answered N/A)

OSDI= (sum of scores)/(# of questions answered) _____

FIGURE 2

| PANEL | | Grade | Criteria |
|---|---|---|---|
| A | | 0 | Equal to or less than panel A |
| B | | I | Equal to or less than panel B, greater than A |
| C | | II | Equal to or less than panel C, greater than B |
| D | | III | Equal to or less than panel D, greater than C |
| E | | IV | Equal to or less than panel E, greater than D |
| >E | | V | Greater than panel E |

FIGURE 5

Definition of Meibomian Gland Dysfunction (Posterior Blepharitis)

Meibomian Gland Evaluation:
In the center of the lower lid, 10 adjacent central glands will be located on both sides and the glands will be expressed by applying a firm digital pressure at the base of the glands. The number of glands expressed for each eye will be documented.

Locate 10 central glands on the lower lid and circle the number of glands expressed for each eye.
1  2  3  4  5  6  7  8  9  10

The quality of secretion will be described as follows:
- Clear excreta or clear with small particles    grade 0
- Opaque excreta with normal viscosity    grade 1
- Opaque excreta with increased viscosity    grade 2
- Secretions retain shape after expression    grade 3

Lid and Lid Margin Evaluation: Lid margin vascular injection (erythema) is defined as a red discoloration, compared to the surrounding eyelid skin and will be graded as follows:

| | | |
|---|---|---|
| None | (0): | none |
| Mild | (1): | redness localized to a small region of the lid margin(s) or skin |
| Moderate | (2): | redness of most of the lid margin(s) |
| Severe | (3): | redness of most or all the lid margin(s) and skin |
| Very Severe | (4): | marked diffuse redness of both lid margins and skin |

Presence or absence of tarsal telangiectasis will also be noted. Lid telangiectasia is defined as the presence of at least two blood vessels along the eyelid margin.

Conjunctiva (Palpebral and Bulbar): Bulbar conjunctival hyperemia will be graded as follows:

| | | |
|---|---|---|
| None | (0): | none |
| Mild | (1): | slight localized injection |
| Moderate | (2): | pink color, confined to palpebral or bulbar conjunctiva |
| Severe | (3): | red color of the palpebral and/or bulbar conjunctiva |
| Very Severe | (4): | marked dark redness of the palpebral and/or bulbar conjunctiva |

Presence or absence of tarsal papillary hypertrophy will also be noted.

Posterior blepharitis will be diagnosed when in the presence of symptoms (itching, tearing, burning, and episodes of blurred vision), quality of meibomian gland secretion is $\geq$ grade 1 in at least one eye, and at least one of the following is present:
- Lid margin erythema
- Lid margin telangiectasia
- Conjunctival hyperemia or papillary reaction

FIGURE 6

Flow Diagram of Clinical Tests

To avoid the influence of one procedure on another, clinical tests, dry eye tests, and ocular surface evaluation will be done in the following sequence:

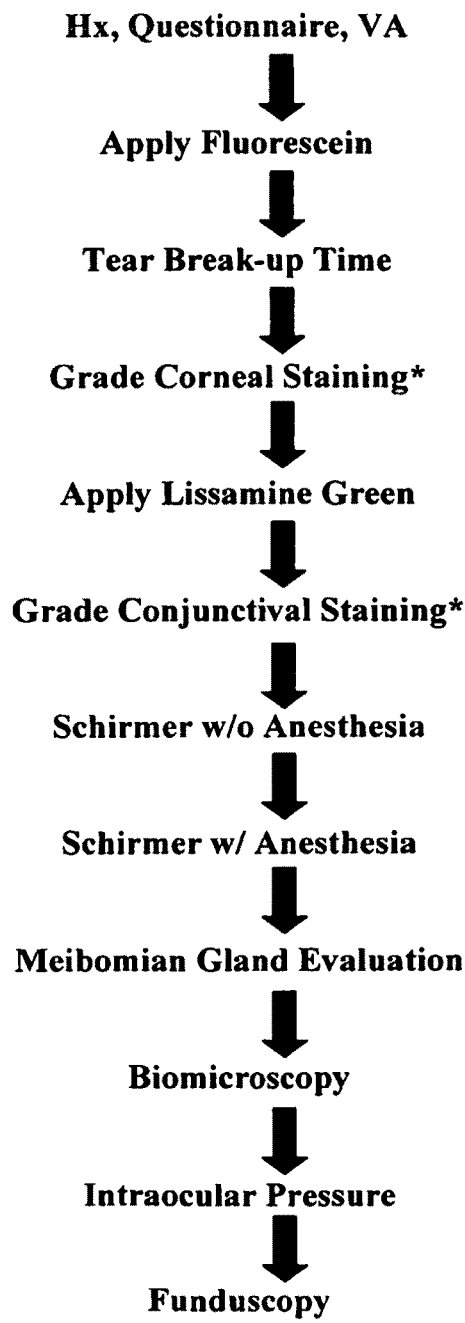

Hx, Questionnaire, VA
↓
Apply Fluorescein
↓
Tear Break-up Time
↓
Grade Corneal Staining*
↓
Apply Lissamine Green
↓
Grade Conjunctival Staining*
↓
Schirmer w/o Anesthesia
↓
Schirmer w/ Anesthesia
↓
Meibomian Gland Evaluation
↓
Biomicroscopy
↓
Intraocular Pressure
↓
Funduscopy \* Evaluate staining 2 minutes after dye instillation.

SEQUENCE LISTING

<160> NUMBER OF SEQ ID NOS: 44

<210> SEQ ID NO 1
<211> LENGTH: 2943
<212> TYPE: DNA
<213> ORGANISM: Homo sapiens

<400> SEQUENCE: 1

```
accaggcaac accattgaag gctcatatgt aaaaatccat gccttccttt ctcccaatct      60
ccattcccaa acttagccac tggcttctgg ctgaggcctt acgcataccT cccggggctt     120
gcacacacct tcttctacag aagacacacc ttgggcatat cctacagaag accaggcttc     180
tctctggtcc ttggtagagg gctactttac tgtaacaggg ccagggtgga gagttctctc     240
ctgaagctcc atcccctcta taggaaatgt gttgacaata ttcagaagag taagaggatc     300
aagacttctt tgtgctcaaa taccactgtt ctcttctcta ccctgcccta accaggagct     360 tgtcaccccca aactctgagg tgatttatgc cttaatcaag caaacttccc tcttcagaaa    420
agatggctca ttttccctca aaagttgcca ggagctgcca agtattctgc caattcaccc     480
tggagcacaa tcaacaaatt cagccagaac acaactacag ctactattag aactattatt     540
attaataaat tcctctccaa atctagcccc ttgacttcgg atttcacgat ttctcccttc     600
ctcctagaaa cttgataagt ttcccgcgct tccctttttc taagactaca tgtttgtcat     660
cttataaagc aaagggtga ataaatgaac caaatcaata acttctggaa tatctgcaaa      720
caacaataat atcagctatg ccatctttca ctattttagc cagtatcgag ttgaatgaac     780
atagaaaaat acaaaactga attcttccct gtaaattccc cgttttgacg acgcacttgt     840
agccacgtag ccacgcctac ttaagacaat tacaaaaggc gaagaagact gactcaggct     900
taagctgcca gccagagagg gagtcatttc attggcgttt gagtcagcaa agaagtcaag     960
atggccaaag ttccagacat gtttgaagac ctgaagaact gttacagtga aaatgaagaa    1020
gacagttcct ccattgatca tctgtctctg aatcagaaat ccttctatca tgtaagctat    1080
ggcccactcc atgaaggctg catggatcaa tctgtgtctc tgagtatctc tgaaacctct    1140
aaaacatcca agcttacctt caaggagagc atggtggtag tagcaaccaa cgggaaggtt    1200
ctgaagaaga gacggttgag tttaagccaa tccatcactg atgatgacct ggaggccatc    1260
gccaatgact cagaggaaga aatcatcaag cctaggtcag caccttttag cttcctgagc    1320
aatgtgaaat acaactttat gaggatcatc aaatacgaat tcatcctgaa tgacgccctc    1380
aatcaaagta taattcgagc caatgatcag tacctcacgg ctgctgcatt acataatctg    1440
gatgaagcag tgaaatttga catgggtgct tataagtcat caaaggatga tgctaaaatt    1500
accgtgattc taagaatctc aaaaactcaa ttgtatgtga ctgcccaaga tgaagaccaa    1560
ccagtgctgc tgaaggagat gcctgagata cccaaaacca tcacaggtag tgagaccaac    1620
ctcctcttct tctgggaaac tcacggcact aagaactatt tcacatcagt tgcccatcca    1680
aacttgttta ttgccacaaa gcaagactac tgggtgtgct tggcaggggg gccaccctct    1740
```

```
atcactgact tcagatact ggaaaaccag gcgtaggtct ggagtctcac ttgtctcact    1800
tgtgcagtgt tgacagttca tatgtaccat gtacatgaag aagctaaatc ctttactgtt    1860
agtcatttgc tgagcatgta ctgagccttg taattctaaa tgaatgttta cactctttgt    1920
aagagtggaa ccaacactaa catataatgt tgttatttaa agaacaccct atattttgca    1980
tagtaccaat cattttaatt attattcttc ataacaattt taggaggacc agagctactg    2040
actatggcta ccaaaaagac tctacccata ttacagatgg gcaaattaag cataagaaa     2100
actaagaaat atgcacaata gcagttgaaa caagaagcca cagacctagg atttcatgat    2160
ttcatttcaa ctgtttgcct tctactttta agttgctgat gaactcttaa tcaaatagca    2220
taagtttctg ggacctcagt tttatcattt tcaaaatgga gggaataata cctaagcctt    2280
cctgccgcaa cagttttta tgctaatcag ggaggtcatt ttggtaaaat acttcttgaa     2340
gccgagcctc aagatgaagg caaagcacga atgttatttt ttaattatt atttatatat     2400
gtatttataa atatatttaa gataattata atatactata tttatgggaa cccttcatc    2460
ctctgagtgt gaccaggcat cctccacaat agcagacagt gttttctggg ataagtaagt    2520
ttgatttcat taatacaggg cattttggtc caagttgtgc ttatcccata gccaggaaac    2580
tctgcattct agtacttggg agacctgtaa tcatataata aatgtacatt aattaccttg    2640
agccagtaat tggtccgatc tttgactctt ttgccattaa acttacctgg gcattcttgt    2700
ttcaattcca cctgcaatca agtcctacaa gctaaaatta gatgaactca actttgacaa    2760
ccatgagacc actgttatca aactttctt tctggaatg taatcaatgt ttcttctagg      2820
ttctaaaaat tgtgatcaga ccataatgtt acattattat caacaatagt gattgataga    2880
gtgttatcag tcataactaa ataaagcttg caacaaaatt ctctgacaaa aaaaaaaaa    2940
aaa                                                                  2943
```

<210> SEQ ID NO 2
<211> LENGTH: 213
<212> TYPE: PRT
<213> ORGANISM: Homo sapiens

<400> SEQUENCE: 2

```
Met Ala Lys Val Pro Asp Met Phe Glu Asp Leu Lys Asn Cys Tyr Ser
1               5                   10                  15

Glu Asn Glu Glu Asp Ser Ser Ser Ile Asp His Leu Ser Leu Asn Gln
            20                  25                  30

Lys Ser Phe Tyr His Val Ser Tyr Gly Pro Leu His Asp Ser Glu Glu
        35                  40                  45

Glu Ile Ile Lys Pro Arg Ser Ala Pro Phe Ser Phe Leu Ser Asn Val
    50                  55                  60

Lys Tyr Asn Phe Met Arg Ile Ile Lys Tyr Glu Phe Ile Leu Asn Asp
65                  70                  75                  80

Ala Leu Asn Gln Ser Ile Ile Arg Ala Asn Asp Gln Tyr Leu Thr Ala
                85                  90                  95

Ala Ala Leu His Asn Leu Asp Glu Ala Val Lys Phe Asp Met Gly Ala
            100                 105                 110

Tyr Lys Ser Ser Lys Asp Asp Ala Lys Ile Thr Val Ile Leu Arg Ile
        115                 120                 125

Ser Lys Thr Gln Leu Tyr Val Thr Ala Gln Asp Glu Asp Gln Pro Val
    130                 135                 140

Leu Leu Lys Glu Met Pro Glu Ile Pro Lys Thr Ile Thr Gly Ser Glu
```

|   |   |   | 145 |   |   |   | 150 |   |   |   | 155 |   |   |   | 160 |
|---|---|---|---|---|---|---|---|---|---|---|---|---|---|---|---|
| Thr | Asn | Leu | Leu | Phe | Phe | Trp | Glu | Thr | His | Gly | Thr | Lys | Asn | Tyr | Phe |
|   |   |   |   | 165 |   |   |   |   | 170 |   |   |   |   | 175 |   |
| Thr | Ser | Val | Ala | His | Pro | Asn | Leu | Phe | Ile | Ala | Thr | Lys | Gln | Asp | Tyr |
|   |   |   | 180 |   |   |   |   | 185 |   |   |   |   | 190 |   |   |
| Trp | Val | Cys | Leu | Ala | Gly | Gly | Pro | Pro | Ser | Ile | Thr | Asp | Phe | Gln | Ile |
|   |   |   | 195 |   |   |   |   | 200 |   |   |   |   | 205 |   |   |
| Leu | Glu | Asn | Gln | Ala |
|   |   |   | 210 |   |

<210> SEQ ID NO 3
<211> LENGTH: 1498
<212> TYPE: DNA
<213> ORGANISM: Homo sapiens

<400> SEQUENCE: 3

```
accaaacctc ttcgaggcac aaggcacaac aggctgctct gggattctct tcagccaatc      60
ttcattgctc aagtgtctga agcagccatg cagaagtac ctgagctcgc cagtgaaatg     120
atggcttatt acagtggcaa tgaggatgac ttgttctttg aagctgatgg ccctaaacag     180
atgaagtgct ccttccagga cctggacctc tgccctctgg atggcggcat ccagctacga     240
atctccgacc accactacag caagggcttc aggcaggccg cgtcagttgt tgtggccatg     300
gacaagctga ggaagatgct ggttccctgc cacagacct tccaggagaa tgacctgagc     360
accttctttc ccttcatctt tgaagaagaa cctatcttct tcgacacatg ggataacgag     420
gcttatgtgc acgatgcacc tgtacgatca ctgaactgca cgctccggga ctcacagcaa     480
aaaagcttgg tgatgtctgg tccatatgaa ctgaaagctc tccacctcca gggacaggat     540
atggagcaac aagtggtgtt ctccatgtcc tttgtacaag gagaagaaag taatgacaaa     600
atacctgtgg ccttgggcct caaggaaaag aatctgtacc tgtcctgcgt gttgaaagat     660
gataagccca ctctacagct ggagagtgta gatcccaaaa attacccaaa gaagaagatg     720
gaaaagcgat ttgtcttcaa caagatagaa atcaataaca agctggaatt tgagtctgcc     780
cagttcccca actggtacat cagcacctct caagcagaaa acatgcccgt cttcctggga     840
gggaccaaag gcggccagga tataactgac ttcaccatgc aatttgtgtc ttcctaaaga     900
gagctgtacc cagagagtcc tgtgctgaat gtggactcaa tccctagggc tggcagaaag     960
ggaacagaaa ggttttttgag tacggctata gcctggactt tcctgttgtc tacaccaatg    1020
cccaactgcc tgccttaggg tagtgctaag aggatctcct gtccatcagc caggacagtc    1080
agctctctcc tttcagggcc aatccccagc ccttttgttg agccaggcct ctctcacctc    1140
tcctactcac ttaaagcccg cctgacagaa accacggcca catttggttc taagaaaccc    1200
tctgtcattc gctcccacat tctgatgagc aaccgcttcc ctatttattt atttatttgt    1260
ttgtttgttt tattcattgg tctaatttat tcaaggggg caagaagtag cagtgtctgt    1320
aaaagagcct agttttttaat agctatgaa tcaattcaat ttggactggt gtgctctctt    1380
taaatcaagt cctttaatta agactgaaaa tatataagct cagattattt aaatgggaat    1440
atttataaat gagcaaatat catactgttc aatggttctg aaataaactt cactgaag      1498
```

<210> SEQ ID NO 4
<211> LENGTH: 269
<212> TYPE: PRT
<213> ORGANISM: Homo sapiens

<400> SEQUENCE: 4

```
Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
        35                  40                  45

Gln Leu Arg Ile Ser Asp His His Tyr Ser Lys Gly Phe Arg Gln Ala
    50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
                100                 105                 110

Tyr Val His Asp Ala Pro Val Arg Ser Leu Asn Cys Thr Leu Arg Asp
            115                 120                 125

Ser Gln Gln Lys Ser Leu Val Met Ser Gly Pro Tyr Glu Leu Lys Ala
    130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
            180                 185                 190

Lys Pro Thr Leu Gln Leu Glu Ser Val Asp Pro Lys Asn Tyr Pro Lys
    195                 200                 205

Lys Lys Met Glu Lys Arg Phe Val Phe Asn Lys Ile Glu Ile Asn Asn
210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
            260                 265

<210> SEQ ID NO 5
<211> LENGTH: 1760
<212> TYPE: DNA
<213> ORGANISM: Homo sapiens

<400> SEQUENCE: 5
atttctttat aaaccacaac tctgggcccg caatggcagt ccactgcctt gctgcagtca      60
cagaatggaa atctgcagag gcctccgcag tcacctaatc actctcctcc tcttcctgtt     120
ccattcagag acgatctgcc gaccctctgg gagaaaatcc agcaagatgc aagccttcag     180
aatctgggat gttaaccaga agaccttcta tctgaggaac aaccaactag ttgctggata     240
cttgcaagga ccaaatgtca atttagaaga aagatagat gtggtaccca ttgagcctca      300
tgctctgttc ttgggaatcc atggagggaa gatgtgcctg tcctgtgtca agtctggtga     360
tgagaccaga ctccagctgg aggcagttaa catcactgac ctgagcgaga acagaaagca     420
ggacaagcgc ttcgccttca tccgctcaga cagcggcccc accaccagtt ttgagtctgc     480
cgcctgcccc ggttggttcc tctgcacagc gatggaagct gaccagcccg tcagcctcac     540
caatatgcct gacgaaggcg tcatggtcac caaattctac ttccaggagg acgagtagta     600
```

-continued

```
ctgcccaggc ctgcctgttc ccattcttgc atggcaagga ctgcagggac tgccagtccc    660
cctgccccag ggctcccggc tatgggggca ctgaggacca gccattgagg ggtggaccct    720
cagaaggcgt cacaagaacc tggtcacagg actctgcctc ctcttcaact gaccagcctc    780
catgctgcct ccagaatggt ctttctaatg tgtgaatcag agcacagcag cccctgcaca    840
aagcccttcc atgtcgcctc tgcattcagg atcaaacccc gaccacctgc ccaacctgct    900
ctcctcttgc cactgcctct tcctccctca ttccaccttc ccatgccctg gatccatcag    960
gccacttgat gacccccaac caagtggctc ccacaccctg ttttacaaaa aagaaaagac   1020
cagtccatga gggaggtttt taagggtttg tggaaaatga aaattaggat ttcatgattt   1080
tttttttca gtccccgtga aggagagccc ttcatttgga gattatgttc tttcggggag   1140
aggctgagga cttaaaatat tcctgcattt gtgaaatgat ggtgaaagta agtggtagct   1200
tttcccttct ttttcttctt tttttgtgat gtcccaactt gtaaaaatta aaagttatgg   1260
tactatgtta gccccataat ttttttttc cttttaaaac acttccataa tctggactcc   1320
tctgtccagg cactgctgcc cagcctccaa gctccatctc cactccagat tttttacagc   1380
tgcctgcagt actttacctc ctatcagaag tttctcagct cccaaggctc tgagcaaatg   1440
tggctcctgg gggttctttc ttcctctgct gaaggaataa attgctcctt gacattgtag   1500
agcttctggc acttggagac ttgtatgaaa gatggctgtg cctctgcctg tctcccccac   1560
cgggctggga gctctgcaga gcaggaaaca tgactcgtat atgtctcagg tccctgcagg   1620
gccaagcacc tagcctcgct cttggcaggt actcagcgaa tgaatgctgt atatgttggg   1680
tgcaaagttc cctacttcct gtgacttcag ctctgtttta caataaaatc ttgaaaatgc   1740
ctaaaaaaaa aaaaaaaaaa                                                1760

<210> SEQ ID NO 6
<211> LENGTH: 177
<212> TYPE: PRT
<213> ORGANISM: Homo sapiens

<400> SEQUENCE: 6

Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
            20                  25                  30

Ser Lys Met Gln Ala Phe Arg Ile Trp Asp Val Asn Gln Lys Thr Phe
        35                  40                  45

Tyr Leu Arg Asn Asn Gln Leu Val Ala Gly Tyr Leu Gln Gly Pro Asn
    50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160
```

Met Pro Asp Glu Gly Val Met Val Thr Lys Phe Tyr Phe Gln Glu Asp
            165                 170                 175

Glu

<210> SEQ ID NO 7
<211> LENGTH: 1865
<212> TYPE: DNA
<213> ORGANISM: Homo sapiens

<400> SEQUENCE: 7

| | | | | |
|---|---|---|---|---|
| gggcagctcc | accctgggag | ggactgtggc | ccaggtactg | cccgggtgct actttatggg | 60 |
| cagcagctca | gttgagttag | agtctggaag | acctcagaag | acctcctgtc ctatgaggcc | 120 |
| ctccccatgg | ctttagctga | cttgtatgaa | gaaggaggtg | gaggaggagg agaaggtgaa | 180 |
| gacaatgctg | actcaaagga | gacgatctgc | cgaccctctg | ggagaaaatc cagcaagatg | 240 |
| caagccttca | gaatctggga | tgttaaccag | aagaccttct | atctgaggaa caaccaacta | 300 |
| gttgctggat | acttgcaagg | accaaatgtc | aatttagaag | aaaagataga tgtggtaccc | 360 |
| attgagcctc | atgctctgtt | cttgggaatc | catggaggga | agatgtgcct gtcctgtgtc | 420 |
| aagtctggtg | atgagaccag | actccagctg | gaggcagtta | acatcactga cctgagcgag | 480 |
| aacagaaagc | aggacaagcg | cttcgccttc | atccgctcag | acagcggccc caccaccagt | 540 |
| tttgagtctg | ccgcctgccc | cggttggttc | tctgcacag | cgatggaagc tgaccagccc | 600 |
| gtcagcctca | ccaatatgcc | tgacgaaggc | gtcatggtca | ccaaattcta cttccaggag | 660 |
| gacgagtagt | actgcccagg | cctgcctgtt | cccattcttg | catggcaagg actgcaggga | 720 |
| ctgccagtcc | ccctgcccca | gggctcccgg | ctatggggc | actgaggacc agccattgag | 780 |
| gggtggaccc | tcagaaggcg | tcacaagaac | ctggtcacag | gactctgcct cctcttcaac | 840 |
| tgaccagcct | ccatgctgcc | tccagaatgg | tctttctaat | gtgtgaatca gagcacagca | 900 |
| gcccctgcac | aaagcccttc | catgtcgcct | ctgcattcag | gatcaaaccc cgaccacctg | 960 |
| cccaacctgc | tctcctcttg | ccactgcctc | ttcctccctc | attccacctt cccatgccct | 1020 |
| ggatccatca | ggccacttga | tgaccccccaa | ccaagtggct | cccacaccct gttttacaaa | 1080 |
| aaagaaaaga | ccagtccatg | agggaggttt | ttaagggttt | gtggaaaatg aaaattagga | 1140 |
| tttcatgatt | tttttttttc | agtccccgtg | aaggagagcc | cttcatttgg agattatgtt | 1200 |
| ctttcgggga | gaggctgagg | acttaaaata | ttcctgcatt | tgtgaaatga tggtgaaagt | 1260 |
| aagtggtagc | ttttcccttc | tttttcttct | tttttgtga | tgtcccaact tgtaaaaatt | 1320 |
| aaaagttatg | gtactatgtt | agccccataa | ttttttttt | ccttttaaaa cacttccata | 1380 |
| atctggactc | ctctgtccag | gcactgctgc | ccagcctcca | agctccatct ccactccaga | 1440 |
| ttttttacag | ctgcctgcag | tactttacct | cctatcagaa | gtttctcagc tcccaaggct | 1500 |
| ctgagcaaat | gtggctcctg | ggggttcttt | cttcctctgc | tgaaggaata aattgctcct | 1560 |
| tgacattgta | gagcttctgg | cacttggaga | cttgtatgaa | agatggctgt gcctctgcct | 1620 |
| gtctccccca | ccgggctggg | agctctgcag | agcaggaaac | atgactcgta tatgtctcag | 1680 |
| gtccctgcag | ggccaagcac | ctagcctcgc | tcttggcagg | tactcagcga atgaatgctg | 1740 |
| tatatgttgg | gtgcaaagtt | ccctacttcc | tgtgacttca | gctctgtttt acaataaaat | 1800 |
| cttgaaaatg | cctaaaaaaa | aaaaaaaaa | aaaaaaaaa | aaaaaaaaa aaaaaaaaaa | 1860 |
| aaaaa | | | | | 1865 |

<210> SEQ ID NO 8

<211> LENGTH: 180
<212> TYPE: PRT
<213> ORGANISM: Homo sapiens

<400> SEQUENCE: 8

```
Met Ala Leu Ala Asp Leu Tyr Glu Glu Gly Gly Gly Gly Glu
1               5                   10                  15

Gly Glu Asp Asn Ala Asp Ser Lys Glu Thr Ile Cys Arg Pro Ser Gly
                20                  25                  30

Arg Lys Ser Ser Lys Met Gln Ala Phe Arg Ile Trp Asp Val Asn Gln
            35                  40                  45

Lys Thr Phe Tyr Leu Arg Asn Asn Gln Leu Val Ala Gly Tyr Leu Gln
    50                  55                  60

Gly Pro Asn Val Asn Leu Glu Glu Lys Ile Asp Val Val Pro Ile Glu
65                  70                  75                  80

Pro His Ala Leu Phe Leu Gly Ile His Gly Gly Lys Met Cys Leu Ser
                85                  90                  95

Cys Val Lys Ser Gly Asp Glu Thr Arg Leu Gln Leu Glu Ala Val Asn
                100                 105                 110

Ile Thr Asp Leu Ser Glu Asn Arg Lys Gln Asp Lys Arg Phe Ala Phe
            115                 120                 125

Ile Arg Ser Asp Ser Gly Pro Thr Thr Ser Phe Glu Ser Ala Ala Cys
    130                 135                 140

Pro Gly Trp Phe Leu Cys Thr Ala Met Glu Ala Asp Gln Pro Val Ser
145                 150                 155                 160

Leu Thr Asn Met Pro Asp Glu Gly Val Met Val Thr Lys Phe Tyr Phe
                165                 170                 175

Gln Glu Asp Glu
            180
```

<210> SEQ ID NO 9
<211> LENGTH: 1802
<212> TYPE: DNA
<213> ORGANISM: Homo sapiens

<400> SEQUENCE: 9

```
gggcagctcc accctgggag ggactgtggc ccaggtactg cccgggtgct actttatggg     60
cagcagctca gttgagttag agtctggaag acctcagaag acctcctgtc ctatgaggcc    120
ctccccatgg ctttagagac gatctgccga ccctctggga gaaaatccag caagatgcaa    180
gccttcagaa tctgggatgt taaccagaag accttctatc tgaggaacaa ccaactagtt    240
gctggatact gcaaggacc aaatgtcaat ttagaagaaa agatagatgt ggtacccatt    300
gagcctcatg ctctgttctt gggaatccat ggagggaaga tgtgcctgtc ctgtgtcaag    360
tctggtgatg agaccagact ccagctggag gcagttaaca tcactgacct gagcgagaac    420
agaaagcagg acaagcgctt cgccttcatc cgctcagaca gcggccccac caccagtttt    480
gagtctgccg cctgccccgg ttggttcctc tgcacagcga tggaagctga ccagcccgtc    540
agcctcacca atatgcctga cgaaggcgtc atggtcacca aattctactt ccaggaggac    600
gagtagtact gccaggcct gcctgttccc attcttgcat ggcaaggact gcagggactg    660
ccagtccccc tgcccaggg ctcccggcta tgggggcact gaggaccagc cattgagggg    720
tggaccctca gaaggcgtca caagaacctg tcacaggac tctgcctcct cttcaactga    780
ccagcctcca tgctgcctcc agaatggtct ttctaatgtg tgaatcagag cacagcagcc    840
cctgcacaaa gcccttccat gtcgcctctg cattcaggat caaaccccga ccacctgccc    900
```

```
aacctgctct cctcttgcca ctgcctcttc ctccctcatt ccaccttccc atgccctgga    960
tccatcaggc cacttgatga ccccaacca agtggctccc acaccctgtt ttacaaaaaa   1020
gaaaagacca gtccatgagg gaggttttta agggtttgtg aaaatgaaa attaggattt   1080 catgattttt tttttttcagt ccccgtgaag gagagcccctt catttggaga ttatgttctt   1140
tcggggagag gctgaggact taaaatattc ctgcatttgt gaaatgatgg tgaaagtaag   1200
tggtagcttt tcccttcttt ttcttctttt tttgtgatgt cccaacttgt aaaaattaaa   1260
agttatggta ctatgttagc cccataattt ttttttttcct tttaaaacac ttccataatc   1320
tggactcctc tgtccaggca ctgctgccca gcctccaagc tccatctcca ctccagattt   1380
tttacagctg cctgcagtac tttacctcct atcagaagtt tctcagctcc caaggctctg   1440
agcaaatgtg gctcctgggg gttctttctt cctctgctga aggaataaat tgctccttga   1500
cattgtagag cttctggcac ttggagactt gtatgaaaga tggctgtgcc tctgcctgtc   1560 tccccaccg ggctgggagc tctgcagagc aggaaacatg actcgtatat gtctcaggtc   1620
cctgcagggc caagcaccta gcctcgctct tggcaggtac tcagcgaatg aatgctgtat   1680
atgttgggtg caaagttccc tacttcctgt gacttcagct ctgttttaca ataaaatctt   1740
gaaaatgcct aaaaaaaaaa aaaaaaaaaa aaaaaaaaaa aaaaaaaaaa aaaaaaaaaa   1800
aa                                                                  1802
```

<210> SEQ ID NO 10
<211> LENGTH: 159
<212> TYPE: PRT
<213> ORGANISM: Homo sapiens

<400> SEQUENCE: 10

Met Ala Leu Glu Thr Ile Cys Arg Pro Ser Gly Arg Lys Ser Ser Lys
1               5                  10                  15

Met Gln Ala Phe Arg Ile Trp Asp Val Asn Gln Lys Thr Phe Tyr Leu
            20                  25                  30

Arg Asn Asn Gln Leu Val Ala Gly Tyr Leu Gln Gly Pro Asn Val Asn
        35                  40                  45

Leu Glu Glu Lys Ile Asp Val Val Pro Ile Glu Pro His Ala Leu Phe
    50                  55                  60

Leu Gly Ile His Gly Gly Lys Met Cys Leu Ser Cys Val Lys Ser Gly
65                  70                  75                  80

Asp Glu Thr Arg Leu Gln Leu Glu Ala Val Asn Ile Thr Asp Leu Ser
                85                  90                  95

Glu Asn Arg Lys Gln Asp Lys Arg Phe Ala Phe Ile Arg Ser Asp Ser
            100                 105                 110

Gly Pro Thr Thr Ser Phe Glu Ser Ala Ala Cys Pro Gly Trp Phe Leu
        115                 120                 125

Cys Thr Ala Met Glu Ala Asp Gln Pro Val Ser Leu Thr Asn Met Pro
    130                 135                 140

Asp Glu Gly Val Met Val Thr Lys Phe Tyr Phe Gln Glu Asp Glu
145                 150                 155

<210> SEQ ID NO 11
<211> LENGTH: 1973
<212> TYPE: DNA
<213> ORGANISM: Homo sapiens

<400> SEQUENCE: 11

| | |
|---|---|
| gggcagctcc accctgggag ggactgtggc ccaggtactg cccgggtgct actttatggg | 60 |
| cagcagctca gttgagttag agtctggaag acctcagaag acctcctgtc ctatgaggcc | 120 |
| ctccccatgg ctttaggggg attataaaac taatcatcaa agccaagaag gcaagagcaa | 180 |
| gcatgtaccg ctgaaaacac aagataactg cataagtaat gactttcagt gcagattcat | 240 |
| agctaaccca taaactgctg ggcaaaaat catcttggaa ggctctgaac ctcagaaagg | 300 |
| attcacaaga cgatctgccg accctctggg agaaaatcca gcaagatgca agccttcaga | 360 |
| atctgggatg ttaaccagaa gaccttctat ctgaggaaca accaactagt tgctggatac | 420 |
| ttgcaaggac caaatgtcaa tttagaagaa aagatagatg tggtacccat tgagcctcat | 480 |
| gctctgttct tgggaatcca tggagggaag atgtgcctgt cctgtgtcaa gtctggtgat | 540 |
| gagaccagac tccagctgga ggcagttaac atcactgacc tgagcgagaa cagaaagcag | 600 |
| gacaagcgct tcgccttcat ccgctcagac agcggcccca ccaccagttt tgagtctgcc | 660 |
| gcctgccccg gttggttcct ctgcacagcg atggaagctg accagcccgt cagcctcacc | 720 |
| aatatgcctg acgaaggcgt catggtcacc aaattctact tccaggagga cgagtagtac | 780 |
| tgcccaggcc tgcctgttcc cattcttgca tggcaaggac tgcagggact gccagtcccc | 840 |
| ctgccccagg gctcccggct atgggggcac tgaggaccag ccattgaggg gtggacccctc | 900 |
| agaaggcgtc acagaacct ggtcacagga ctctgcctcc tcttcaactg accagcctcc | 960 |
| atgctgcctc cagaatggtc tttctaatgt gtgaatcaga gcacagcagc ccctgcacaa | 1020 |
| agcccttcca tgtcgcctct gcattcagga tcaaaccccg accacctgcc caacctgctc | 1080 |
| tcctcttgcc actgcctctt cctccctcat tccaccttcc catgccctgg atccatcagg | 1140 |
| ccacttgatg accccaacc aagtggctcc cacaccctgt tttacaaaaa agaaagacc | 1200 |
| agtccatgag ggaggttttt aagggtttgt ggaaaatgaa aattaggatt tcatgattt | 1260 |
| ttttttcag tccccgtgaa ggagagccct tcatttggag attatgttct tcggggaga | 1320 |
| ggctgaggac ttaaaatatt cctgcatttg tgaaatgatg gtgaaagtaa gtggtagctt | 1380 |
| ttcccttctt tttcttcttt ttttgtgatg tcccaacttg taaaaattaa aagttatggt | 1440 |
| actatgttag ccccataatt ttttttttcc ttttaaaaca cttccataat ctggactcct | 1500 |
| ctgtccaggc actgctgccc agcctccaag ctccatctcc actccagatt ttttacagct | 1560 |
| gcctgcagta ctttacctcc tatcagaagt ttctcagctc ccaaggctct gagcaaatgt | 1620 |
| ggctcctggg ggttctttct tcctctgctg aaggaataaa ttgctccttg acattgtaga | 1680 |
| gcttctggca cttggagact tgtatgaaag atggctgtgc ctctgcctgt ctcccccacc | 1740 |
| gggctgggag ctctgcagag caggaaacat gactcgtata tgtctcaggt ccctgcaggg | 1800 |
| ccaagcacct agcctcgctc ttggcaggta ctcagcgaat gaatgctgta tatgttgggt | 1860 |
| gcaaagttcc ctacttcctg tgacttcagc tctgttttac aataaaatct tgaaaatgcc | 1920 |
| taaaaaaaaa aaaaaaaaaa aaaaaaaaaa aaaaaaaaa aaaaaaaaa aaa | 1973 |

<210> SEQ ID NO 12
<211> LENGTH: 143
<212> TYPE: PRT
<213> ORGANISM: Homo sapiens

<400> SEQUENCE: 12

Met Gln Ala Phe Arg Ile Trp Asp Val Asn Gln Lys Thr Phe Tyr Leu
1               5                   10                  15

Arg Asn Asn Gln Leu Val Ala Gly Tyr Leu Gln Gly Pro Asn Val Asn
            20                  25                  30

Leu Glu Glu Lys Ile Asp Val Val Pro Ile Glu Pro His Ala Leu Phe
            35                  40                  45

Leu Gly Ile His Gly Gly Lys Met Cys Leu Ser Cys Val Lys Ser Gly
        50                  55                  60

Asp Glu Thr Arg Leu Gln Leu Glu Ala Val Asn Ile Thr Asp Leu Ser
65                  70                  75                  80

Glu Asn Arg Lys Gln Asp Lys Arg Phe Ala Phe Ile Arg Ser Asp Ser
                85                  90                  95

Gly Pro Thr Thr Ser Phe Glu Ser Ala Ala Cys Pro Gly Trp Phe Leu
            100                 105                 110

Cys Thr Ala Met Glu Ala Asp Gln Pro Val Ser Leu Thr Asn Met Pro
        115                 120                 125

Asp Glu Gly Val Met Val Thr Lys Phe Tyr Gln Glu Asp Glu
    130                 135                 140

<210> SEQ ID NO 13
<211> LENGTH: 602
<212> TYPE: DNA
<213> ORGANISM: Homo sapiens

<400> SEQUENCE: 13
agctccaccc tgggagggac tgtggcccag gtactgcccg ggtgctactt tatgggcagc      60
agctcagttg agttagagtc tggaagacct cagaagacct cctgtcctat gaggccctcc     120
ccatggcttt agagacgatc tgccgaccct ctgggagaaa atccagcaag atgcaagcct     180
tcagaatctg ggatgttaac cagaagacct tctatctgag gaacaaccaa ctagttgctg     240
gatacttgca aggaccaaat gtcaatttag aagaaaagat agatgtggta cccattgagc     300
ctcatgctct gttcttggga atccatggag gaaagatgtg cctgtcctgt gtcaagtctg     360
gtgatgagac cagactccag ctggaggcag ttaacatcac tgacctgagc gagaacagaa     420
agcaggacaa gcgcttcgcc ttcatccgct cagacagtgg ccccaccacc agttttgagt     480
ctgccgcctg ccccggttgg ttcctctgca gcgatggaa agctgaccag cccgtcagcc     540
tcaccaatat gcctgacgaa ggcgtcatgg tcaccaaatt ctacttccag gaggacgagt     600
ag                                                                    602

<210> SEQ ID NO 14
<211> LENGTH: 159
<212> TYPE: PRT
<213> ORGANISM: Homo sapiens

<400> SEQUENCE: 14

Met Ala Leu Glu Thr Ile Cys Arg Pro Ser Gly Arg Lys Ser Ser Lys
1               5                   10                  15

Met Gln Ala Phe Arg Ile Trp Asp Val Asn Gln Lys Thr Phe Tyr Leu
            20                  25                  30

Arg Asn Asn Gln Leu Val Ala Gly Tyr Leu Gln Gly Pro Asn Val Asn
        35                  40                  45

Leu Glu Glu Lys Ile Asp Val Val Pro Ile Glu Pro His Ala Leu Phe
    50                  55                  60

Leu Gly Ile His Gly Gly Lys Met Cys Leu Ser Cys Val Lys Ser Gly
65                  70                  75                  80

Asp Glu Thr Arg Leu Gln Leu Glu Ala Val Asn Ile Thr Asp Leu Ser
                85                  90                  95

Glu Asn Arg Lys Gln Asp Lys Arg Phe Ala Phe Ile Arg Ser Asp Ser

```
            100                 105                 110
Gly Pro Thr Thr Ser Phe Glu Ser Ala Ala Cys Pro Gly Trp Phe Leu
        115                 120                 125

Cys Thr Ala Met Glu Ala Asp Gln Pro Val Ser Leu Thr Asn Met Pro
130                 135                 140

Asp Glu Gly Val Met Val Thr Lys Phe Tyr Phe Gln Glu Asp Glu
145                 150                 155
```

<210> SEQ ID NO 15
<211> LENGTH: 602
<212> TYPE: DNA
<213> ORGANISM: Homo sapiens

<400> SEQUENCE: 15

```
agctccaccc tgggagggac tgtggcccag gtactgcccg ggtgctactt tatgggcagc     60
agctcagttg agttagagtc tggaagacct cagaagacct cctgtcctat gaggccctcc    120
ccatggcttt agagacgatc tgccgaccct ctgggagaaa atccagcaag atgcaagcct    180
tcagaatctg ggatgttaac cagaagacct tctatctgag gaacaaccaa ctagttgctg    240
gatacttgca aggaccaaat gtcaatttag aagaaaagat agatgtggta cccattgagc    300
ctcatgctct gttcttggga atccatggag ggaagatgtg cctgtcctgt gtcaagtctg    360
gtgatgagac cagactccag ctggaggcag ttaacatcac tgacctgagc gagaacagaa    420
agcaggacaa gcgcttcgcc ttcatccgct cagacagtgg ccccaccacc agttttgagt    480
ctgccgcctg ccccggttgg ttcctctgca cagcgatgga agctgaccag cccgtcagcc    540
tcaccaatat gcctgacgaa ggcgtcatgg tcaccaaatt ctacttccag gaggacgagt    600
ag                                                                   602
```

<210> SEQ ID NO 16
<211> LENGTH: 153
<212> TYPE: PRT
<213> ORGANISM: Homo sapiens

<400> SEQUENCE: 16

```
Met Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45

Val Val Pro Ile Glu Pro His Ala Leu Phe Leu Gly Ile His Gly Gly
    50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

Asp Gln Pro Val Ser Leu Thr Asn Met Pro Asp Glu Gly Val Met Val
    130                 135                 140

Thr Lys Phe Tyr Phe Gln Glu Asp Glu
145                 150
```

<210> SEQ ID NO 17
<211> LENGTH: 4909
<212> TYPE: DNA
<213> ORGANISM: Homo sapiens

<400> SEQUENCE: 17

```
tagacgcacc ctctgaagat ggtgactccc tcctgagaag ctggacccct tggtaaaaga      60
caaggccttc tccaagaaga atatgaaagt gttactcaga cttatttgtt tcatagctct     120
actgatttct tctctggagg ctgataaatg caaggaacgt gaagaaaaaa taattttagt     180
gtcatctgca aatgaaattg atgttcgtcc ctgtcctctt aacccaaatg aacacaaagg     240
cactataact tggtataaag atgacagcaa gacacctgta tctacagaac aagcctccag     300
gattcatcaa cacaaagaga aactttggtt tgttcctgct aaggtggagg attcaggaca     360
ttactattgc gtggtaagaa attcatctta ctgcctcaga attaaaataa gtgcaaaatt     420
tgtggagaat gagcctaact tatgttataa tgcacaagcc atatttaagc agaaactacc     480
cgttgcagga gacggaggac ttgtgtgccc ttatatggag tttttttaaaa atgaaaataa     540 tgagttacct aaattacagt ggtataagga ttgcaaacct ctacttcttg acaatataca     600
ctttagtgga gtcaaagata ggctcatcgt gatgaatgtg gctgaaaagc atagagggaa     660
ctatacttgt catgcatcct acacatactt gggcaagcaa tatcctatta cccgggtaat     720
agaatttatt actctagagg aaaacaaacc cacaaggcct gtgattgtga gcccagctaa     780
tgagacaatg aagtagact tgggatccca gatacaattg atctgtaatg tcaccggcca     840
gttgagtgac attgcttact ggaagtggaa tgggtcagta attgatgaag atgacccagt     900 gctagggaa gactattaca gtgtggaaaa tcctgcaaac aaaagaagga gtaccctcat     960
cacagtgctt aatatatcgg aaattgaaag tagattttat aaacatccat ttacctgttt    1020
tgccaagaat acacatggta tagatgcagc atatatccag ttaatatatc cagtcactaa    1080
tttccagaag cacatgattg gtatatgtgt cacgttgaca gtcataattg tgtgttctgt    1140
tttcatctat aaaatcttca agattgacat tgtgctttgg tacagggatt cctgctatga    1200 tttttctccca ataaaagctt cagatggaaa gacctatgac gcatatatac tgtatccaaa    1260
gactgttggg gaagggtcta cctctgactg tgatatttt gtgtttaaag tcttgcctga    1320
ggtcttggaa aaacagtgtg gatataagct gttcattat ggaagggatg actacgttgg    1380
ggaagacatt gttgaggtca ttaatgaaaa cgtaaagaaa agcagaagac tgattatcat    1440
tttagtcaga gaaacatcag gcttcagctg gctgggtggt tcatctgaag agcaaatagc    1500
catgtataat gctcttgttc aggatggaat taaagttgtc ctgcttgagc tggagaaaat    1560
ccaagactat gagaaaatgc agaatcgat taaattcatt aagcagaaac atggggctat    1620
ccgctggtca ggggacttta cacagggacc acagtctgca aagacaaggt tctggaagaa    1680
tgtcaggtac cacatgccag tccagcgacg gtcaccttca tctaaacacc agttactgtc    1740
accagccact aaggagaaac tgcaaagaga ggctcacgtg cctctcgggt agcatggaga    1800
agttgccaag agttctttag gtgcctcctg tcttatggcg ttgcaggcca ggttatgcct    1860
catgctgact tgcagagttc atggaatgta actatatcat cctttatccc tgaggtcacc    1920
tggaatcaga ttattaaggg aataagccat gacgtcaata gcagcccagg cacttcaga    1980 gtagagggct tgggaagatc ttttaaaaag gcagtaggcc cggtgtggtg gctcacgcct    2040
ataatcccag cactttggga ggctgaagtg gtggatcac cagaggtcag gagttcgaga    2100
ccagcccagc caacatggca aaaccccatc tctactaaaa atacaaaaat gagctaggca    2160
```

```
tggtggcaca cgcctgtaat cccagctaca cctgaggctg aggcaggaga attgcttgaa    2220
ccggggagac ggaggttgca gtgagccgag tttgggccac tgcactctag cctggcaaca    2280
gagcaagact ccgtctcaaa aaagggcaa taaatgccct ctctgaatgt ttgaactgcc     2340
aagaaaaggc atggagacag cgaactagaa gaaagggcaa gaaggaaata gccaccgtct    2400
acagatggct tagttaagtc atccacagcc caagggcggg gctatgcctt gtctggggac    2460
cctgtagagt cactgacect ggagcggctc tcctgagagg tgctgcaggc aaagtgagac    2520
tgacacctca ctgaggaagg gagacatatt cttggagaac tttccatctg cttgtatttt    2580
ccatacacat ccccagccag aagttagtgt ccgaagaccg aatttatttt tacagagctt    2640
gaaaactcac ttcaatgaac aaagggattc tccaggattc caaagttttg aagtcatctt    2700
agctttccac aggagggaga gaacttaaaa aagcaacagt agcagggaat tgatccactt    2760
cttaatgctt tcctccctgg catgaccatc ctgtcctttg ttattatcct gcattttacg    2820
tctttggagg aacagctccc tagtggcttc tccgtctgc aatgtccctt gcacagccca     2880
cacatgaacc atccttccca tgatgccgct cttctgtcat cccgctcctg ctgaaacacc    2940 tcccagggggc tccacctgtt caggagctga agcccatgct ttcccaccag catgtcactc   3000
ccagaccacc tccctgccct gtcctccagc ttcccctcgc tgtcctgctg tgtgaattcc    3060
caggttggcc tggtggccat gtcgcctgcc cccagcactc ctctgtctct gctcttgcct    3120
cgacccttcc tcctcctttg cctaggaggc cttctcgcat tttctctagc tgatcagaat    3180
tttaccaaaa ttcagaacat cctccaattc cacagtctct gggagacttt ccctaagagg    3240
cgacttcctc tccagccttc tctctctggt caggcccact gcagagatgg tggtgagcac    3300
atctgggagg ctggtctccc tccagctgga attgctgctc tctgagggag aggctgtggt    3360
ggctgtctct gtccctcact gccttccagg agcaatttgc acatgtaaca tagatttatg    3420
taatgcttta tgtttaaaaa cattccccaa ttatcttatt aattttttgc aattattcta    3480
attttatata tagagaaagt gacctatttt ttaaaaaaat cacactctaa gttctattga    3540
acctaggact tgagcctcca tttctggctt ctagtctggt gttctgagta cttgatttca    3600
ggtcaataac ggtccccct cactccacac tggcacgttt gtgagaagaa atgacatttt     3660
gctaggaagt gaccgagtct aggaatgctt ttattcaaga caccaaattc caaacttcta    3720
aatgttggaa ttttcaaaaa ttgtgtttag attttatgaa aaactcttct actttcatct    3780
attctttccc tagaggcaaa catttcttaa aatgtttcat tttcattaaa aatgaaagcc    3840
aaatttatat gccaccgatt gcaggacaca agcacagttt taagagttgt atgaacatgg    3900
agaggacttt tggttttat atttctcgta tttaatatgg gtgaacacca acttttattt     3960
ggaataataa ttttcctcct aaacaaaaac acattgagtt taagtctctg actcttgcct    4020
ttccacctgc tttctcctgg gcccgctttg cctgcttgaa ggaacagtgc tgttctggag    4080
ctgctgttcc aacagacagg gcctagcttt catttgacac acagactaca gccagaagcc    4140
catggagcag ggatgtcacg tcttgaaaag cctattagat gttttacaaa tttaattttg    4200
cagattattt tagtctgtca tccagaaaat gtgtcagcat gcatagtgct aagaaagcaa    4260
gccaatttgg aaacttaggt tagtgacaaa attggccaga gagtgggggt gatgatgacc    4320
aagaattaca agtagaatgg cagctggaat ttaaggaggg acaagaatca atggataagc    4380
gtgggtggag gaagatccaa acagaaaagt gcaaagttat tccccatctt ccaagggttg    4440
aattctggag gaagaagaca cattcctagt tccccgtgaa cttcctttga cttattgtcc    4500
```

-continued

```
ccactaaaac aaaacaaaaa acttttaatg ccttccacat taattagatt ttcttgcagt    4560 tttttttatgg catttttta aagatgccct aagtgttgaa gaagagtttg caaatgcaac    4620
aaaatattta attaccggtt gttaaaactg gtttagcaca atttatattt tccctctctt    4680
gcctttctta tttgcaataa aaggtattga gccattttttt aaatgacatt tttgataaat    4740
tatgtttgta ctagttgatg aaggagtttt ttttaacctg tttatataat tttgcagcag    4800
aagccaaatt ttttgtatat taaagcacca aattcatgta cagcatgcat cacggatcaa    4860
tagactgtac ttatttttcca ataaaattttt caaactttgt actgttaaa              4909

<210> SEQ ID NO 18
<211> LENGTH: 569
<212> TYPE: PRT
<213> ORGANISM: Homo sapiens

<400> SEQUENCE: 18

Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Lys Ile Ile Leu
            20                  25                  30

Val Ser Ser Ala Asn Glu Ile Asp Val Arg Pro Cys Pro Leu Asn Pro
        35                  40                  45

Asn Glu His Lys Gly Thr Ile Thr Trp Tyr Lys Asp Asp Ser Lys Thr
    50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
        115                 120                 125

Lys Gln Lys Leu Pro Val Ala Gly Asp Gly Gly Leu Val Cys Pro Tyr
    130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
        195                 200                 205

Ile Thr Arg Val Ile Glu Phe Ile Thr Leu Glu Glu Asn Lys Pro Thr
    210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
        275                 280                 285

Arg Ser Thr Leu Ile Thr Val Leu Asn Ile Ser Glu Ile Glu Ser Arg
    290                 295                 300
```

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Phe Gln Lys
            325                 330                 335

His Met Ile Gly Ile Cys Val Thr Leu Thr Val Ile Ile Val Cys Ser
                340                 345                 350

Val Phe Ile Tyr Lys Ile Phe Lys Ile Asp Ile Val Leu Trp Tyr Arg
        355                 360                 365

Asp Ser Cys Tyr Asp Phe Leu Pro Ile Lys Ala Ser Asp Gly Lys Thr
    370                 375                 380

Tyr Asp Ala Tyr Ile Leu Tyr Pro Lys Thr Val Gly Glu Gly Ser Thr
385                 390                 395                 400

Ser Asp Cys Asp Ile Phe Val Phe Lys Val Leu Pro Glu Val Leu Glu
                405                 410                 415

Lys Gln Cys Gly Tyr Lys Leu Phe Ile Tyr Gly Arg Asp Asp Tyr Val
            420                 425                 430

Gly Glu Asp Ile Val Glu Val Ile Asn Glu Asn Val Lys Lys Ser Arg
                435                 440                 445

Arg Leu Ile Ile Ile Leu Val Arg Glu Thr Ser Gly Phe Ser Trp Leu
        450                 455                 460

Gly Gly Ser Ser Glu Glu Gln Ile Ala Met Tyr Asn Ala Leu Val Gln
465                 470                 475                 480

Asp Gly Ile Lys Val Val Leu Leu Glu Leu Glu Lys Ile Gln Asp Tyr
                485                 490                 495

Glu Lys Met Pro Glu Ser Ile Lys Phe Ile Lys Gln Lys His Gly Ala
            500                 505                 510

Ile Arg Trp Ser Gly Asp Phe Thr Gln Gly Pro Gln Ser Ala Lys Thr
        515                 520                 525

Arg Phe Trp Lys Asn Val Arg Tyr His Met Pro Val Gln Arg Arg Ser
    530                 535                 540

Pro Ser Ser Lys His Gln Leu Leu Ser Pro Ala Thr Lys Glu Lys Leu
545                 550                 555                 560

Gln Arg Glu Ala His Val Pro Leu Gly
                565

<210> SEQ ID NO 19
<211> LENGTH: 1484
<212> TYPE: DNA
<213> ORGANISM: Homo sapiens

<400> SEQUENCE: 19
cccgtgagga ggaaaaggtg tgtccgctgc cacccagtgt gagcgggtga cacccacccgg     60 ttaggaaatc ccagctccca agagggtata atccctgct ttactgctga gctcctgctg     120
gaggtgaaag tctggcctgg cagccttccc caggtgagca gcaacaaggc cacgtgctgc     180
tgggtctcag tcctccactt cccgtgtcct ctggaagttg tcaggagcaa tgttgcgctt     240
gtacgtgttg gtaatgggag tttctgcctt cacccttcag cctgcggcac acacaggggc     300
tgccagaagc tgccggtttc gtgggaggca ttacaagcgg gagttcaggc tggaagggga     360
gcctgtagcc ctgaggtgcc cccaggtgcc ctactggttg tgggcctctg tcagccccg     420 catcaacctg acatggcata aaaatgactc tgctaggacg gtcccaggag aagaagagac     480
acggatgtgg gccaggacg gtgctctgtg gcttctgcca gccttgcagg aggactctgg     540
cacctacgtc tgcactacta gaaatgcttc ttactgtgac aaaatgtcca ttgagctcag     600

```
agtttttgag aatacagatg ctttcctgcc gttcatctca tacccgcaaa ttttaacctt    660
gtcaacctct ggggtattag tatgccctga cctgagtgaa ttcacccgtg acaaaactga    720
cgtgaagatt caatggtaca aggattctct tcttttggat aaagacaatg agaaatttct    780
aagtgtgagg gggaccactc acttactcgt acacgatgtg gccctggaag atgctggcta    840
ttaccgctgt gtcctgacat tgcccatga aggccagcaa tacaacatca ctaggagtat    900
tgagctacgc atcaagaaaa aaaaagaaga gaccattcct gtgatcattt ccccctcaa    960
gaccatatca gcttctctgg ggtcaagact gacaatcccg tgtaaggtgt tctgggaac   1020
cggcacaccc ttaaccacca tgctgtggtg gacggccaat gacacccaca tagagagcgc   1080
ctacccggga ggccgcgtga ccgaggggcc acgccaggaa tattcagaaa ataatgagaa   1140
ctacattgaa gtgccattga ttttgatcc tgtcacaaga gaggatttgc acatggattt   1200
taaatgtgtt gtccataata ccctgagttt tcagacacta cgcaccacag tcaaggaagc   1260
ctcctccacg ttctcctggg gcattgtgct ggccccactt tcactggcct tcttggtttt   1320
gggggggaata tggatgcaca gacggtgcaa acacagaact ggaaaagcag atggtctgac   1380
tgtgctatgg cctcatcatc aagactttca atcctatccc aagtgaaata atggaatga   1440
aataattcaa acacaaaaaa aaaaaaaaaa aaaaaaaaaa aaaa                   1484

<210> SEQ ID NO 20
<211> LENGTH: 1436
<212> TYPE: DNA
<213> ORGANISM: Homo sapiens

<400> SEQUENCE: 20
gggatgggag atactgttgt ggtcacctct ggaaaataca ttctgctact cttaaaaact     60
agtgacgctc atacaaatca acagaaagag cttctgaagg aagactttaa agctgcttct    120
gccacgtgct gctgggtctc agtcctccac ttcccgtgtc ctctggaagt tgtcaggagc    180
aatgttgcgc ttgtacgtgt tggtaatggg agtttctgcc ttcacccttc agcctgcggc    240
acacacaggg gctgccagaa gctgccggtt tcgtgggagg cattacaagc gggagttcag    300
gctggaaggg gagcctgtag ccctgaggtg ccccaggtg ccctactggt tgtgggcctc    360
tgtcagcccc cgcatcaacc tgacatggca taaaaatgac tctgctagga cggtcccagg    420
agaagaagag cacgcggatgt gggcccagga cggtgctctg tggcttctgc cagccttgca    480
ggaggactct ggcacctacg tctgcactac tagaaatgct tcttactgtg acaaaatgtc    540
cattgagctc agagttttg agaatacaga tgctttcctg ccgttcatct catacccgca    600
aattttaacc ttgtcaacct ctggggtatt agtatgccct gacctgagtg aattcacccg    660
tgacaaaact gacgtgaaga ttcaatggta caaggattct cttcttttgg ataaagacaa    720
tgagaaattt ctaagtgtga gggggaccac tcacttactc gtacacgatg tggccctgga    780
agatgctggc tattaccgct gtgtcctgac atttgcccat gaaggccagc aatacaacat    840
cactaggagt attgagctac gcatcaagaa aaaaaagaa gagaccattc ctgtgatcat    900
tccccctc aagaccatat cagcttctct ggggtcaaga ctgacaatcc cgtgtaaggt    960
gtttctggga accggcacac ccttaaccac catgctgtgg tggacggcca atgacaccca   1020
catagagagc gcctacccgg gaggccgcgt gaccgagggg ccacgccagg aatattcaga   1080
aaataatgag aactacattg aagtgccatt gattttgat cctgtcacaa gagaggattt   1140
gcacatggat tttaaatgtg ttgtccataa taccctgagt tttcagacac tacgcaccac   1200
agtcaaggaa gcctcctcca cgttctcctg gggcattgtg ctggccccac tttcactggc   1260
```

```
cttcttggtt ttgggggggaa tatggatgca cagacggtgc aaacacagaa ctggaaaagc      1320
agatggtctg actgtgctat ggcctcatca tcaagacttt caatcctatc ccaagtgaaa      1380
taaatggaat gaaataattc aaacacaaaa aaaaaaaaaa aaaaaaaaaa aaaaaa          1436
```

<210> SEQ ID NO 21
<211> LENGTH: 398
<212> TYPE: PRT
<213> ORGANISM: Homo sapiens

<400> SEQUENCE: 21

```
Met Leu Arg Leu Tyr Val Leu Val Met Gly Val Ser Ala Phe Thr Leu
1               5                   10                  15

Gln Pro Ala Ala His Thr Gly Ala Ala Arg Ser Cys Arg Phe Arg Gly
            20                  25                  30

Arg His Tyr Lys Arg Glu Phe Arg Leu Glu Gly Glu Pro Val Ala Leu
        35                  40                  45

Arg Cys Pro Gln Val Pro Tyr Trp Leu Trp Ala Ser Val Ser Pro Arg
    50                  55                  60

Ile Asn Leu Thr Trp His Lys Asn Asp Ser Ala Arg Thr Val Pro Gly
65                  70                  75                  80

Glu Glu Glu Thr Arg Met Trp Ala Gln Asp Gly Ala Leu Trp Leu Leu
                85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
            180                 185                 190

Leu Val His Asp Val Ala Leu Glu Asp Ala Gly Tyr Tyr Arg Cys Val
        195                 200                 205

Leu Thr Phe Ala His Glu Gly Gln Gln Tyr Asn Ile Thr Arg Ser Ile
    210                 215                 220

Glu Leu Arg Ile Lys Lys Lys Glu Glu Thr Ile Pro Val Ile Ile
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
        275                 280                 285

Arg Val Thr Glu Gly Pro Arg Gln Glu Tyr Ser Glu Asn Asn Glu Asn
    290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
                325                 330                 335

Leu Arg Thr Thr Val Lys Glu Ala Ser Ser Thr Phe Ser Trp Gly Ile
```

```
            340             345             350
Val Leu Ala Pro Leu Ser Leu Ala Phe Leu Val Leu Gly Gly Ile Trp
        355                 360                 365

Met His Arg Arg Cys Lys His Arg Thr Gly Lys Ala Asp Gly Leu Thr
    370                 375                 380

Val Leu Trp Pro His His Gln Asp Phe Gln Ser Tyr Pro Lys
385                 390                 395

<210> SEQ ID NO 22
<211> LENGTH: 3177
<212> TYPE: DNA
<213> ORGANISM: Homo sapiens

<400> SEQUENCE: 22
cagaagacct cctgtcctat gaggccctcc ccatggcttt aggtaagctc cttccactct     60 catttttca cctgagaaat gagagaggaa aatgtctaca attggtgttt atcaaatgct    120
ttcaggctct ggtgagcaag cgtccaggaa aatgtcaagc gcatggagct ccaggcctgt    180 ctggggatc tgggcacggg gaggcatcca tgggagacca tgcaggcact ctgaggcagg    240
ggctgcaagc tagtgcctgc tggggcagca ggtgaacaga gaggtgtaac tgctgtgaca    300
gaagtcatgg agtccttgga gtgtgagggt cattttccac tgttgataga atagggaaat    360
tggtgaaata gccctgttaa atgagagaaa gaacagtgtg agctcaatga gaaatactaa    420
tagaatgtgg cactgagcca caaggtctga gggttgattg ataaggaagg gtggggactg    480
tggagaatta agggcttggc acaggtcagt tccaccagtt gtcacaagag aatgcaggct    540
caggtggcca gaacttctcg cttttccaga agagtccgat attctgattt cattatatat    600
agtattctga ttaaaccaga caataaagca agcagataaa atatttaaag tataagctgc    660
cagtttgcaa cctccggtta ggatttgtgt ggggcaaaga aaaaaactct caggatcatt    720
ggtatgtaga ctctaatttt aagtttctaa tttaaaattg gcccctgagg ctgggcgtgg    780
tggctcacac ctgtaatccc agcattttgg gaggccaagg tgggtggatc tcttgaggtc    840
aagagttcaa ggcctgcctg gccaacatgt gaaaccctg tctctattaa aaatacaaaa    900
attagctggg catggtggtg catgtctgca atcttagcta cttgggtagc taaggcagga    960
gaattgctgg aacccgggag gtagaggttg cagtgaatgg agatcacacc actgcactcc   1020
agtctgggca atagagagag acgctctctc taaaaaaaaa tatgtaaaga taaataaaat   1080
gaaataaaat aggcctctaa tgagcaggcc attctccttt ctgggtctta ctttccttgc   1140
actcctttct gggtgttaag aggaggtcta gaggaagctg acaactctt agcttgtagt   1200 aagcacagtg gaagtatcag ctcttaatgg gtcatggaca cgttacgaag ctaggcgccg   1260
tgctgagcac tttacatggt ttatcccact gaaccctctc aataaccta tgaggaaggg   1320 ctattattgc tcacattttc agaagaggaa atggatatag agagattaga taatttgccc   1380
atggccagac agctagtata agaggaggag gtggattgac tgcagacatt ctgtcttcaa   1440
accactacac tatgctatgg aggcacagag acttaatgaa atcatggaga ggggaattgc   1500
tttgtcaacc acaagcagtt attccggggg cagcagatcc tcccctgtcc cccagtggta   1560
caatggtccc tggtgggttg tgctacaatg ttagcccatg gtcttatgtg tttttcaaat   1620
gtgtaaagta ggatgctgga accactctta gaaccagata ccaatacatt gtgaagaaat   1680
aaatctctgt gcttaaaact ggttcatccc aaaatatttt gaactgacac acaataggtg   1740
ctaaataaat gtgtgttaac ttgaattgga ttgaattcgg gaaaaagtg caataagctt   1800
```

```
agtgaagaca ccatgttccc tgggtagagg aaccacattc tccatctaag gccaggagta   1860
tgggaggtat caatgtttgc ccagcacaga acagggtgcc aagaagagaa aagttgacgg   1920
ggtgcatact ctgactggaa actggaaggg tgagaacaga gggtaaagga tagagatgga   1980
accatgtgca tacactttgt gttaccttgg acaagtcatt catttctctg gacctctgct   2040
ttctctctac acaatggggt cccaccactt cccttacagc tgacttgtat gaagaaggag   2100
gtggaggagg aggagaaggt gaagacaatg ctgactcaaa gggtaaatta tttttaggat   2160
ccaagtttga aaacaatttt aggctactag atatgaacaa catcttgatt atgtagttga   2220
aggaaattaa agatgaatgg tttaattaaa aattaatcag aatgaaaacg attgattact   2280
aatatatctg caatggttta ttttcctgag tggcagactc actaaggttt ttgaatactc   2340
ctgtgtgatt gctctatgta tgtatgtatg tatgtatgta tgcatgtatc tatctatctg   2400
ttgtctaata gaatggatca catctctgct aataaaaaca ctacactggc agggtacaat   2460
tataatcatt aactgtgcct ggaatttgca gcagcagcca ccagaggtac cagtgccctt   2520
taagggttca taatttagaa taatccaatt atctgagttt ttcagggact gaggggtttg   2580
gcaaggtgta gaactttcag taataaagtc aagaaagtcc tggacaaacc aaggtagttg   2640
gtcactctag tccataacca ggtaaagagc tttccctgta acctgtgtaa ggttttagaa   2700
tcatttcttt ccttattacc aaaaatcctc cccaaatttt caagaaatta tgaactaaat   2760
agttactcta tgagatagga gttcagccca aagaaacac cataagaaca aatataattc    2820
ttgcttatgt taaccatgca atgaagcaga gagaaaaagt cagtggcctc tttaggagga   2880
ctgtagtgtg ggaagaaata actaaactgg gtttcaatcc tggcctggcc aggatctgga   2940
gcaagtgagt taatctttct aagccttgag tagtttataa aagaatggcc actccataga   3000
cagagtagcc tgaaccttga gttcttctat aaagtcacta tgaatttata ctcatttga   3060 aagtgggtgt caatatgtct gtccactttg cacagctgtt atgtggacaa aaggagatct   3120
gtgtgaaagt gtaacacaga gcctaaacta taacaggtaa gcaacacagt tgtccct     3177
```

<210> SEQ ID NO 23
<211> LENGTH: 20
<212> TYPE: PRT
<213> ORGANISM: Homo sapiens

<400> SEQUENCE: 23

Asp Leu Tyr Glu Glu Gly Gly Gly Gly Gly Gly Glu Gly Glu Asp Asn
1               5                   10                  15

Ala Asp Ser Lys
            20

<210> SEQ ID NO 24
<211> LENGTH: 4725
<212> TYPE: DNA
<213> ORGANISM: Homo sapiens

<400> SEQUENCE: 24

```
tgccgggatc caggtctccg ggtccgcttt ggccagagg cgcggaagga agcagtgccc     60
ggcgacactg cacccatccc ggctgctttt gctgcgccct ctcagcttcc caagaaaggc    120
atcgtcatgt gatcatcacc taagaactag aacatcagca ggccctagaa gcctcactct    180 tgccctccc tttaatatct caaaggatga cacttctgtg gtgtgtagtg agtctctact     240
tttatggaat cctgcaaagt gatgcctcag aacgctgcga tgactgggga ctagacacca    300
tgaggcaaat ccaagtgttt gaagatgagc cagctcgcat caagtgccca ctctttgaac   360
```

-continued

| | |
|---|---|
| acttcttgaa attcaactac agcacagccc attcagctgg ccttactctg atctggtatt | 420 |
| ggactaggca ggaccgggac cttgaggagc caattaactt ccgcctcccc gagaaccgca | 480 |
| ttagtaagga gaaagatgtg ctgtggttcc ggcccactct cctcaatgac actggcaact | 540 |
| atacctgcat gttaaggaac actacatatt gcagcaaagt tgcatttccc ttggaagttg | 600 |
| ttcaaaaaga cagctgtttc aattccccca tgaaactccc agtgcataaa ctgtatatag | 660 |
| aatatggcat tcagaggatc acttgtccaa atgtagatgg atattttcct tccagtgtca | 720 |
| aaccgactat cacttggtat atgggctgtt ataaaataca gaattttaat aatgtaatac | 780 |
| ccgaaggtat gaacttgagt ttcctcattg ccttaatttc aaataatgga aattacacat | 840 |
| gtgttgttac atatccagaa aatggacgta cgtttcatct caccaggact ctgactgtaa | 900 |
| aggtagtagg ctctccaaaa aatgcagtgc cccctgtgat ccattcacct aatgatcatg | 960 |
| tggtctatga gaaagaacca ggagaggagc tactcattcc ctgtacggtc tatttttagtt | 1020 |
| ttctgatgga ttctcgcaat gaggtttggt ggaccattga tggaaaaaaa cctgatgaca | 1080 |
| tcactattga tgtcaccatt aacgaaagta taagtcatag tagaacagaa gatgaaacaa | 1140 |
| gaactcagat tttgagcatc aagaaagtta cctctgagga tctcaagcgc agctatgtct | 1200 |
| gtcatgctag aagtgccaaa ggcgaagttc caaagcagcc aaggtgaagc agaaagtgcc | 1260 |
| agctccaaga tacacagtgg aactggcttg tggttttgga gccacagtcc tgctagtggt | 1320 |
| gattctcatt gttgtttacc atgtttactg gctagagatg gtcctatttt accgggctca | 1380 |
| ttttggaaca gatgaaacca ttttagatgg aaaagagtat gatatttatg tatcctatgc | 1440 |
| aaggaatgcg gaagaagaag aatttgtatt actgaccctc cgtggagttt tggagaatga | 1500 |
| atttggatac aagctgtgca tctttgaccg agacagtctg cctgggggaa ttgtcacaga | 1560 |
| tgagactttg agcttcattc agaaaagcag acgcctcctg gttgttctaa gccccaacta | 1620 |
| cgtgctccag ggaacccaag ccctcctgga gctcaaggct ggcctagaaa atatggcctc | 1680 |
| tcggggcaac atcaacgtca ttttagtaca gtacaaagct gtgaaggaaa cgaaggtgaa | 1740 |
| agagctgaag agggctaaga cggtgctcac ggtcattaaa tggaaagggg aaaaatccaa | 1800 |
| gtatccacag ggcaggttct ggaagcagct gcaggtggcc atgccagtga agaaaagtcc | 1860 |
| caggcggtct agcagtgatg agcagggcct ctcgtattca tctttgaaaa atgtatgaaa | 1920 |
| ggaataatga aaagggtaaa aagaacaagg ggtgctccag gaagaaagag tcccccccagt | 1980 |
| cttcattcgc agtttatggt ttcataggca aaaataatgg tctaagcctc ccaatagggga | 2040 |
| taaatttagg gtgactgtgt ggctgactat tctgcttcct caggcaacac taaagtttag | 2100 |
| aaagatatca tcaacgttct gtcaccagtc tctgatgcca ctatgttctt tgcaggcaaa | 2160 |
| gacttgttca atgcgaattt cccccttctac attgtctatc cctgttttta tatgtctcca | 2220 |
| ttcttttttaa aatcttaaca tatggagcag cctttcctat gaatttaaat atgcctttaa | 2280 |
| aataagtcac tgttgacagg gtcatgagtt tccgagtata gttttctttt tatcttattt | 2340 |
| ttactcgtcc gttgaaaaga taatcaaggc ctacatttta gctgaggata atgaacttt | 2400 |
| ttcctcattc ggctgtataa tacataacca cagcaagact gacatccact taggatgata | 2460 |
| caaagcagtg taactgaaaa tgtttctttt aattgattta aaggacttgt cttctatacc | 2520 |
| acccttgtcc tcatctcagg taatttatga aatctatgta aacttgaaaa atatttctta | 2580 |
| attttttgttt ttgctccagt caattcctga ttatccacag gtcaacccac attttttcat | 2640 |
| tccttctccc tatctgctta tatcgcattg ctcatttaga gtttgcagga ggctccatac | 2700 |

```
taggttcagt ctgaaagaaa tctcctaatg gtgctataga gagggaggta acagaaagac    2760
tcttttaggg cattttttctg actcatgaaa agagcacaga aaaggatgtt tggcaatttg    2820
tcttttaagt cttaaccttg ctaatgtgaa tactgggaaa gtgatttttt ctcactcgtt    2880
tttgttgctc cattgtaaag ggcggaggtc agtcttagtg gccttgagag ttgcttttgg    2940
cattaatatt ctaagagaat taactgtatt tcctgtcacc tattcactag tgcaggaaat    3000
atacttgctc caaataagtc agtatgagaa gtcactgtca atgaaagttg ttttgtttgt    3060
tttcagtaat attttgctgt ttttaagact tggaaaacta agtgcagagt ttacagagtg    3120
gtaaatatct atgttacatg tagattatac atatatatac acgtgtat atgagatata    3180 tatcttatat ctccacaaac acaaattata tatacata tccacacaca tacattacat    3240
atatctgtgt atataaatcc acatgcacat gaaatatata tatatatata atttgtgtgt    3300
gtgtatgtgt atgtatatga ctttaaatag ctatgggtac aatattaaaa accactggaa    3360
ctcttgtcca gttttttaaat tatgttttta ctggaatgtt tttgtgtcag tgtttttctgt    3420 acatattatt tgttaattca cagctcacag agtgatagtt gtcatagttc ttgccttccc    3480
taagtttata taaataactt aagtattgct acagtttatc taggttgcag tggcatctgc    3540
tgtgcacaga gcttccatgg tcactgctaa gcagtagcca gccatcgggc attaattgat    3600
ttcctactat attcccagca gacacattta gaaactaagc tatgttaacc tcagtgctca    3660
actatttgaa ctgttgagtg ataaaggaaa caaatataac tgtaaatgaa tcttggtatc    3720
ctgtgaaaca gaataattcg taatttaaga aagcccttat cccggtaaca tgaatgttga    3780
tgaacaaatg taaaattata tcctatattt aagtacccat aataaatcat ttccctctat    3840
aagtgttatt gattatttta aattgaaaaa agtttcactt ggatgaaaaa agtagaaaag    3900
taggtcattc ttggatctac tttttttttag ccttattaat atttttccct attagaaacc    3960
acaattactc cctctattaa cccttcactt actagaccag aaaagaactt attccagata    4020
agctttgaat atcaattctt acataaactt taggcaaaca gggaatagtc tagtcaccaa    4080
aggaccattc tcttgccaat gctgcattcc ttttgcactt ttggattcca tatttatccc    4140
aaatgctgtt gggcacccct agaaataacct tgatgttttt tctatttata tgcctgcctt    4200
tggtacttaa ttttacaaat gctgtaatat aaagcatatc aagtttatgt gatacgtatc    4260
attgcaagag aatttgtttc aagatttttt tttaatgttc cagaagatgg ccaatagaga    4320
acattcaagg gaaatgggga aacataattt agagaacaag aacaaaccat gtctcaaatt    4380
tttttaaaaa aaattaatgg ttttaaatat atgctatagg gacgttccat gcccaggtta    4440
acaaagaact gtgatatata gagtgtctaa ttacaaaatc atatacgatt tatttaattc    4500
tcttctgtat tgtaacttag atgattccca aggactctaa taaaaaatca cttcattgta    4560
tttggaaaca aaaacatcat tcattaatta cttattttct ttccataggt tttaatatt    4620 tgagagtgtc ttttttatttt cattcatgaa cttttgtatt tttcattttt catttgattt    4680
gtaaatttac ttatgttaaa aataaaccat ttattttcag ctttg                    4725
```

<210> SEQ ID NO 25
<211> LENGTH: 570
<212> TYPE: PRT
<213> ORGANISM: Homo sapiens

<400> SEQUENCE: 25

```
Met Thr Leu Leu Trp Cys Val Val Ser Leu Tyr Phe Tyr Gly Ile Leu
1               5                   10                  15
```

-continued

```
Gln Ser Asp Ala Ser Glu Arg Cys Asp Asp Trp Gly Leu Asp Thr Met
         20                  25                  30
Arg Gln Ile Gln Val Phe Glu Asp Glu Pro Ala Arg Ile Lys Cys Pro
             35                  40                  45
Leu Phe Glu His Phe Leu Lys Phe Asn Tyr Ser Thr Ala His Ser Ala
 50                  55                  60
Gly Leu Thr Leu Ile Trp Tyr Trp Thr Arg Gln Asp Arg Asp Leu Glu
 65                  70                  75                  80
Glu Pro Ile Asn Phe Arg Leu Pro Glu Asn Arg Ile Ser Lys Glu Lys
                 85                  90                  95
Asp Val Leu Trp Phe Arg Pro Thr Leu Leu Asn Asp Thr Gly Asn Tyr
            100                 105                 110
Thr Cys Met Leu Arg Asn Thr Thr Tyr Cys Ser Lys Val Ala Phe Pro
            115                 120                 125
Leu Glu Val Val Gln Lys Asp Ser Cys Phe Asn Ser Pro Met Lys Leu
            130                 135                 140
Pro Val His Lys Leu Tyr Ile Glu Tyr Gly Ile Gln Arg Ile Thr Cys
145                 150                 155                 160
Pro Asn Val Asp Gly Tyr Phe Pro Ser Ser Val Lys Pro Thr Ile Thr
                165                 170                 175
Trp Tyr Met Gly Cys Tyr Lys Ile Gln Asn Phe Asn Asn Val Ile Pro
            180                 185                 190
Glu Gly Met Asn Leu Ser Phe Leu Ile Ala Leu Ile Ser Asn Asn Gly
            195                 200                 205
Asn Tyr Thr Cys Val Val Thr Tyr Pro Glu Asn Gly Arg Thr Phe His
210                 215                 220
Leu Thr Arg Thr Leu Thr Val Lys Val Val Gly Ser Pro Lys Asn Ala
225                 230                 235                 240
Val Pro Pro Val Ile His Ser Pro Asn Asp His Val Val Tyr Glu Lys
                245                 250                 255
Glu Pro Gly Glu Glu Leu Leu Ile Pro Cys Thr Val Tyr Phe Ser Phe
            260                 265                 270
Leu Met Asp Ser Arg Asn Glu Val Trp Trp Thr Ile Asp Gly Lys Lys
            275                 280                 285
Pro Asp Asp Ile Thr Ile Asp Val Thr Ile Asn Glu Ser Ile Ser His
            290                 295                 300
Ser Arg Thr Glu Asp Glu Thr Arg Thr Gln Ile Leu Ser Ile Lys Lys
305                 310                 315                 320
Val Thr Ser Glu Asp Leu Lys Arg Ser Tyr Val Cys His Ala Arg Ser
                325                 330                 335
Ala Lys Gly Glu Val Ala Lys Ala Ala Lys Val Lys Gln Lys Val Pro
            340                 345                 350
Ala Pro Arg Tyr Thr Val Glu Leu Ala Cys Gly Phe Gly Ala Thr Val
            355                 360                 365
Leu Leu Val Val Ile Leu Ile Val Val Tyr His Val Tyr Trp Leu Glu
            370                 375                 380
Met Val Leu Phe Tyr Arg Ala His Phe Gly Thr Asp Glu Thr Ile Leu
385                 390                 395                 400
Asp Gly Lys Glu Tyr Asp Ile Tyr Val Ser Tyr Ala Arg Asn Ala Glu
                405                 410                 415
Glu Glu Glu Phe Val Leu Leu Thr Leu Arg Gly Val Leu Glu Asn Glu
            420                 425                 430
Phe Gly Tyr Lys Leu Cys Ile Phe Asp Arg Asp Ser Leu Pro Gly Gly
```

```
                    435                 440                 445
Ile Val Thr Asp Glu Thr Leu Ser Phe Ile Gln Lys Ser Arg Arg Leu
    450                 455                 460

Leu Val Leu Ser Pro Asn Tyr Val Leu Gln Gly Thr Gln Ala Leu
465                 470                 475                 480

Leu Glu Leu Lys Ala Gly Leu Glu Asn Met Ala Ser Arg Gly Asn Ile
                485                 490                 495

Asn Val Ile Leu Val Gln Tyr Lys Ala Val Lys Glu Thr Lys Val Lys
                500                 505                 510

Glu Leu Lys Arg Ala Lys Thr Val Leu Thr Val Ile Lys Trp Lys Gly
                515                 520                 525

Glu Lys Ser Lys Tyr Pro Gln Gly Arg Phe Trp Lys Gln Leu Gln Val
                530                 535                 540

Ala Met Pro Val Lys Lys Ser Pro Arg Arg Ser Ser Ser Asp Glu Gln
545                 550                 555                 560

Gly Leu Ser Tyr Ser Ser Leu Lys Asn Val
                565                 570

<210> SEQ ID NO 26
<211> LENGTH: 2063
<212> TYPE: DNA
<213> ORGANISM: Homo sapiens

<400> SEQUENCE: 26
tgccgggatc caggtctccg gggtccgctt tggccagagg cgcggaagga agcagtgccc      60
ggcgacactg cacccatccc ggctgctttt gctgcgccct ctcagcttcc caagaaaggc     120
atcgtcatgt gatcatcacc taagaactag aacatcagca ggccctagaa gcctcactct     180
tgcccctccc tttaatatct caaaggatga cacttctgtg gtgtgtagtg agtctctact     240
tttatggaat cctgcaaagt gatgcctcag aacgctgcga tgactgggga ctagacacca     300
tgaggcaaat ccaagtgttt gaagatgagc cagctcgcat caagtgccca ctctttgaac     360
acttcttgaa attcaactac agcacagccc attcagctgg ccttactctg atctggtatt     420
ggactaggca ggaccgggac cttgaggagc caattaactt ccgcctcccc gagaaccgca     480
ttagtaagga gaaagatgtg ctgtggttcc ggcccactct cctcaatgac actggcaact     540
atacctgcat gttaaggaac actacatatt gcagcaaagt tgcatttccc ttggaagttg     600
ttcaaaaaga cagctgtttc aattccccca tgaaactccc agtgcataaa ctgtatatag     660
aatatggcat tcagaggatc acttgtccaa atgtagatgg atattttcct tccagtgtca     720
aaccgactat cacttggtat atgggctgtt ataaaataca gaattttaat aatgtaatac     780
ccgaaggtat gaacttgagt ttcctcattg ccttaatttc aaataatgga aattacacat     840
gtgttgttac atatccagaa aatggacgta cgtttcatct caccaggact ctgactgtaa     900
aggtagtagg ctctccaaaa aatgcagtgc cccctgtgat ccattcacct aatgatcatg     960
tggtctatga gaaagaacca ggagaggagc tactcattcc ctgtacggtc tattttagtt    1020
ttctgatgga ttctcgcaat gaggtttggt ggaccattga tggaaaaaaa cctgatgaca    1080
tcactattga tgtcaccatt aacgaaagta agtcatag tagaacagaa gatgaaacaa    1140
gaactcagat tttgagcatc aagaaagtta cctctgagga tctcaagcgc agctatgtct    1200
gtcatgctag aagtgccaaa ggcgaagttg ccaaagcagc caaggtgaag cagaaaggta    1260
atagatgcgg tcagtgatga atctctcagc tccaaattaa cattgtggtg aataaggaca    1320
aaaggagaga ttgagaacaa gagagctcca gcacctagcc cgacggcatc taacccatag    1380
```

-continued

```
taatgaatca aacttaaatg aaaaatatga agtttttcat ctatgtaaga tactcaaaat    1440
attgtttctg atattgttag taccgtaatg cccaaatgta gctaaaaaaa tcgacgtgag    1500
tacagtgaga cacaattttg tgtctgtaca attatgaaaa attaaaaaca aagaaaatat    1560
tcaaagctac caaagataga aaaaactggt agagccacat attgttggtg aattattaag    1620
acccttttaa aaatcattca tggtagagtt taagagtcat aaaaaagatt gcatcatctg    1680
acctaagact ttcggaattt ttcctgaaca ataacagaa agggaattat ataccttta     1740 atattattag aagcattatc tgtagttgta aaacattatt aatagcagcc atccaattgt    1800
atgcaactaa ttaaggtatt gaatgtttat tttccaaaaa tgcataatta taatattatt    1860
ttaaacacta tgtatcaata tttaagcagg tttataatat accagcagcc acaattgcta    1920
aaatgaaaat catttaaatt atgattttaa atggtataaa catgattcct atgttgatag    1980
tactatatta ttctacaata aatggaaatt ataaagcctt cttgtcagaa gtgctgctcc    2040
taaaaaaaaa aaaaaaaaaa aaa                                           2063
```

<210> SEQ ID NO 27
<211> LENGTH: 356
<212> TYPE: PRT
<213> ORGANISM: Homo sapiens

<400> SEQUENCE: 27

```
Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Gly Ser Pro Lys Asn Ala
225                 230                 235                 240

Val Pro Pro Val Ile His Ser Pro Asn Asp His Val Val Tyr Glu Lys
```

```
                    245                 250                 255
Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
        290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Gly Asn
            340                 345                 350

Arg Cys Gly Gln
        355

<210> SEQ ID NO 28
<211> LENGTH: 3589
<212> TYPE: DNA
<213> ORGANISM: Homo sapiens

<400> SEQUENCE: 28
cgcggacccg gccggcccag gcccgcgccc gccgcggccc tgagaggccc cggcaggtcc      60
cggcccggcg gcggcagcca tggccggggg gccgggcccg ggggagcccg cagcccccgg     120
cgcccagcac ttcttgtacg aggtgccgcc ctgggtcatg tgccgcttct acaaagtgat     180
ggacgccctg gagcccgccg actggtgcca gttcgccgcc ctgatcgtgc gcgaccagac     240
cgagctgcgg ctgtgcgagc gctccgggca gcgcacggcc agcgtcctgt ggccctggat     300
caaccgcaac gcccgtgtgg ccgacctcgt gcacatcctc acgcacctgc agctgctccg     360
tgcgcgggac atcatcacag cctggcaccc tcccgccccg cttccgtccc caggcaccac     420
tgccccgagg cccagcagca tccctgcacc cgccgaggcc gaggcctgga gccccggaa      480 gttgccatcc tcagcctcca ccttcctctc cccagctttt ccaggctccc agacccattc     540
agggcctgag ctcggcctgg tcccaagccc tgcttccctg tggcctccac cgccatctcc     600
agcccctcct tctaccaagc caggcccaga gagctcagtg tccctcctgc agggagcccg     660
cccctttccg ttttgctggc ccctctgtga gatttcccgg ggcacccaca acttctcgga     720
ggagctcaag atcggggagg gtggctttgg gtgcgtgtac cgggcggtga tgaggaacac     780
ggtgtatgct gtgaagaggc tgaaggagaa cgctgacctg gagtggactg cagtgaagca     840
gagcttcctg accgaggtgg agcagctgtc caggtttcgt cacccaaaca ttgtggactt     900
tgctggctac tgtgctcaga acggcttcta ctgcctggtg tacggcttcc tgcccaacgg     960
ctccctggag gaccgtctcc actgccagac ccaggcctgc ccacctctct cctggcctca    1020
gcgactggac atccttctgg gtacagcccg ggcaattcag tttctacatc aggacagccc    1080
cagcctcatc catggagaca tcaagagttc caacgtcctt ctggatgaga ggctgacacc    1140
caagctggga gactttggcc tggcccggtt cagccgcttt gccgggtcca gcccagcca    1200 gagcagcatg gtggcccgga cacagacagt gcggggcacc ctggcctacc tgcccgagga    1260
gtacatcaag acgggaaggc tggctgtgga cacggacacc ttcagctttg ggtggtagt    1320 gctagagacc ttggctggtc agagggctgt gaagacgcac ggtgccagga ccaagtatct    1380
gaaagacctg gtggaagagg aggctgagga ggctggagtg gctttgagaa gcacccagag   1440
```

```
cacactgcaa gcaggtctgg ctgcagatgc ctgggctgct cccatcgcca tgcagatcta    1500
caagaagcac ctggacccca ggcccgggcc ctgcccacct gagctgggcc tgggcctggg    1560
ccagctggcc tgctgctgcc tgcaccgccg ggccaaaagg aggcctccta tgacccaggt    1620
gtacgagagg ctagagaagc tgcaggcagt ggtggcgggg gtgcccgggc attcggaggc    1680
cgccagctgc atccccccctt ccccgcagga gaactcctac gtgtccagca ctggcagagc    1740
ccacagtggg gctgctccat ggcagcccct ggcagcgcca tcaggagcca gtgcccaggc    1800
agcagagcag ctgcagagag ccccaaccca gcccgtggag agtgacgaga gcctaggcgg    1860
cctctctgct gccctgcgct cctggcactt gactccaagc tgccctctgg acccagcacc    1920
cctcagggag gccggctgtc ctcaggggga cacggcagga aatcgagct gggggagtgg    1980 cccaggatcc cggcccacag ccgtggaagg actggcccctt ggcagctctg catcatcgtc    2040
gtcagagcca ccgcagatta tcatcaaccc tgcccgacag aagatggtcc agaagctggc    2100
cctgtacgag gatggggccc tggacagcct gcagctgctg tcgtccagct ccctcccagg    2160
cttgggcctg aacaggaca ggcaggggcc cgaagaaagt gatgaatttc agagctgatg    2220
tgttcacctg ggcagatccc ccaaatccgg aagtcaaagt tctcatggtc agaagttctc    2280
atggtgcacg agtcctcagc actctgccgg cagtgggggt gggggcccat gcccgcgggg    2340
gagagaagga ggtggccctg ctgttctagg ctctgtgggc ataggcaggc agagtggaac    2400
cctgcctcca tgccagcatc tgggggcaag gaaggctggc atcatccagt gaggaggctg    2460
gcgcatgttg ggaggctgct ggctgcacag acccgtgagg ggaggagagg ggctgctgtg    2520
caggggtgtg gagtagggag ctggctcccc tgagagccat gcagggcgtc tgcagcccag    2580
gcctctggca gcagctcttt gcccatctct ttggacagtg ccaccctgc acaatggggc    2640 cgacgaggcc tagggccctc ctacctgctt acaatttgga aaagtgtggc cgggtgcggt    2700
ggctcacgcc tgtaatccca gcactttggg aggccaaggc aggaggatcg ctggagccca    2760
gtaggtcaag accagccagg gcaacatgat gagaccctgt ctctgccaaa aaattttta    2820 aactattagc ctggcgtggt agcgcacgcc tgtggtccca gctgctgggg aggctgaagt    2880
aggaggatca tttatgcttg ggaggtcgag gctgcagtga gtcatgattg tatgactgca    2940
ctccagcctg ggtgacagag caagaccctg tttcaaaaag aaaaaccctg ggaaaagtga    3000
agtatggctg taagtctcat ggttcagtcc tagcaagaag cgagaattct gagatcctcc    3060
agaaagtcga gcagcaccca cctccaacct cgggccagtg tcttcaggct ttactgggga    3120
cctgcgagct ggcctaatgt ggtggcctgc aagccaggcc atccctgggc ccacagacg    3180 agctccgagc caggtcaggc ttcggaggcc acaagctcag cctcaggccc aggcactgat    3240
tgtggcagag gggccactac ccaaggtcta gctaggccca agacctagtt acccagacag    3300
tgagaagccc ctggaaggca gaaaagttgg gagcatggca gacagggaag ggaaacattt    3360
tcagggaaaa gacatgtatc acatgtcttc agaagcaagt caggtttcat gtaaccgagt    3420
gtcctcttgc gtgtccaaaa gtagcccagg gctgtagcac aggcttcaca gtgattttgt    3480
gttcagccgt gagtcacact acatgccccc gtgaagctgg gcattggtga cgtccaggtt    3540
gtccttgagt aataaaaacg tatgttgcaa taaaaaaaaa aaaaaaaaa                 3589
```

<210> SEQ ID NO 29
<211> LENGTH: 712
<212> TYPE: PRT
<213> ORGANISM: Homo sapiens

<400> SEQUENCE: 29

```
Met Ala Gly Gly Pro Gly Pro Gly Glu Pro Ala Ala Pro Gly Ala Gln
1               5                   10                  15

His Phe Leu Tyr Glu Val Pro Pro Trp Val Met Cys Arg Phe Tyr Lys
            20                  25                  30

Val Met Asp Ala Leu Glu Pro Ala Asp Trp Cys Gln Phe Ala Ala Leu
        35                  40                  45

Ile Val Arg Asp Gln Thr Glu Leu Arg Leu Cys Glu Arg Ser Gly Gln
    50                  55                  60

Arg Thr Ala Ser Val Leu Trp Pro Trp Ile Asn Arg Asn Ala Arg Val
65                  70                  75                  80

Ala Asp Leu Val His Ile Leu Thr His Leu Gln Leu Arg Ala Arg
                85                  90                  95

Asp Ile Ile Thr Ala Trp His Pro Pro Ala Pro Leu Pro Ser Pro Gly
                100                 105                 110

Thr Thr Ala Pro Arg Pro Ser Ser Ile Pro Ala Pro Ala Glu Ala Glu
            115                 120                 125

Ala Trp Ser Pro Arg Lys Leu Pro Ser Ser Ala Ser Thr Phe Leu Ser
        130                 135                 140

Pro Ala Phe Pro Gly Ser Gln Thr His Ser Gly Pro Glu Leu Gly Leu
145                 150                 155                 160

Val Pro Ser Pro Ala Ser Leu Trp Pro Pro Pro Ser Pro Ala Pro
                165                 170                 175

Ser Ser Thr Lys Pro Gly Pro Glu Ser Ser Val Ser Leu Leu Gln Gly
            180                 185                 190

Ala Arg Pro Phe Pro Phe Cys Trp Pro Leu Cys Glu Ile Ser Arg Gly
        195                 200                 205

Thr His Asn Phe Ser Glu Glu Leu Lys Ile Gly Glu Gly Gly Phe Gly
210                 215                 220

Cys Val Tyr Arg Ala Val Met Arg Asn Thr Val Tyr Ala Val Lys Arg
225                 230                 235                 240

Leu Lys Glu Asn Ala Asp Leu Glu Trp Thr Ala Val Lys Gln Ser Phe
                245                 250                 255

Leu Thr Glu Val Glu Gln Leu Ser Arg Phe Arg His Pro Asn Ile Val
            260                 265                 270

Asp Phe Ala Gly Tyr Cys Ala Gln Asn Gly Phe Tyr Cys Leu Val Tyr
            275                 280                 285

Gly Phe Leu Pro Asn Gly Ser Leu Glu Asp Arg Leu His Cys Gln Thr
        290                 295                 300

Gln Ala Cys Pro Pro Leu Ser Trp Pro Gln Arg Leu Asp Ile Leu Leu
305                 310                 315                 320

Gly Thr Ala Arg Ala Ile Gln Phe Leu His Gln Asp Ser Pro Ser Leu
                325                 330                 335

Ile His Gly Asp Ile Lys Ser Ser Asn Val Leu Leu Asp Glu Arg Leu
            340                 345                 350

Thr Pro Lys Leu Gly Asp Phe Gly Leu Ala Arg Phe Ser Arg Phe Ala
        355                 360                 365

Gly Ser Ser Pro Ser Gln Ser Ser Met Val Ala Arg Thr Gln Thr Val
370                 375                 380

Arg Gly Thr Leu Ala Tyr Leu Pro Glu Glu Tyr Ile Lys Thr Gly Arg
385                 390                 395                 400

Leu Ala Val Asp Thr Asp Thr Phe Ser Phe Gly Val Val Val Leu Glu
                405                 410                 415
```

```
Thr Leu Ala Gly Gln Arg Ala Val Lys Thr His Gly Ala Arg Thr Lys
            420                 425                 430
Tyr Leu Lys Asp Leu Val Glu Glu Ala Glu Ala Gly Val Ala
        435                 440                 445
Leu Arg Ser Thr Gln Ser Thr Leu Gln Ala Gly Leu Ala Ala Asp Ala
    450                 455                 460
Trp Ala Ala Pro Ile Ala Met Gln Ile Tyr Lys Lys His Leu Asp Pro
465                 470                 475                 480
Arg Pro Gly Pro Cys Pro Pro Glu Leu Gly Leu Gly Leu Gly Gln Leu
                485                 490                 495
Ala Cys Cys Cys Leu His Arg Arg Ala Lys Arg Arg Pro Pro Met Thr
            500                 505                 510
Gln Val Tyr Glu Arg Leu Glu Lys Leu Gln Ala Val Val Ala Gly Val
        515                 520                 525
Pro Gly His Ser Glu Ala Ala Ser Cys Ile Pro Pro Ser Pro Gln Glu
    530                 535                 540
Asn Ser Tyr Val Ser Ser Thr Gly Arg Ala His Ser Gly Ala Ala Pro
545                 550                 555                 560
Trp Gln Pro Leu Ala Ala Pro Ser Gly Ala Ser Ala Gln Ala Ala Glu
                565                 570                 575
Gln Leu Gln Arg Gly Pro Asn Gln Pro Val Glu Ser Asp Glu Ser Leu
            580                 585                 590
Gly Gly Leu Ser Ala Ala Leu Arg Ser Trp His Leu Thr Pro Ser Cys
        595                 600                 605
Pro Leu Asp Pro Ala Pro Leu Arg Glu Ala Gly Cys Pro Gln Gly Asp
    610                 615                 620
Thr Ala Gly Glu Ser Ser Trp Gly Ser Gly Pro Gly Ser Arg Pro Thr
625                 630                 635                 640
Ala Val Glu Gly Leu Ala Leu Gly Ser Ala Ser Ser Ser Glu
                645                 650                 655
Pro Pro Gln Ile Ile Ile Asn Pro Ala Arg Gln Lys Met Val Gln Lys
            660                 665                 670
Leu Ala Leu Tyr Glu Asp Gly Ala Leu Asp Ser Leu Gln Leu Leu Ser
        675                 680                 685
Ser Ser Ser Leu Pro Gly Leu Gly Leu Glu Gln Asp Arg Gln Gly Pro
    690                 695                 700
Glu Glu Ser Asp Glu Phe Gln Ser
705                 710

<210> SEQ ID NO 30
<211> LENGTH: 3499
<212> TYPE: DNA
<213> ORGANISM: Homo sapiens

<400> SEQUENCE: 30
cgcggacccg gccggcccag gcccgcgccc gccgcggccc tgagaggccc cggcaggtcc      60
cggcccggcg gcggcagcca tggccggggg gccgggcccg ggggagcccg cagcccccgg     120
cgcccagcac ttcttgtacg aggtgccgcc ctgggtcatg tgccgcttct acaaagtgat     180
ggacgccctg gagcccgccg actggtgcca gttcgccgcc ctgatcgtgc gcgaccagac     240
cgagctgcgg ctgtgcgagc gctccgggca gcgcacggcc agcgtcctgt ggccctggat     300
caaccgcaac gcccgtgtgg ccgacctcgt gcacatcctc acgcacctgc agctgctccg     360
tgcgcgggac atcatcacag cctggcaccc tcccgccccg cttccgtccc caggcaccac     420
```

```
tgccccgagg cccagcagca tccctgcacc cgccgaggcc gaggcctgga gccccggaa    480 gttgccatcc tcagcctcca ccttcctctc cccagctttt ccaggctccc agacccattc    540
agggcctgag ctcggcctgg tcccaagccc tgcttccctg tggcctccac cgccatctcc    600
agccccttct tctaccaagc caggcccaga gagctcagtg tccctcctgc agggagcccg    660 ccccttccg ttttgctggc ccctctgtga gatttcccgg ggcacccaca acttctcgga    720
ggagctcaag atcggggagg gtggcttttgg gtgcgtgtac cgggcggtga tgaggaacac    780
ggtgtatgct gtgaagaggc tgaaggagaa cgctgacctg gagtggactg cagtgaagca    840
gagcttcctg accgaggtgg agcagctgtc caggtttcgt cacccaaaca ttgtggactt    900
tgctggctac tgtgctcaga acggcttcta ctgcctggtg tacggcttcc tgcccaacgg    960
ctccctggag gaccgtctcc actgccagac ccaggcctgc ccacctctct cctggcctca   1020
gcgactggac atccttctgg gtacagcccg ggcaattcag tttctacatc aggacagccc   1080
cagcctcatc catggagaca tcaagagttc aacgtccttc tggatgaga ggctgacacc    1140 caagctggga gactttggcc tggcccgtt cagccgcttt gccgggtcca gcccagcca   1200 gagcagcatg gtggcccgga cacagacagt gcggggcacc ctggcctacc tgcccgagga   1260
gtacatcaag acgggaaggc tggctgtgga cacggacacc ttcagctttg gggtggtagt   1320
gctagagacc ttggctggtc agagggctgt gaagacgcac ggtgccagga ccaagtatct   1380
gaaagacctg gtggaagagg aggctgagga ggctggagtg gctttgagaa gcacccagag   1440
cacactgcaa gcaggtctgg ctgcagatgc ctgggctgct cccatcgcca tgcagatcta   1500
caagaagcac ctggaccca ggcccgggcc ctgcccacct gagctgggcc tgggcctggg   1560
ccagctggcc tgctgctgcc tgcaccgccg ggccaaaagg aggcctccta tgacccagga   1620
gaactcctac gtgtccagca ctggcagagc ccacagtggg gctgctccat ggcagccct   1680 ggcagcgcca tcaggagcca gtgcccaggc agcagagcag ctgcagagag gccccaacca   1740
gcccgtggag agtgacgaga gcctaggcgg cctctctgct gccctgcgct cctggcactt   1800
gactccaagc tgccctctgg acccagcacc cctcagggag gccggctgtc ctcaggggga   1860
cacggcagga gaatcgagct gggggagtgg cccaggatcc cggcccacag ccgtggaagg   1920
actggccctt ggcagctctg catcatcgtc gtcagagcca ccgcagatta tcatcaaccc   1980
tgcccgacag aagatggtcc agaagctggc cctgtacgag gatggggccc tggacagcct   2040
gcagctgctg tcgtccagct ccctcccagg cttgggcctg gaacaggaca ggcaggggcc   2100
cgaagaaagt gatgaatttc agagctgatg tgttcacctg gcagatccc ccaaatccgg    2160 aagtcaaagt tctcatggtc agaagttctc atggtgcacg agtcctcagc actctgccgg   2220 cagtggggt gggggcccat gcccgcgggg gagagaagga ggtggccctg ctgttctagg   2280
ctctgtgggc ataggcaggc agagtggaac cctgcctcca tgccagcatc tgggggcaag   2340
gaaggctggc atcatccagt gaggaggctg gcgcatgttg ggaggctgct ggctgcacag   2400
acccgtgagg ggaggagagg ggctgctgtg caggggtgtg gagtagggag ctggctcccc   2460
tgagagccat gcagggcgtc tgcagcccag gcctctggca gcagctcttt gcccatctct   2520
ttggacagtg gccaccctgc acaatggggc gacgaggcc tagggccctc ctacctgctt    2580
acaatttgga aaagtgtggc cgggtgcggt ggctcacgcc tgtaatccca gcactttggg   2640
aggccaaggc aggaggatcg ctggagccca gtaggtcaag accagccagg caacatgat    2700 gagaccctgt ctctgccaaa aaattttta aactattagc ctggcgtggt agcgcacgcc   2760
tgtggtccca gctgctgggg aggctgaagt aggaggatca tttatgcttg ggaggtcgag   2820
```

```
gctgcagtga gtcatgattg tatgactgca ctccagcctg ggtgacagag caagaccctg    2880
tttcaaaaag aaaaaccctg ggaaaagtga agtatggctg taagtctcat ggttcagtcc    2940
tagcaagaag cgagaattct gagatcctcc agaaagtcga gcagcaccca cctccaacct    3000
cgggccagtg tcttcaggct ttactgggga cctgcgagct ggcctaatgt ggtggcctgc    3060
aagccaggcc atccctgggc gccacagacg agctccgagc caggtcaggc ttcggaggcc    3120
acaagctcag cctcaggccc aggcactgat tgtggcagag gggccactac ccaaggtcta    3180
gctaggccca agacctagtt acccagacag tgagaagccc ctggaaggca gaaaagttgg    3240
gagcatggca gacagggaag ggaaacattt tcagggaaaa gacatgtatc acatgtcttc    3300
agaagcaagt caggtttcat gtaaccgagt gtcctcttgc gtgtccaaaa gtagcccagg    3360
gctgtagcac aggcttcaca gtgattttgt gttcagccgt gagtcacact acatgccccc    3420
gtgaagctgg gcattggtga cgtccaggtt gtccttgagt aataaaaacg tatgttgcaa    3480
taaaaaaaaa aaaaaaaa                                                  3499
```

<210> SEQ ID NO 31
<211> LENGTH: 682
<212> TYPE: PRT
<213> ORGANISM: Homo sapiens

<400> SEQUENCE: 31

```
Met Ala Gly Gly Pro Gly Pro Gly Glu Pro Ala Ala Pro Gly Ala Gln
1               5                   10                  15

His Phe Leu Tyr Glu Val Pro Pro Trp Val Met Cys Arg Phe Tyr Lys
            20                  25                  30

Val Met Asp Ala Leu Glu Pro Ala Asp Trp Cys Gln Phe Ala Ala Leu
        35                  40                  45

Ile Val Arg Asp Gln Thr Glu Leu Arg Leu Cys Glu Arg Ser Gly Gln
    50                  55                  60

Arg Thr Ala Ser Val Leu Trp Pro Trp Ile Asn Arg Asn Ala Arg Val
65                  70                  75                  80

Ala Asp Leu Val His Ile Leu Thr His Leu Gln Leu Leu Arg Ala Arg
                85                  90                  95

Asp Ile Ile Thr Ala Trp His Pro Ala Pro Leu Pro Ser Pro Gly
            100                 105                 110

Thr Thr Ala Pro Arg Pro Ser Ser Ile Pro Ala Pro Glu Ala Glu
        115                 120                 125

Ala Trp Ser Pro Arg Lys Leu Pro Ser Ser Ala Ser Thr Phe Leu Ser
    130                 135                 140

Pro Ala Phe Pro Gly Ser Gln Thr His Ser Gly Pro Glu Leu Gly Leu
145                 150                 155                 160

Val Pro Ser Pro Ala Ser Leu Trp Pro Pro Pro Ser Pro Ala Pro
                165                 170                 175

Ser Ser Thr Lys Pro Gly Pro Glu Ser Ser Val Ser Leu Leu Gln Gly
            180                 185                 190

Ala Arg Pro Phe Pro Phe Cys Trp Pro Leu Cys Glu Ile Ser Arg Gly
        195                 200                 205

Thr His Asn Phe Ser Glu Glu Leu Lys Ile Gly Glu Gly Gly Phe Gly
    210                 215                 220

Cys Val Tyr Arg Ala Val Met Arg Asn Thr Val Tyr Ala Val Lys Arg
225                 230                 235                 240

Leu Lys Glu Asn Ala Asp Leu Glu Trp Thr Ala Val Lys Gln Ser Phe
```

-continued

```
                245                 250                 255
Leu Thr Glu Val Glu Gln Leu Ser Arg Phe Arg His Pro Asn Ile Val
            260                 265                 270
Asp Phe Ala Gly Tyr Cys Ala Gln Asn Gly Phe Tyr Cys Leu Val Tyr
            275                 280                 285
Gly Phe Leu Pro Asn Gly Ser Leu Glu Asp Arg Leu His Cys Gln Thr
            290                 295                 300
Gln Ala Cys Pro Pro Leu Ser Trp Pro Gln Arg Leu Asp Ile Leu Leu
305                 310                 315                 320
Gly Thr Ala Arg Ala Ile Gln Phe Leu His Gln Asp Ser Pro Ser Leu
                325                 330                 335
Ile His Gly Asp Ile Lys Ser Ser Asn Val Leu Leu Asp Glu Arg Leu
                340                 345                 350
Thr Pro Lys Leu Gly Asp Phe Gly Leu Ala Arg Phe Ser Arg Phe Ala
                355                 360                 365
Gly Ser Ser Pro Ser Gln Ser Ser Met Val Ala Arg Thr Gln Thr Val
            370                 375                 380
Arg Gly Thr Leu Ala Tyr Leu Pro Glu Glu Tyr Ile Lys Thr Gly Arg
385                 390                 395                 400
Leu Ala Val Asp Thr Asp Thr Phe Ser Phe Gly Val Val Leu Glu
                405                 410                 415
Thr Leu Ala Gly Gln Arg Ala Val Lys Thr His Gly Ala Arg Thr Lys
                420                 425                 430
Tyr Leu Lys Asp Leu Val Glu Glu Ala Glu Glu Ala Gly Val Ala
                435                 440                 445
Leu Arg Ser Thr Gln Ser Thr Leu Gln Ala Gly Leu Ala Ala Asp Ala
            450                 455                 460
Trp Ala Ala Pro Ile Ala Met Gln Ile Tyr Lys Lys His Leu Asp Pro
465                 470                 475                 480
Arg Pro Gly Pro Cys Pro Pro Glu Leu Gly Leu Gly Leu Gly Gln Leu
                485                 490                 495
Ala Cys Cys Cys Leu His Arg Arg Ala Lys Arg Arg Pro Pro Met Thr
                500                 505                 510
Gln Glu Asn Ser Tyr Val Ser Ser Thr Gly Arg Ala His Ser Gly Ala
            515                 520                 525
Ala Pro Trp Gln Pro Leu Ala Ala Pro Ser Gly Ala Ser Ala Gln Ala
            530                 535                 540
Ala Glu Gln Leu Gln Arg Gly Pro Asn Gln Pro Val Glu Ser Asp Glu
545                 550                 555                 560
Ser Leu Gly Gly Leu Ser Ala Ala Leu Arg Ser Trp His Leu Thr Pro
                565                 570                 575
Ser Cys Pro Leu Asp Pro Ala Pro Leu Arg Glu Ala Gly Cys Pro Gln
                580                 585                 590
Gly Asp Thr Ala Gly Glu Ser Ser Trp Gly Ser Gly Pro Gly Ser Arg
                595                 600                 605
Pro Thr Ala Val Glu Gly Leu Ala Leu Gly Ser Ser Ala Ser Ser Ser
            610                 615                 620
Ser Glu Pro Pro Gln Ile Ile Asn Pro Ala Arg Gln Lys Met Val
625                 630                 635                 640
Gln Lys Leu Ala Leu Tyr Glu Asp Gly Ala Leu Asp Ser Leu Gln Leu
                645                 650                 655
Leu Ser Ser Ser Leu Pro Gly Leu Gly Leu Glu Gln Asp Arg Gln
                660                 665                 670
```

Gly Pro Glu Glu Ser Asp Glu Phe Gln Ser
        675                 680

<210> SEQ ID NO 32
<211> LENGTH: 3352
<212> TYPE: DNA
<213> ORGANISM: Homo sapiens

<400> SEQUENCE: 32

| | | | | | |
|---|---|---|---|---|---|
| cgcggacccg | gccggcccag | gcccgcgccc | gccgcggccc | tgagaggccc | cggcaggtcc | 60 |
| cggcccggcg | gcggcagcca | tggcggggg | gccgggcccg | ggggagcccg | cagcccccgg | 120 |
| cgcccagcac | ttcttgtacg | aggtgccgcc | ctgggtcatg | tgccgcttct | acaaagtgat | 180 |
| ggacgccctg | gagcccgccg | actggtgcca | gttcgccgcc | ctgatcgtgc | gcgaccagac | 240 |
| cgagctgcgg | ctgtgcgagc | gctccgggca | gcgcacggcc | agcgtcctgt | ggccctggat | 300 |
| caaccgcaac | gcccgtgtgg | ccgacctcgt | gcacatcctc | acgcacctgc | agctgctccg | 360 |
| tgcgcgggac | atcatcacag | cctggcaccc | tcccgccccg | cttccgtccc | caggcaccac | 420 |
| tgccccgagg | cccagcagca | tccctgcacc | cgccgaggcc | gaggcctgga | gcccccggaa | 480 |
| gttgccatcc | tcagcctcca | ccttcctctc | cccagctttt | ccaggctccc | agacccattc | 540 |
| agggcctgag | ctcggcctgg | tcccaagccc | tgcttccctg | tggcctccac | gccatctcc | 600 |
| agccccttct | tctaccaagc | caggcccaga | gagctcagtg | tccctcctgc | agggagcccg | 660 |
| ccccttttccg | ttttgctggc | ccctctgtga | gatttcccgg | ggcacccaca | acttctcgga | 720 |
| ggagctcaag | atcggggagg | gtggctttgg | gtgcgtgtac | cgggcggtga | tgaggaacac | 780 |
| ggtgtatgct | gtgaagaggc | tgaaggagaa | cgctgacctg | gagtggactg | cagtgaagca | 840 |
| gagcttcctg | accgaggtgg | agcagctgtc | caggtttcgt | cacccaaaca | ttgtggactt | 900 |
| tgctggctac | tgtgctcaga | acggcttcta | ctgcctggtg | tacggcttcc | tgcccaacgg | 960 |
| ctccctggag | gaccgtctcc | actgccagac | ccaggcctgc | ccacctctct | cctggcctca | 1020 |
| gcgactggac | atccttctgg | gtacagcccg | ggcaattcag | tttctacatc | aggacagccc | 1080 |
| cagcctcatc | catggagaca | tcaagagttc | aacgtccttc | tggatgagag | gctgacacc | 1140 |
| caagctggga | gactttggcc | tggcccggtt | cagccgcttt | gccgggtcca | gccccagcca | 1200 |
| gagcagcatg | gtgccccgga | cacagacagt | gcggggcacc | ctggcctacc | tgcccgagga | 1260 |
| gtacatcaag | acgggaaggc | tggctgtgga | cacggacacc | ttcagctttg | ggtggtagt | 1320 |
| gctagagacc | ttggctggtc | agagggctgt | gaagacgcac | ggtgccagga | ccaagtatct | 1380 |
| ggtgtacgag | aggctagaga | agctgcaggc | agtggtggcg | ggggtgcccg | gcattcgga | 1440 |
| ggccgccagc | tgcatccccc | cttccccgca | ggagaactcc | tacgtgtcca | gcactggcag | 1500 |
| agcccacagt | ggggctgctc | catggcagcc | cctggcagcg | ccatcaggag | ccagtgccca | 1560 |
| ggcagcagag | cagctgcaga | gaggcccaa | ccagcccgtg | gagagtgacg | agagcctagg | 1620 |
| cggcctctct | gctgccctgc | gctcctggca | cttgactcca | agctgccctc | tggacccagc | 1680 |
| acccctcagg | gaggccggct | gtcctcaggg | ggacacggca | ggagaatcga | gctggggag | 1740 |
| tggcccagga | tcccggccca | cagccgtgga | aggactggcc | cttggcagct | ctgcatcatc | 1800 |
| gtcgtcagag | ccaccgcaga | ttatcatcaa | ccctgcccga | cagaagatgg | tccagaagct | 1860 |
| ggccctgtac | gaggatgggg | ccctggacag | cctgcagctg | ctgtcgtcca | gctccctccc | 1920 |
| aggcttgggc | ctggaacagg | acaggcaggg | gcccgaagaa | agtgatgaat | tcagagctg | 1980 |
| atgtgttcac | ctgggcagat | ccccaaatc | cggaagtcaa | agttctcatg | gtcagaagtt | 2040 |

```
ctcatggtgc acgagtcctc agcactctgc cggcagtggg ggtgggggcc catgcccgcg      2100
ggggagagaa ggaggtggcc ctgctgttct aggctctgtg gcataggca ggcagagtgg       2160 aaccctgcct ccatgccagc atctgggggc aaggaaggct ggcatcatcc agtgaggagg      2220
ctggcgcatg ttgggaggct gctggctgca cagacccgtg aggggaggag aggggctgct      2280
gtgcaggggt gtggagtagg gagctggctc ccctgagagc catgcagggc gtctgcagcc      2340
caggcctctg gcagcagctc tttgcccatc tctttggaca gtggccaccc tgcacaatgg      2400
ggccgacgag gcctagggcc ctcctacctg cttacaattt ggaaaagtgt ggccgggtgc      2460
ggtggctcac gcctgtaatc ccagcacttt gggaggccaa ggcaggagga tcgctggagc      2520
ccagtaggtc aagaccagcc agggcaacat gatgagaccc tgtctctgcc aaaaaatttt      2580
ttaaactatt agcctggcgt ggtagcgcac gcctgtggtc ccagctgctg gggaggctga      2640
agtaggagga tcatttatgc ttgggaggtc gaggctgcag tgagtcatga ttgtatgact      2700
gcactccagc ctgggtgaca gagcaagacc ctgtttcaaa aagaaaaacc ctgggaaaag      2760
tgaagtatgg ctgtaagtct catggttcag tcctagcaag aagcgagaat tctgagatcc      2820
tccagaaagt cgagcagcac ccacctccaa cctcgggcca gtgtcttcag gctttactgg      2880
ggacctgcga gctggcctaa tgtggtggcc tgcaagccag gccatccctg ggcgccacag      2940
acgagctccg agccaggtca ggcttcggag gccacaagct cagcctcagg cccaggcact      3000
gattgtggca gaggggccac tacccaaggt ctagctaggc caagaccta gttacccaga       3060 cagtgagaag cccctggaag gcagaaaagt tgggagcatg gcagacaggg aagggaaaca      3120
ttttcaggga aaagacatgt atcacatgtc ttcagaagca agtcaggttt catgtaaccg      3180
agtgtcctct tgcgtgtcca aaagtagccc agggctgtag cacaggcttc acagtgattt      3240
tgtgttcagc cgtgagtcac actacatgcc cccgtgaagc tgggcattgg tgacgtccag      3300
gttgtccttg agtaataaaa acgtatgttg caataaaaaa aaaaaaaaaa aa              3352
```

<210> SEQ ID NO 33
<211> LENGTH: 633
<212> TYPE: PRT
<213> ORGANISM: Homo sapiens

<400> SEQUENCE: 33

Met Ala Gly Gly Pro Gly Pro Gly Glu Pro Ala Pro Gly Ala Gln
1               5                   10                  15

His Phe Leu Tyr Glu Val Pro Pro Trp Val Met Cys Arg Phe Tyr Lys
            20                  25                  30

Val Met Asp Ala Leu Glu Pro Ala Asp Trp Cys Gln Phe Ala Ala Leu
        35                  40                  45

Ile Val Arg Asp Gln Thr Glu Leu Arg Leu Cys Glu Arg Ser Gly Gln
    50                  55                  60

Arg Thr Ala Ser Val Leu Trp Pro Trp Ile Asn Arg Asn Ala Arg Val
65                  70                  75                  80

Ala Asp Leu Val His Ile Leu Thr His Leu Gln Leu Arg Ala Arg
                85                  90                  95

Asp Ile Ile Thr Ala Trp His Pro Pro Ala Pro Leu Pro Ser Pro Gly
            100                 105                 110

Thr Thr Ala Pro Arg Pro Ser Ser Ile Pro Ala Pro Ala Glu Ala Glu
        115                 120                 125

Ala Trp Ser Pro Arg Lys Leu Pro Ser Ser Ala Ser Thr Phe Leu Ser
    130                 135                 140

```
Pro Ala Phe Pro Gly Ser Gln Thr His Ser Gly Pro Glu Leu Gly Leu
145                 150                 155                 160

Val Pro Ser Pro Ala Ser Leu Trp Pro Pro Pro Ser Pro Ala Pro
                165                 170                 175

Ser Ser Thr Lys Pro Gly Pro Glu Ser Ser Val Ser Leu Leu Gln Gly
            180                 185                 190

Ala Arg Pro Phe Pro Phe Cys Trp Pro Leu Cys Glu Ile Ser Arg Gly
                195                 200                 205

Thr His Asn Phe Ser Glu Glu Leu Lys Ile Gly Glu Gly Gly Phe Gly
            210                 215                 220

Cys Val Tyr Arg Ala Val Met Arg Asn Thr Val Tyr Ala Val Lys Arg
225                 230                 235                 240

Leu Lys Glu Asn Ala Asp Leu Glu Trp Thr Ala Val Lys Gln Ser Phe
                245                 250                 255

Leu Thr Glu Val Glu Gln Leu Ser Arg Phe Arg His Pro Asn Ile Val
            260                 265                 270

Asp Phe Ala Gly Tyr Cys Ala Gln Asn Gly Phe Tyr Cys Leu Val Tyr
            275                 280                 285

Gly Phe Leu Pro Asn Gly Ser Leu Glu Asp Arg Leu His Cys Gln Thr
290                 295                 300

Gln Ala Cys Pro Pro Leu Ser Trp Pro Gln Arg Leu Asp Ile Leu Leu
305                 310                 315                 320

Gly Thr Ala Arg Ala Ile Gln Phe Leu His Gln Asp Ser Pro Ser Leu
                325                 330                 335

Ile His Gly Asp Ile Lys Ser Ser Asn Val Leu Leu Asp Glu Arg Leu
            340                 345                 350

Thr Pro Lys Leu Gly Asp Phe Gly Leu Ala Arg Phe Ser Arg Phe Ala
            355                 360                 365

Gly Ser Ser Pro Ser Gln Ser Ser Met Val Ala Arg Thr Gln Thr Val
370                 375                 380

Arg Gly Thr Leu Ala Tyr Leu Pro Glu Glu Tyr Ile Lys Thr Gly Arg
385                 390                 395                 400

Leu Ala Val Asp Thr Asp Thr Phe Ser Phe Gly Val Val Val Leu Glu
                405                 410                 415

Thr Leu Ala Gly Gln Arg Ala Val Lys Thr His Gly Ala Arg Thr Lys
            420                 425                 430

Tyr Leu Val Tyr Glu Arg Leu Glu Lys Leu Gln Ala Val Val Ala Gly
            435                 440                 445

Val Pro Gly His Ser Glu Ala Ala Ser Cys Ile Pro Pro Ser Pro Gln
450                 455                 460

Glu Asn Ser Tyr Val Ser Ser Thr Gly Arg Ala His Ser Gly Ala Ala
465                 470                 475                 480

Pro Trp Gln Pro Leu Ala Ala Pro Ser Gly Ala Ser Ala Gln Ala Ala
                485                 490                 495

Glu Gln Leu Gln Arg Gly Pro Asn Gln Pro Val Glu Ser Asp Glu Ser
            500                 505                 510

Leu Gly Gly Leu Ser Ala Ala Leu Arg Ser Trp His Leu Thr Pro Ser
            515                 520                 525

Cys Pro Leu Asp Pro Ala Pro Leu Arg Glu Ala Gly Cys Pro Gln Gly
            530                 535                 540

Asp Thr Ala Gly Glu Ser Ser Trp Gly Ser Gly Pro Gly Ser Arg Pro
545                 550                 555                 560
```

```
Thr Ala Val Glu Gly Leu Ala Leu Gly Ser Ser Ala Ser Ser Ser Ser
            565                 570                 575

Glu Pro Pro Gln Ile Ile Ile Asn Pro Ala Arg Gln Lys Met Val Gln
        580                 585                 590

Lys Leu Ala Leu Tyr Glu Asp Gly Ala Leu Asp Ser Leu Gln Leu Leu
    595                 600                 605

Ser Ser Ser Ser Leu Pro Gly Leu Gly Leu Glu Gln Asp Arg Gln Gly
610                 615                 620

Pro Glu Glu Ser Asp Glu Phe Gln Ser
625                 630

<210> SEQ ID NO 34
<211> LENGTH: 23
<212> TYPE: RNA
<213> ORGANISM: Homo sapiens

<400> SEQUENCE: 34
uguaaacauc cuacacucuc agc                                              23

<210> SEQ ID NO 35
<211> LENGTH: 21
<212> TYPE: RNA
<213> ORGANISM: Homo sapiens

<400> SEQUENCE: 35
uguaaacauc cuacacucag c                                                21

<210> SEQ ID NO 36
<211> LENGTH: 23
<212> TYPE: RNA
<213> ORGANISM: Homo sapiens

<400> SEQUENCE: 36
uguaaacauc cucgacugga agc                                              23

<210> SEQ ID NO 37
<211> LENGTH: 22
<212> TYPE: RNA
<213> ORGANISM: Homo sapiens

<400> SEQUENCE: 37
uggcucaguu cagcaggaac ag                                               22

<210> SEQ ID NO 38
<211> LENGTH: 22
<212> TYPE: RNA
<213> ORGANISM: Homo sapiens

<400> SEQUENCE: 38
uauggcuuuu cauuccuaug ug                                               22

<210> SEQ ID NO 39
<211> LENGTH: 20
<212> TYPE: RNA
<213> ORGANISM: Homo sapiens

<400> SEQUENCE: 39
ccucugggcc cuuccuccag                                                  20

<210> SEQ ID NO 40
<211> LENGTH: 22
<212> TYPE: RNA
```

```
<213> ORGANISM: Homo sapiens

<400> SEQUENCE: 40
uggacggaga acugauaagg gu                                            22

<210> SEQ ID NO 41
<211> LENGTH: 21
<212> TYPE: RNA
<213> ORGANISM: Homo sapiens

<400> SEQUENCE: 41
acagcaggca cagacaggca g                                             21

<210> SEQ ID NO 42
<211> LENGTH: 22
<212> TYPE: RNA
<213> ORGANISM: Homo sapiens

<400> SEQUENCE: 42
gugaaauguu uaggaccacu ag                                            22

<210> SEQ ID NO 43
<211> LENGTH: 21
<212> TYPE: RNA
<213> ORGANISM: Homo sapiens

<400> SEQUENCE: 43
gccccugggc cuauccuaga a                                             21

<210> SEQ ID NO 44
<211> LENGTH: 22
<212> TYPE: RNA
<213> ORGANISM: Homo sapiens

<400> SEQUENCE: 44
uccuucauuc caccggaguc ug                                            22
```

METHOD FOR INHIBITING OR REDUCING DRY EYE DISEASE BY IL-1RA

RELATED APPLICATIONS

This application is a national stage application, filed under 35 U.S.C. § 371, of International Application No. PCT/US2008/009776, filed on Aug. 15, 2008 which claims the benefit of U.S. Ser. No. 60/965,135, filed Aug. 16, 2007 and U.S. Ser. No. 61/130,687, filed Jun. 2, 2008.

FIELD OF THE INVENTION

This invention relates generally to the field of opthalmology.

BACKGROUND OF THE INVENTION

Inflammation of the ocular and adnexal tissues can occur by a variety of mechanisms and is associated, either primarily or secondarily, with a large number of disease conditions. Current treatments for inflammation of these tissues involve the systemic administration of antibiotics, steroids, and immune-system inhibitors. The difficulty of using these systemic drugs becomes apparent through damaging long-term side effects in the case of steroids, long-term drug resistance in the case of antibiotics, or insufficient long-term persistence at the target site in the case of signaling inhibitors. Moreover, the systemic inhibition of signaling within the immune system can have deleterious outcomes for individuals already afflicted with disease, whose susceptibility to additional complications is increased as a result of the systemic use of these treatments.

SUMMARY OF THE INVENTION

The present invention overcomes these obstacles by administering a topical composition comprising one or more antagonists of IL-1 function, or a combination of IL-1 and other inflammatory antagonists, to locally decrease or prevent inflammation of the ocular and adnexal tissues.

A method for inhibiting or reducing the severity of an ocular inflammatory disorder is carried out by locally administering to an ocular or adnexal tissue of a subject a composition that inhibits an activity of an inflammatory interleukin-1 cytokine such as binding of an inflammatory IL-1 cytokine to an IL-1 receptor. The subject is identified as suffering from a ocular inflammatory disorder by detecting a sign or symptom selected from the group consisting of epithelial overexpression of an inflammatory cytokine, vascular hyperplasia or thickening of lid margin, neovascularization of lid margin or corneal periphery, increase of leukocytes at an ocular or adnexal tissue, or overexpression of a matrix metalloprotease at an ocular or adnexal tissue. The method of therapy inhibits or reduces the severity of at least one of these signs or symptoms. For example, the inflammatory disorder is blepharitis. The method comprises administration of a compound that inhibits binding of an inflammatory IL-1 cytokine to an IL-1 receptor. Optionally, the composition also contains an antibiotic compound. The composition does not comprise tetracycline alone, e.g. in the absence of a functional antagonist that specifically targets IL-1. For example, the composition comprises an antibiotic composition administered in combination with a functional antagonist specifically targeting IL-1.

The composition that inhibits binding of an inflammatory IL-1 cytokine to an IL-1 receptor comprises the amino acid sequence of SEQ ID NO: 16. For example, the composition is present in a concentration range of 0.1-10%, with preferred ranges between 1-5%, or 2-2.5% (mg/ml). Exemplary liquid formulations for eye drops contain 2-2.5% (mg/ml) of the composition. Preferred formulations are in the form of a solid, a paste, an ointment, a gel, a liquid, an aerosol, a mist, a polymer, a film, an emulsion, or a suspension. The formulations are administered topically, e.g., the composition is delivered to an ocular or adnexal tissue to directly contact that tissue. The method does not involve systemic administration or substantial dissemination of the composition to non-ocular or non-adnexal tissue. For example, subcutaneous injection of Kineret (see SEQ ID NO: 15 and 16) at 1-2 mg/kg results in an estimated peak blood serum concentration of about 1200-1500 ng/ml 7 hours post-injection. Topical administration of Kineret, as disclosed herein, temporally and spatially restricts absorption of the drug to a much greater degree than subcutaneous injection. The systemic dissemination of a topically administered Kineret composition contributes significantly less drug to the blood serum concentration than a subcutaneous injection.

Optionally, the composition further contains a compound selected from the group consisting of a physiological acceptable salt, poloxamer analogs with carbopol, carbopol/hydroxypropyl methyl cellulose (HPMC), carbopol-methyl cellulose, carboxymethylcellulose (CMC), hyaluronic acid, cyclodextrin, and petroleum.

The invention comprises a composition that inhibits an activity of an inflammatory interleukin-1 cytokine, the composition being in the form of a solid, a paste, an ointment, a gel, a liquid, an aerosol, a mist, a polymer, a film, an emulsion, or a suspension. The composition is present at a concentration of 0.1-10% (mg/ml). An exemplary composition includes a polypeptide comprising the amino acid sequence of SEQ ID NO: 16.

A method for inhibiting or reducing the severity of an ocular inflammatory disorder is also carried out by locally administering to an ocular or adnexal tissue of a subject a composition comprising a polynucleotide, a polypeptide, an antibody, a compound, or a small molecule that inhibits the transcription, transcript stability, translation, modification, localization, secretion, or function of a polynucleotide or polypeptide encoding an inflammatory interleukin-1 cytokine (IL-1a, SEQ ID NO: 1 and 2, or IL-1b, SEQ ID NO: 3 and 4), an IL-1 receptor (type 1, SEQ ID NO: 17 and 18, or type 2, SEQ ID NO: 17-21), an IL-1R binding protein (IL-1RAP, SEQ ID NO: 24-27), or an IL-1R downstream signaling effector (IRAK1, SEQ ID NO: 28-33).

Alternatively, the composition inhibits or enhances the transcription, transcript stability, translation, modification, localization, secretion, or function of a polynucleotide or polypeptide encoding the IL-1 receptor, type 2 (IL-1R2). IL-1R2 binds IL-1 and can inhibit the function of IL-1R1. Thus, in one embodiment, enhancement of IL-1R2 function provides another mechanism by which IL-1R1 activity is inhibited. In this same embodiment, inhibition of an antagonist of IL-1R2, specifically, IL-1Ra3, inhibits IL-1R1 function. Thus, the composition alone, or in combination with an enhancer of IL-1R2, inhibits the transcription, transcript stability, translation, modification, localization, secretion, or function of a polynucleotide or polypeptide encoding IL-1Ra3, SEQ ID NO: 22 or 23. Alternatively, in an embodiment wherein IL-1R2 receptor function augments the activity of IL-1R1, the composition contains one or more regions of a polynucleotide or polypeptide encoding IL-1Ra3 to augment IL-1R2 inhibition. Furthermore, the composition of this embodiment comprises the whole polynucleotide or polypeptide encoding IL-1Ra3.

The composition comprises a polynucleotide, a polypeptide, an antibody, a compound, or a small molecule with means to inhibit the transcription, transcript stability, translation, modification, localization, secretion, or function of a polynucleotide or polypeptide encoding an accessory protein of an IL-1 Receptor. For example, this IL-1 receptor accessory protein is IL-1RAP, which directly binds IL-1 and IL-1R1, and is defined by the polynucleotide sequence of SEQ ID NO: 24 or 26 and the polypeptide sequence of SEQ ID NO: 25 or 27. IL-1 RAP belongs to a signaling complex that is required for signal transduction from IL-1R1. Thus, inhibition of IL-1RAP antagonizes IL-1R1 function.

In another embodiment, the composition comprises a polynucleotide, a polypeptide, an antibody, a compound, or a small molecule with means to inhibit the transcription, transcript stability, translation, modification, localization, secretion, or function of a polynucleotide or polypeptide encoding an associated kinase to an IL-1 receptor. For example, IL-1 receptor-associated kinase is IRAK1. IRAK1 is a downstream signaling effector that leads to transcriptional events associated with escalating inflammatory responses and is defined by the polynucleotide sequence of SEQ ID NO: 28, 30, or 32 and the polypeptide sequence of SEQ ID NO: 29, 31, or 33. Upon IL-1 receptor binding by IL-1, IRAK1 is recruited to the receptor complex, becomes hyperphosphorylated, and participates in the formation of a new protein complex consisting of hyperphosphorylated IRAK1 and TRAF6. The formation of this IRAK1/TRAF6 complex is a prerequisite for tumor necrosis factor (TNF) associated factor 6 (TRAF6)-mediated activation of nuclear factor-κB (NF-κB) and subsequent induction of an inflammatory response. Thus, the inhibition of IRAK1 expression and/or function provides an additional mechanism for inhibiting an IL-1-mediated immune response.

The composition comprises a polynucleotide, a polypeptide, an antibody, or a small molecule that binds or modifies the function of IL-1α, IL-1b, IL-1R1, IL-1R2, IL-1Ra3, IL-1 RAP, or IRAK1. Moreover the composition comprises morpholino antisense oligonucleotides, microRNAs (miRNAs), short hairpin RNA (shRNA), or short interfering RNA (siRNA) to silence gene expression. Exemplary compounds to be adapted for topical administration include, but are not limited to, anakinra/Kineret® (recombinant human IL-1Ra, rhIL-1Ra, and SEQ ID NO: 15 and 16), IL-1R antisense oligomers (U.S. Patent No. 2005033694), IL-1Ra-like nucleic acid molecule (Amgen, U.S. Patent No. 2001041792), and polynucleotide encoding a soluble IL-1R accessory molecule (Human Genome Sciences, U.S. Pat. No. 6,974,682).

The composition comprises microRNA molecules adapted for topical administration to ocular or adnexal tissues in order to silence gene expression. Exemplary miRNAs that bind to human IL-1α include, but are not limited to, miR-30c (SEQ ID NO: 34), miR-30b (SEQ ID NO: 35), miR-30a-5p (SEQ ID NO: 36), and miR-24 (SEQ ID NO: 37). Exemplary miRNAs (and corresponding sequences) that bind to human IL-1R1 include, but are not limited to, miR-135b (SEQ ID NO: 38), miR-326 (SEQ ID NO: 39), miR-184 (SEQ ID NO: 40), miR-214 (SEQ ID NO: 41), miR-203 (SEQ ID NO: 42), miR-331 (SEQ ID NO: 43), and miR-205 (SEQ ID NO: 44).

Exemplary polypeptides to be adapted for topical administration to ocular or adnexal tissues include, but are not limited to, anakinra/Kineret® (recombinant human IL-1Ra, rhIL-1Ra, and SEQ ID NO: 15 and 16), AF12198 (binds human IL-1R1, Ac-FEWTPGWYQJYALPL-NH2 where J represents the unnatural amino acid, 2-azetidine-1-carboxylic acid, SEQ ID NO: 45), IL-1R and IL-1RAP peptide antagonists (U.S. Patent No. 20060094663), IL-1R accessory molecule polypeptides (U.S. Patent No. 20050171337), IL-1Ra peptides (U.S. Patent No. 2005105830), and IL-1Ra-related peptides (Amgen, U.S. Patent No. 2001042304).

Exemplary antibodies to be adapted for topical administration to ocular or adnexal tissues include, but are not limited to, IL-1 TRAP (inline fusion double chain protein of IL1R-gp130 with hIgGFc, Regeneron, U.S. Issued U.S. Pat. No. 6,927,044), anti-IL-1α (U.S. Patent No. 20030026806), anti-IL-1β (U.S. Patent No. 20030026806 and Yamasaki et al. Stroke. 1995; 26:676-681), and humanized monoclonal anti-IL-1R (Amgen, U.S. Patent No. 2004022718 and Roche, U.S. Patent No. 2005023872).

Small molecules are organic or inorganic. Exemplary organic small molecules include, but are not limited to, aliphatic hydrocarbons, alcohols, aldehydes, ketones, organic acids, esters, mono- and disaccharides, aromatic hydrocarbons, amino acids, and lipids. Exemplary inorganic small molecules comprise trace minerals, ions, free radicals, and metabolites. Alternatively, small molecule inhibitors can be synthetically engineered to consist of a fragment, or small portion, or a longer amino acid chain to fill a binding pocket of an enzyme. Typically small molecules are less than one kilodalton. An exemplary small molecule to be adapted for topical administration to ocular or adnexal tissues is ZnPP (IL-1 blocker zinc protoporphyrin, naturally-occurring metabolite, Yamasaki et al. Stroke. 1995; 26:676-681).

The composition does or, alternatively, does not comprise one or more antibiotic compositions to be used in combination with an antagonist of IL-1 function. The antibiotic and IL-1 antagonist compositions are administered simultaneously or sequentially. Exemplary antibiotic compositions used for combination-therapy with antagonists of IL1-mediated inflammation include but are not limited to, amikacin, gentamicin, kanamycin, neomycin, netilmicin, streptomycin, tobramycin, teicoplanin, vancomycin, azithromycin, clarithromycin, clarithromycin, dirithromycin, erythromycin, roxithromycin, troleandomycin, amoxicillin, ampicillin, azlocillin, carbenicillin, clozacillin, dicloxacillin, flucozacillin, mezlocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, oflazacin, trovafloxacin, mafenide, sulfacetamide, sulfamethizole, sulfasalazine, sulfisoxazole, trimethoprim, cotrimoxazole, demeclocycline, soxycycline, minocycline, oxytetracycline, or tetracycline.

The composition comprises an antagonist of an IL-1 cytokine or an IL-1 receptor, administered simultaneously or sequentially with a second immunosuppressive composition. The immunosuppressive compound comprises cyclosporin A or analogs thereof a concentration of 0.05-4.0% (mg/ml). Alternatively, or in addition, the immunosuppressive composition comprises a glucocorticoid, a cytostatic agent, an alkylating agent (nitrogen mustards/cyclophosphamide, nitrosoureas, platinum compounds), an antimetabolic agent (methotrexate, any folic acid analog, azathioprine, mercaptopurine, any purine analog, any pyrimidine analog, any inhibitor of protein synthesis), a cytotoxic antibiotic (dactinomycin, an anthracycline, mitomycin C, bleomycin, mithramycin), a polyclonal antibody (Atgam®, Thympglobuline®, any antibody against the anti-lymphocyte or antithymocyte antigens), a monoclonal antibody (OKT3®, any antibody against the T-cell receptor, any antibody against IL-2, basiliximab/Simulect®, declizumab/

Zenapax®), Tacrolimus/Prograf™/FK506, Sirolimus/Rapamune™/Rapamycin, interferon beta, interferon gamma, an opioid, a TNFα binding protein, mycophenolate, or FTY720.

The composition comprises a polynucleotide, a polypeptide, an antibody, or a small molecule that binds or modifies the function of IL-1α, IL-1b, IL-1Ra, IL-1R1, IL-1R2, Il-1Ra3, IL-1RAP, or IRAK1, administered topically with a pharmaceutically appropriate carrier. Delivery methods for polynucleotide compositions include, but are not limited to, liposomes, receptor-mediated delivery systems, naked DNA, and engineered viral vectors such as herpes viruses, retroviruses, adenoviruses and adeno-associated viruses, among others. Polynucleotide compositions are administered topically with a pharmaceutically acceptable liquid carrier, e.g., a liquid carrier, which is aqueous or partly aqueous. Alternatively, polynucleotide sequences within the composition are associated with a liposome (e.g., a cationic or anionic liposome).

A number of methods have been developed for delivering short DNA or RNA sequences into cells; e.g., polynucleotide molecules can be contacted directly onto the tissue site, or modified polynucleotide molecules, designed to specifically target desired cell types (e.g., sequences linked to peptides or antibodies that specifically bind receptors or antigens expressed on the target cell surface).

A preferred approach uses a recombinant DNA construct in which the short polynucleotide sequence is placed under the control of a strong polymerase III or polymerase II promoter. The use of such a construct will result in the transcription of sufficient amounts of polynucleotide that will form complementary base pairs with the endogenous transcripts of nucleic acids of the invention and thereby prevent translation of endogenous mRNA transcripts. The invention encompasses the construction of a short polynucleotide using the complementary strand as a template. For example, a vector can be introduced in vivo such that it is taken up by a cell and directs the transcription of an interfering RNA or precursor to a double stranded RNA molecule. Alternatively, the template for the short polynucleotide transcript is placed under the transcriptional control of a cell-type specific promoter or other regulatory element. Thus, diffusion or absorption of a topically administered composition beyond the intended ocular or adnexal target tissue does not cause deleterious or systemic side effects. The vector remains episomal or becomes chromosomally integrated, as long as it can be transcribed to produce the desired polynucleotide.

Vectors are constructed by recombinant DNA technology methods standard in the art. Vectors can be plasmid, viral, or others known in the art, used for replication and expression in mammalian cells. Expression of the sequence encoding the short polynucleotide can be placed under the control of any promoter known in the art to act in mammalian, preferably human cells. Promoters are inducible or constitutive. Exemplary promoters include, but are not limited to: the SV40 early promoter region (Bernoist et al., Nature 290: 304, 1981); the promoter contained in the 3' long terminal repeat of Rous sarcoma virus (Yamamoto et al., Cell, 22:787-797, 1988); the herpes thymidine kinase promoter (Wagner et al., Proc. Natl. Acad. Sci. USA, 78:1441, 1981); or the regulatory sequences of the metallothionein gene (Brinster et al., Nature, 296:39, 1988).

Polypeptide compositions are associated with liposomes alone or in combination with receptor-mediated delivery systems, to enable transport across the plasma membrane. Polypeptide compositions are soluble or membrane-bound.

An exemplary receptor-mediated delivery system involves fusion of a low-density or very-low-density lipoprotein containing particle or vesicle to the low-density lipoprotein (LDL) receptor (LDLR) as observed with Hepatitis C Virus (HCV) infection and HCV-mediated drug delivery methods.

Compositions comprise one or more extracellular or intracellular antibodies, also called intrabodies, raised against one or more of the following: IL-1α, IL-1b, IL-1Ra, IL-1R1, IL-1R2, Il-1Ra3, IL-1RAP, or IRAK1. Extracellular antibodies are topically administered with a pharmacologically appropriate aqueous or non-aqueous carrier. Sequences encoding intracellular antibodies are subcloned into a viral or mammalian expression vector, packed in a lipophilic device to facilitate transport across the plasma membrane, and topically administered to ocular or adnexal tissue with a pharmacologically appropriate aqueous or non-aqueous carrier. Once inside the plasma membrane, host cell machinery transcribes, translates, and processes the intrabody code to generate an intracellular function-blocking antibody targeted against IL-1α, IL-1b, IL-1Ra, IL-1R1, IL-1R2, Il-1Ra3, IL-1RAP, or IRAK1. In the case of secreted molecules, intracellular antibodies prevent post-translational modification or secretion of the target protein. In the case of membrane-bound molecules, intracellular antibodies prevent intracellular signaling events upon receptor engagement by IL-1 cytokines.

The composition comprises an antagonist of IL-1 and/or IL-1R function in combination with other inhibitory elements. Antagonists of IL-1 and/or IL-1R and other inhibitory elements are administered simultaneously or sequentially. In one embodiment, the composition comprises an antagonist of IL-1 and/or IL-1R function and an antagonist of tumor necrosis factor alpha (TNFα). Exemplary functional blockers of TNFα include, but are not limited to, recombinant and/or soluble TNFα receptors, monoclonal antibodies, and small molecule antagonists and/or inverse agonists. One or more commercially-available TNF-α blocking agents are reformulated for topical administration in this embodiment. Exemplary commercial TNF-α blocking agents used for reformulation include, but are not limited to, etanerept/Embrel, infliximab/Remicade, and adalimumab/Humira. Alternatively, the composition comprises an antagonist of IL-1 and/or IL-1R function and antagonist(s) of one or more interleukin cytokines. Exemplary cytokines include, but are not limited to, IL-2, IL-4, IL-5, IL-6, IL-8, IL-12, IL-17, IL-18, and IL-23. In another embodiment, the composition comprises an antagonist of IL-1 and/or IL-1R function and antagonist(s) of one or more member(s) of the vascular epithelial growth factor (VEGF) family composed of growth factors and receptors (VEGFR). Exemplary members include, but are not limited to, VEGF-A, VEGF-C, VEGFR-2, and VEGFR-3. In another embodiment, the composition comprises an antagonist of IL-1 and/or IL-1R function and an antagonist of interferon-gamma. In another embodiment, the composition comprises an antagonist of IL-1 and/or IL-1R function and antagonist(s) of one or more chemokines and their receptors. Exemplary chemokines and receptors comprised by the composition of this embodiment include, but are not limited to, chemokine (C-C motif) receptor 1 (CCR1), chemokine (C-C motif) receptor 2 (CCR2), chemokine (C-C motif) receptor 5 (CCR5), chemokine (C-C motif) receptor 7 (CCR7), and chemokine (C-X-C motif) receptor 3 (CXCR3).

In embodiments wherein the composition comprises an antagonist of IL-1 and/or IL-1R function and antagonist(s) of one or more inflammatory species, the respective doses of the IL-1 antagonist to the other inflammatory antagonist(s)

is a ratio between 1:10 and 10:1 (mass/weight). Alternatively, the ratio is 1:9, 1:8, 1:7, 1:6, 1:5, 1:4, 1:3, 1:2, 1:1, 2:1, 3:1, 4:1, 5:1, 6:1, 7:1, 8:1, or 9:1.

The invention also comprises a contact lens device consisting of a composition that inhibits an activity of an inflammatory interleukin-1 cytokine and a pharmaceutically compatible polymer. This composition also comprises a combination of antagonists of IL-1 or IL-1R function as well as antagonists of other inflammatory agents. For example, the composition is incorporated into or coated onto said lens. The composition is either chemically bound or physically entrapped by the contact lens polymer. The contact lens is either hydrophobic or hydrophilic.

The invention comprises a drug-delivery device consisting of a composition that inhibits an activity of an inflammatory interleukin-1 cytokine and a pharmaceutically compatible polymer. This composition also comprises a combination of antagonists of IL-1 or IL-1R function as well as antagonists of other inflammatory agents. For example, the composition is incorporated into or coated onto said polymer. The composition is either chemically bound or physically entrapped by the polymer. The polymer is either hydrophobic or hydrophilic. The polymer device comprises multiple physical arrangements. Exemplary physical forms of the polymer device include, but are not limited to, a film, a scaffold, a chamber, a sphere, a microsphere, a stent, or other structure. The polymer device has internal and external surfaces. The device has one or more internal chambers. These chambers contain one or more compositions. The device contains polymers of one or more chemically-differentiable monomers. The subunits or monomers of the device polymerize in vitro or in vivo.

Exemplary mucoadhesive polyanionic natural or semi-synthethic polymers from which the device is formed include, but are not limited to, polygalacturonic acid, hyaluronic acid, carboxymethylamylose, carboxymethylchitin, chondroitin sulfate, heparin sulfate, and mesoglycan. In one embodiment, the device comprises a biocompatible polymer matrix that may optionally be biodegradable in whole or in part. A hydrogel is one example of a suitable polymer matrix material. Examples of materials which can form hydrogels include polylactic acid, polyglycolic acid, PLGA polymers, alginates and alginate derivatives, gelatin, collagen, agarose, natural and synthetic polysaccharides, polyamino acids such as polypeptides particularly poly (lysine), polyesters such as polyhydroxybutyrate and poly-.epsilon.-caprolactone, polyanhydrides; polyphosphazines, poly(vinyl alcohols), poly(alkylene oxides) particularly poly (ethylene oxides), poly(allylamines)(PAM), poly(acrylates), modified styrene polymers such as poly(4-aminomethylstyrene), pluronic polyols, polyoxamers, poly(uronic acids), poly(vinylpyrrolidone) and copolymers of the above, including graft copolymers. In another embodiment, the scaffolds may be fabricated from a variety of synthetic polymers and naturally-occurring polymers such as, but not limited to, collagen, fibrin, hyaluronic acid, agarose, and laminin-rich gels.

One preferred material for the hydrogel is alginate or modified alginate material. Alginate molecules are comprised of (1-4)-linked β-D-mannuronic acid (M units) and α L-guluronic acid (G units) monomers which vary in proportion and sequential distribution along the polymer chain. Alginate polysaccharides are polyelectrolyte systems which have a strong affinity for divalent cations (e.g. $Ca^{+2}$, $Mg^{+2}$, $Ba^{+2}$) and form stable hydrogels when exposed to these molecules. See Martinsen A., et al., Biotech. & Bioeng., 33 (1989) 79-89.

An embodiment of the invention utilizes an alginate or other polysaccharide of a lower molecular weight, preferably of size which, after dissolution, is at the renal threshold for clearance by humans. Polymeric devices are located topically or subcutaneously, though very superficially, wherein either a composition chemically bound or physically entrapped by the polymeric device or the device itself, degrades and must be cleared from the body. For a biodegradable polymeric device, it is preferred that the alginate or polysaccharide is reduced to a molecular weight of 1000 to 80,000 daltons, more preferably 1000 to 60,000 daltons, particularly preferably 1000 to 50,000 daltons. It is also useful to use an alginate material of high guluronate content since the guluronate units, as opposed to the mannuronate units, provide sites for ionic crosslinking through divalent cations to gel the polymer.

Internal and external surfaces optionally contain pores. Pores are either created prior to administration into a subject or result from the inclusion of pore-forming agents within the device that perforate surfaces upon administration to a subject. Exemplary pore forming agents include, but are not limited to, water soluble compounds such as inorganic salts and sugars. Pore forming agents are added as particulates and comprise between one and thirty percent (weight/weight of polymer). Pore size is sufficient for diffusion of proteins but not large enough cell migration into or out of the device.

The device is administered topically, subconjuntively, or in the episcleral space, subcutaneously, or intraductally. Specifically, the device is placed on or just below the surface if an ocular or adnexal tissue. Alternatively, the device is placed inside a tear duct or gland. The composition incorporated into or onto the polymer is released or diffuses from the device.

The invention comprises a method of contacting a composition, with means to inhibit IL-1R activity, to an ocular or adnexal tissue surface of a subject who presents symptoms or associated conditions of posterior blepharitis. Unlike all other treatments for this condition, this method comprises a composition that is topically administered to the subject and affects local disease mechanisms without the side effects present with systemically administered treatments. The composition is not only effective immediately, but also safe for long-term administration.

The invention comprises a method of treating non-infectious eye disease, wherein a composition containing an inhibitor of IL-1 or IL-1R function alleviates, prevents, or attenuates a symptom, cause, or mechanism of said disease by contacting said composition to the ocular surface of an affected subject. Exemplary disease mechanisms comprise inflammation, hyperplasia, neovascularization, leukocyte recruitment, or cytokine production within superficial eye structures and those structures juxtaposed to the ocular surface. For instance, non-infectious eye disease is caused by obstruction, thickening, inflammation, neovascularization, or atrophy of the meibomian glands. Alternatively, non-infectious eye disease is caused by damage to structures other than the meibomian glands. Exemplary alternative causes include, but are not limited to, oily tear film, papillary hypertrophy of the tarsal conjunctiva, corneal punctate epitheliopathy, vernal keratoconjunctivitis, atopic keratoconjunctivitis, chemical burn, trachoma, pterygium, pemphigoid, corneal angiogenesis (growth of new blood vessels), psoriasis, iethyosis, erythema mutiforme, anhydrotic ectodermal dysplasia, systemic retinoid therapy, or exposure to polychlorinated byphenols. Finally, non-infectious eye disease can also result from a deficient tear lipid layer, an increase in tear evaporation, or the occurrence of an evaporative dry eye. The methods treat non-infectious eye disease that is or is not coincident with the presentation of dermatoses comprising acne rosacea, seborrhoeic dermatitis, or atopic dermatitis. Furthermore, methods are applicable to treat a primary or secondary non-infectious eye disease that is coincident with chalazia, pannus, phlyctenules, recurrent conjunctivitis, ocular surface damage, ocular rosacea, corneal ulceration, corneal perforation or secondary complications of ocular infection.

The methods described herein are not intended to treat eye disease that results from an immune response that consequently arises following the transplantation of foreign tissue onto or into an ocular or adnexal tissue. For instance, inflammatory responses occur following host rejection of corneal transplant or as a consequence of infection following surgical procedures. The instant application is not intended to treat eye conditions that result directly from tissue rejection or infectious disease. However, immune responses to foreign tissues or to infectious agents can lead to protean secondary complications, such as growth of blood or lymph vessels, or overexpression of molecules that cause tissue injury; in such cases the methods described in the present application are useful as a treatment for reducing inflammation associated with such secondary complications. Furthermore, the methods and devises comprising the instant application are not intended to treat conditions arising from autoimmune responses, e.g. immune responses raised against healthy host tissues.

In a preferred embodiment, the non-infectious eye disease comprises blepharitis and/or posterior blepharitis that is or is not coincident with inflammation of the posterior lid margin, inflammation of the ocular surface, burning, irritation, or patient discomfort. Alternatively, the present invention is intended to treat blepharitis that is coincident with meibomian gland dysfunction.

The methods alleviate symptoms of non-infectious eye disease. Exemplary symptoms include, but are not limited to, dryness, discomfort, burning, itching, irritation, inflammation, skin abnormalities surrounding the eye, photophobia, blurred vision, and contact lens intolerance.

The present invention comprises a composition with variable physical and chemical forms; however, the composition is topically administered and contacts an ocular or adnexal tissue directly. The composition is administered as a solid, a paste, an ointment, a gel, a liquid, an aerosol, a mist, a polymer, a film, an emulsion, or a suspension. Furthermore, the composition is incorporated into or coated onto a contact lens, from which one or more molecules diffuse away from the lens or are released in a temporally-controlled manner. In this embodiment, the contact lens composition either remains on the ocular surface, e.g. if the lens is required for vision correction, or the contact lens dissolves as a function of time simultaneously releasing the composition into closely juxtaposed tissues.

In one preferred embodiment, the present invention comprises a composition with means to inhibit the transcription, transcript stability, translation, modification, localization, secretion, or receptor binding of IL-1α, IL-1β, or a combination of both cytokines. In one embodiment, the composition comprises a polynucleotide capable of binding to a region of the IL-1α mRNA transcript, defined by SEQ ID NO: 1. In another embodiment, the composition comprises a polynucleotide capable of binding to a region of the IL-1β mRNA transcript, defined by SEQ ID NO: 3.

In another embodiment, the composition is capable of increasing the abundance of the naturally-occurring IL-1 Receptor antagonist (IL-1Ra). The composition comprises a polynucleotide, a polypeptide, an antibody, a compound, or a small molecule that binds to a region of the IL-1Ra gene, mRNA transcript defined by SEQ ID NO: 5, 7, 9, 11, or 13, a polypeptide isoform of IL-1Ra defined by SEQ ID NO: 6, 8, 10, 12, or 14, or a recombinant IL-1Ra protein defined by SEQ ID NO: 16. Alternatively, the composition contains mRNA transcripts or polypeptides encoding a region or the entirety of the IL-1Ra gene.

The composition comprises an antagonist or inverse agonist of a receptor for IL-1α or IL-1β, specifically, IL-1R1. In this embodiment an antagonist is defined as a binding partner, or ligand, of an IL-1R that inhibits the function of an agonist, IL-1, or inverse agonist by blocking its binding to the receptor. An inverse agonist is defined as a molecule which binds to the same IL-1R binding-site as an agonist, for instance, IL-1, but exerts the opposite pharmacological effect. The composition contains a polynucleotide, a polypeptide, an antibody, a compound, or a small molecule that binds to a region of the IL-1R1 defined by the polynucleotide and polypeptide sequences SEQ ID NO: 17-21. In an alternative embodiment, the composition comprises a molecule with means to inhibit IL-1R transcription, transcript stability, translation, modification, localization, secretion, ligand binding, or association with an accessory protein of an IL-1R (IL-1RAP). IL-1RAP is defined by the polynucleotide sequence of SEQ ID NO: 24 or 26 and the amino acid sequence of SEQ ID NO: 25 or 27.

The composition comprises a molecule with means to inhibit IL-1α- or IL-β-mediated modulation of matrix metalloproteinase (MMP) overexpression, which degrades collagen matrices within tissues and retards wound healing.

In another preferred embodiment, the composition comprises a human recombinant IL-1R antagonist either in pure form, or as a component of a mixture. The human recombinant IL-1R antagonist is combined with balanced saline, carboxymethylcellulose (CMC), or hyaluronic acid (HA), or other vehicles prior to the composition contacting the ocular or lid surface. Within these mixtures, the human recombinant IL-1R antagonist comprises at least 0.1%, 2.0%, 2.5%, 5%, or at most 10% of the total volume administered. Preferred aqueous formulations contain 2-2.5% of the purified antagonist. Purified is defined as the antagonist in the absence of unrelated polynucleotides, polypeptides, cellular organelles, or lipids. Purified is defines a degree of sterility that is safe for administration to a human subject, e.g. lacking infectious or toxic agents.

Affected subjects to which this invention is administered are identified by a variety of methods. The following examinations are used individually or combinatorially to assess the presence or absence of non-infectious eye disease (for explanation of examinations, see Examples). Subjects are identified by a break-up time of less than 10 seconds following a standard Tear Film Break-up Time (TFBT) test. Subjects are identified by a significant corneal fluorescein staining of tear film and/or conjunctival lissamine green or rose bengal staining. Subjects are identified by a result of 10 mm or less for the Schrimer test with or without anesthesia. Subjects are identified by significantly viscous tear excreta and/or a decrease in the number of meibomian glands or meibomian gland orifices capable of excreting tears. Subjects are identified by shades of red discoloration of the lid margin, palpebral conjunctiva, and/or bulbar conjunctiva indicating increasing extreme vascular injection (erythema). Subjects are also classified as presenting increasingly severe non-infectious eye disease with the increasing abundance and severity of the above factors.

The compositions and methods provided herein are used modify intraocular pressure. In one aspect of the invention, the compositions and methods provided herein are used to decrease intraocular pressure. Inhibitors or antagonists of IL-1 cytokines and/or IL-1 receptors are used alone or in combination with other compounds to modify intraocular pressure. In a preferred embodiment of the invention, inhibitors or antagonists of IL-1 cytokines and/or IL-1 receptors are used alone or in combination with other compounds to decrease intraocular pressure. Alternatively, or in addition, inhibitors or antagonists of IL-1 cytokines and/or IL-1 receptors are used alone or in combination with other compounds to treat ocular hypertension.

Exemplary compounds to be used in combination with IL-1 cytokines and/or IL-1 receptors include, but are not limited to, prostaglandin analogs (such as latanoprost (XALATAN®), bimatoprost (LUMIGAN®) and travoprost (TRAVATAN®) which increase uveoscleral or trabecular outflow of aqueous humor); topical beta-adrenergic receptor antagonists (such as timolol, levobunolol (BETAGAN®), and betaxolol, which decrease aqueous humor production by the ciliary body); Alpha2-adrenergic agonists (such as brimonidine (ALPHAGAN®), which work by a dual mechanism, decreasing aqueous production and increasing uveoscleral outflow); less-selective sympathomimetics (such as epinephrine and dipivefrin (PROPINE®), which increase outflow of aqueous humor through trabecular meshwork and possibly through uveoscleral outflow pathway, probably by a beta2-agonist action); miotic agents (parasympathomimetics) (such as pilocarpine, which work by contraction of the ciliary muscle, tightening the trabecular meshwork and allowing increased outflow of the aqueous humour); carbonic anhydrase inhibitors (such as dorzolamide (TRUSOPT®), brinzolamide (AZOPT®), acetazolamide (DIAMOX®), which lower secretion of aqueous humor by inhibiting carbonic anhydrase in the ciliary body); physostigmine which is also used to treat glaucoma and delayed gastric emptying; fish oil; omega 3 fatty acids, bilberries, vitamin E, cannabinoids, carnitine, coenzyme Q10, curcurmin, Salvia miltiorrhiza, dark chocolate, erythropoietin, folic acid, Ginkgo biloba, Ginseng, L-glutathione, grape seed extract, green tea, magnesium, melatonin, methylcobalamin, N-acetyl-L cysteine, pycnogenols, resveratrol, quercetin, and fludrocortisone.

The invention also provides compositions and methods for treating individuals or subjects with ocular hypertension including administrating to these subjects a composition comprising an IL-1 or IL-1R inhibitor or antagonist. In one aspect of the invention, the IL-1 or IL-1R inhibitor or antagonist is administered topically to the ocular surface as a liquid. In another aspect of the invention, the IL-1 or IL-1R inhibitor or antagonist is administered intraocularly by injection.

The invention also provides compositions and methods for preventing glaucoma in individuals or subjects with ocular hypertension including administrating to these subjects a composition comprising an IL-1 or IL-1R inhibitor or antagonist. In one aspect of the invention, the IL-1 or IL-1R inhibitor or antagonist is administered topically to the ocular surface as a liquid. In another aspect of the invention, the IL-1 or IL-1R inhibitor or antagonist is administered intraocularly by injection.

The invention provides a method for reducing intraocular pressure, including identifying a subject suffering from or at risk of a condition associated with above-normal intraocular pressure and locally administering to the subject a composition that inhibits an activity of an inflammatory interleukin-1 cytokine. In one preferred aspect of the invention, the condition is glaucoma.

In one aspect of the invention, subjects are identified by measuring their intraocular pressure and determining if the measured intraocular pressure is elevated above normal levels. As used herein, the term "normal level" is meant to describe value within an acceptable range of values that one of ordinary skill in the art and/or a medical professional would expect a healthy subject of similar physical characteristics and medical history to have. For example, normal intraocular pressure (IOP) is defined as IOP in the range of 10 mmHg to 21 mmHg.

In another aspect of the invention, subjects are identified as those individuals who are at risk for developing elevated intraocular pressure based upon non-limiting factors such as medical history (for instance, diabetes), side effects of medications, lifestyle and/or diet, medical intervention (such as surgery to the eye), trauma/injury, hormone changes, and aging. Compositions of the invention are administered to these subjects for preventative means.

All polynucleotides and polypeptides of the invention are purified and/or isolated. As used herein, an "isolated" or "purified" nucleic acid molecule, polynucleotide, polypeptide, or protein, can be substantially free of other cellular material, or culture medium when produced by recombinant techniques, or chemical precursors or other chemicals when chemically synthesized.

Publications, U.S. patents and applications, Genbank/NCBI accession numbers, and all other references cited herein, are herby incorporated by reference.

BRIEF DESCRIPTION OF THE DRAWINGS

FIG. 1 is the Ocular Surface Disease Index (OSDI) 12-item questionnaire.

FIG. 2 the Oxford Schema for grading corneal and conjunctival staining.

FIG. 5 is a questionnaire given to subjects of a study to diagnose Meibomian Gland Dysfunction (Posterior Blepharitis).

FIG. 6 is a flow diagram showing the sequence of clinical tests performed on study subjects during the screening process described in Example 8.

DETAILED DESCRIPTION

Posterior Blepharitis

Figure 3:
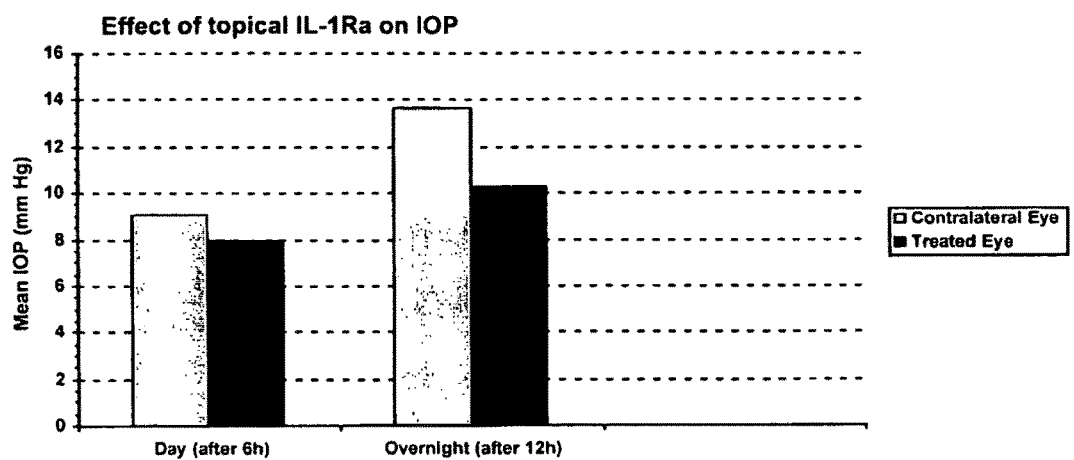
FIG. 3 is a graph representing the effect of IL-1a on intraocular pressure (IOP).

Posterior blepharitis is a common chronic eyelid condition that is described as generalized inflammation of the posterior lid margin and associated with inflammation of the ocular surface and with symptoms of burning, irritation, and discomfort. Posterior blepharitis is associated with various disorders of the meibomian glands, known collectively as meibomian gland dysfunction (MGD). It is associated either with obstruction and inflammation of the meibomian glands or, less commonly, atrophy of the meibomian glands (Foulks, G. et al. 2003. Ocul Surf. 107-26; Bron, A. J. et al. 2004. Ocul Surf. 2:149-65).

Clinically, MGD often presents with inspissated meibomian glands, oily tear film, as well as inflammation and vascularization of the meibomian gland orifices. Papillary hypertrophy of the tarsal conjunctiva and corneal punctate epitheliopathy are often present, and there are prominent associations with dermatoses, such as acne rosacea, seborrhoeic dermatitis, and atopic dermatitis. Other causes and associations of MGD are: vernal keratoconjunctivitis, atopic keratoconjunctivitis, chemical burns, trachoma, pemphigoid, psoriasis, iethyosis, erythema multiforme, anhydrotic ectodermal dysplasia, and systemic retinoid therapy. Additionally, exposure to polychlorinated biphenyls, through ingestion of contaminated cooking oils, causes a chronic form of MGD with gross and extensive acneiform skin changes (Fu, Y. A. 1984. Am J Ind Med. 5:127-32).

MGD of sufficient extent and degree is associated with a deficient tear lipid layer, an increase in tear evaporation, and the occurrence of an evaporative dry eye. In fact MGD is considered to be the most common cause of evaporative dry eye (Foulks, G. et al. 2003. Ocul Surf. 107-26). Individuals with MGD often complain of significant discomfort, including burning, itching, irritation, and photophobia. They may also have other associated symptoms of dry eye and may be plagued by blurred vision, gradual contact lens intolerance. Furthermore, these patients may become functionally handicapped by the negative impact of dry eye on their crucial daily activities such as working, using computer, reading, and driving (Goto, E. et al. 2002. Am J Opthalmol. 133: 181-186; Miljanovic, B. et al. 2007. Am J Opthalmol. 143: 409-15).

In addition to dry eye, other sequelae of MGD that confront the ophthalmologist include chalazia, pannus, phlyctenules, and recurrent conjunctivitis which increase risk of ocular surface damage, ocular infection, corneal ulceration, and perforation.

Despite the high incidence of posterior blepharitis, there is currently no consistently effective treatment for this condition and it still remains a therapeutic challenge. Posterior blepharitis has traditionally been managed with eyelid hygiene, topical antibiotics (erythromycin or bacitracin ointments), oral tetracyclines (tetracycline, doxycycline, or minocycline) and corticosteroids which are often time consuming, frustrating, and frequently ineffective or variably effective.

The current treatments for posterior blepharitis are limited, in part, by their inability to target the underlying pathophysiologic processes. There is ample evidence that posterior blepharitis is the result of an underlying cytokine and inflammatory-mediated process affecting both the meibomian glands and the ocular surface (Kocak-Altintas, A. G. et al. 2003. Eur J Opthalmol. 13:351-359; McCulley, J. P. et al. 2000. Cornea. 19:650-658). In an experimental blepharoconjunctivitis, it has been shown that T-cells are the prime orchestrator driving the infiltration of other inflammatory cells into the conjunctiva, as well as the upregulation of chemokines (Fukushima, A. et al. 2003. Invest. Opthalmol. Vis. Sci. 44:4366-4374).

In ocular rosacea which belongs to the large pathologic group of blepharitis and MGD, inflammation of the ocular surface was clearly demonstrated with an increase of inflammatory mediators in tears such as interleukin (IL)-1α (Barton, K. et al. 1997. Opthalmology. 104:1868-1874). Flow cytometry and impression cytology of conjunctival epithelium in ocular rosacea has demonstrated a significantly higher level of intercellular adhesion molecule-1 (ICAM-1) which is known to play a significant role in inflammation associated with dry eye disease. This expression of ICAM-1 could be due to the liberation of one or more pro-inflammatory cytokines such as IL-1β or interferon-γ (Pisella, P. J. et al. 2000. Opthalmology. 107:1841-9).

Importance of inflammation in the pathogenesis of posterior blepharitis is underscored by reports that the signs and symptoms of MGD markedly improve with anti-inflammatory therapies such as topical steroids (Marsh, P. et al. 1999. Opthalmology. 106:811-816).

Systemically administered tetracycline antibiotics have long been recognized as effective therapies for ocular surface inflammatory diseases. The semisynthetic tetracycline, doxycycline, has been reported to successfully treat the common dry eye condition acne rosacea. One of the mechanisms of action of doxycycline in MGD and dry eye may be the downregulation of the IL-1-mediated inflammatory cascade in the corneal epithelium (Solomon, A. et al. 2000. Invent. Opthalmol. Vis. Sci. 41:2544-57).

In addition, findings from several studies indicate that MGD is also associated with aqueous deficiency dry eye patients, especially those with Sjogren syndrome (SS) (McCulley, J. P. et al. 1977. A, J Opthalmol. 84:788-93; Shimazaki, J. et al. 1998. Opthalmology. 105: 1485-1488). In these studies, at least 35% of patients with aqueous tear deficiency had MGD. Classically, SS affects the exocrine glands, not the sebaceous glands such as the meibomian glands. Underlying inflammation as well as desiccation and keratinization of ocular surface epithelia occurs in chronic dry eye disease and plays a role in pathogenesis of MGD.

Consistent with the concept that inflammation is a key feature in the pathophysiology of dry eye syndrome is the finding that both aqueous tear deficiency and meibomian gland disease are effectively treated with the corticosteroid methylprednisolone (Marsh, P. et al. 1999. Opthalmology. 107:967-74). Unfortunately the long-term use of topical corticosteroids is limited by potential sight-threatening side effects, such as glaucoma and cataracts. Therefore, there is a clinical need for nontoxic steroid-sparing anti-inflammatory therapies that target the underlying inflammatory environment of the ocular surface in this common condition.

Based on the concept that inflammation is a key component of the pathogenesis of MGD and dry eye, therapies targeting the underlying inflammatory environment of the ocular surface represent a major improvement in the management of these conditions and will have a major clinical impact. Given the facts that IL-1-mediated inflammatory activities play a critical role on the ocular surface in patients with MGD and dry eye, therefore, local blockade of IL-1 activity by IL-1Ra, is used to reduce one or more symptoms of dry eye syndrome.

Ocular and Adnexal Tissues:

Ocular tissues or compartments that contact the compositions comprised by the present invention include, but are not limited to, the cornea, aqueous humor, iris, and sclera. The term "adnexal" is defined in general terms as the appendages of an organ. In the present invention, adnexal defines a number of tissues or surfaces that are in immediate contact with the ocular surface but are not, by definition, comprised by the ocular surface. Exemplary adnexal tissues include, but are not limited to, the eyelids, lacrimal glands, and extraocular muscles. Topical administration of the presently invented compositions contact the following tissues and structures within the eyelid: skin, subcutaneous tissue, orbicularis oculi, orbital septum, tarsal plates, palpebral conjuntiva, and meibomian glands. The adnexal tissues comprise all subdivisions of the lacrimal glands, including the orbital and palpebral portions, as well as all tissues contacted by these glands. Extraocular muscles belonging to this category of adnexal tissues include, but are not limited to, the superior and inferior rectus, lateral and medial rectus, and superior and inferior oblique muscles. Compositions comprised by the present invention are applied topically and contact these tissues either alone, or in combination with ocular tissues.

Intraocular Pressure

Intraocular pressure is maintained by the liquid aqueous humor, which is produced by the ciliary body of the eye. Aqueous humor normally does not go into the posterior segment of the eye; it is kept out of this area by the lens and the Zonule of Zinn. Instead, it stays only in the anterior segment, which is divided into the anterior and posterior chambers. While the anterior and posterior chambers are very similarly named to the anterior and posterior segments, they are not synonymous. The anterior and posterior chambers are both parts of the anterior segment.

When the ciliary bodies produce the aqueous humor, it first flows into the posterior chamber (bounded by the lens and the iris). It then flows through the pupil of the iris into the anterior chamber (bounded by the iris and the cornea). From here, it flows through a structure known as the trabecular meshwork to enter the normal body circulation. Thus, the two main mechanisms of ocular hypertension are an increased production of aqueous humor, or a decreased outflow of aqueous humor.

Ocular hypertension (OHT) is intraocular pressure higher than normal in the absence of optic nerve damage or visual field loss. Current consensus in opthalmology defines normal intraocular pressure (IOP) as that between 10 mmHg and 21 mmHg. Intraocular pressure is measured with a tonometer. Elevated IOP is the most important risk factor for glaucoma, so those with ocular hypertension are frequently considered to have a greater chance of developing the condition. Intraocular pressure can increase when a patient lies down. There is evidence that some glaucoma patients (e.g., normal tension glaucoma patients) with normal IOP while sitting or standing may have intraocular pressure that is elevated enough to cause problems when they are lying down.

Differences in pressure between the two eyes is often clinically significant, and potentially associated with certain types of glaucoma, as well as iritis or retinal detachment.

Because of the effect of corneal thickness and rigidity on measured value of intraocular pressure, some forms of refractive surgery (such as photorefractive keratectomy) can cause traditional intraocular pressure measurements to appear normal when in fact the pressure may be abnormally high.

Intraocular pressure may become elevated due to anatomical problems, inflammation of the eye, genetic factors, as a side-effect from medication, or during exercise. Intraocular pressure usually increases with age and is genetically influenced.

Hypotony, or ocular hypotony, is typically defined as intraocular pressure equal to or less than 5 mmHg. Such low intraocular pressure could indicate fluid leakage and deflation of the eyeball.

Glaucoma

Glaucoma is a leading cause of irreversible blindness. A primary risk factor for glaucoma is elevated intraocular pressure (IOP), which can contribute to significant optic nerve damage and vision loss. Elevated IOP due to reduction in aqueous outflow facility is a major causal risk factor. The main aqueous outflow pathway of the eye consists of a series of endothelial-cell lined channels in the angle of the anterior chamber comprising the trabecular meshwork (TM), Schlemm's canal, the collector channels and the episcleral venous system.

Glaucoma is a group of diseases of the optic nerve involving loss of retinal ganglion cells in a characteristic pattern of optic neuropathy. Although raised intraocular pressure is a significant risk factor for developing glaucoma, there is no set threshold for intraocular pressure that causes glaucoma. Untreated glaucoma leads to permanent damage of the optic nerve and resultant visual field loss, which can progress to blindness. Loss of visual field often occurs gradually over a long time and may only be recognized when it is already quite advanced. Once lost, this damaged visual field can never be recovered. Worldwide, it is the second leading cause of blindness. Glaucoma affects one in two hundred people aged fifty and younger, and one in ten over the age of eighty.

Ocular hypertension is the largest risk factor in most glaucomas. Though, in some populations only 50% of patients with primary open angle glaucoma have elevated ocular pressure. Diabetics and those of African descent are three times more likely to develop primary open angle glaucoma. Higher age, thinner corneal thickness, and myopia are also risk factors for primary open angle glaucoma. People with a family history of glaucoma have about a six percent chance of developing glaucoma. Asians are prone to develop angle-closure glaucoma, and Inuit have a twenty to forty times higher risk than Caucasians of developing primary angle closure glaucoma. Women are three times more likely than men to develop acute angle-closure glaucoma due to their shallower anterior chambers. Use of steroids can also cause glaucoma.

Primary open angle glaucoma (POAG) has been found to be associated with mutations in genes at several loci. Normal tension glaucoma, which comprises one third of POAG, is associated with genetic mutations.

There is increasing evidence of ocular blood flow to be involved in the pathogenesis of glaucoma. Current data indicate that fluctuations in blood flow are more harmful in glaucomatous optic neuropathy than steady reductions. Unstable blood pressure and dips are linked to optic nerve head damage and correlate with visual field deterioration.

A number of studies also suggest that there is a correlation, not necessarily causal, between glaucoma and systemic hypertension (i.e. high blood pressure). In normal tension glaucoma, nocturnal hypotension may play a significant role. On the other hand there is no clear evidence that vitamin deficiencies cause glaucoma in humans, nor that oral vitamin supplementation is useful in glaucoma treatment.

Various rare congenital/genetic eye malformations are associated with glaucoma. Occasionally, failure of the normal third trimester gestational atrophy of the hyaloid canal and the tunica vasculosa lentis is associated with other anomalies. Angle closure induced ocular hypertension and glaucomatous optic neuropathy may also occur with these anomalies. These rare developmental causes of glaucoma are modeled in mice.

Only a few glaucomas are associated with visible cellular inflammation in the ocular compartments; however, Interleukin-1 (IL-1) is consistently up-regulated by glaucomatous TM cells and acts as a key factor in accelerated TM cell injury. This condition is mediated by both IL-1 effect on the TM cells functioning as well as their expression of adhesion factors that can affect outflow facility. The net effect is that IL-1 can compromises the function of the trabecular meshwork, causing reduced outflow facility in the open angle glaucoma. Interleukin-1 receptor antagonist (IL-1Ra) is a naturally occurring IL-1 isoform that with high-affinity binds to the IL-1 receptors and blocks its effects. Therefore, topical application of IL-1Ra, such as human recombinant forms (anakinra/KINERET®) suppresses IL-1-mediated cell injury in TM, enhances outflow facility, and reduces IOP in glaucomatous eyes.

This mechanism of action is in contrast with the other views that IL-1 itself increases matrix metalloproteinase expression in the TM and increases outflow facility. Therefore, others believed that inhibition of action of IL-1 by an IL-1 neutralizing antibody or with IL-1 receptor antagonist causes reduced outflow facility in trabecular meshwork.

Interleukin-1 (IL-1):

The IL-1 family is a group of cytokines that function as major mediators of inflammation and immune response (Dinarello, C. A. 1996. Blood. 15:2095-2147). This family is composed of three forms: two proinflammatory forms, IL-1a and IL-1B, each having a precursor form, and an anti-inflammatory form, IL-1 receptor antagonist (IL-1Ra). The proinflammatory cytokine IL-1 plays an important role in inflammation and immunity by increasing chemokine production, adhesion factors, macrophage infiltration and activity, and lymphocyte proliferation. IL-1 has been implicated in the pathogenesis of human inflammatory diseases, such as rheumatoid arthritis, septic shock, and periodontitis (Jiang, Y. et al. 2000. Arthritis Rheum. 43:1001-1009; Okusawa, S. et al. 1988. J Clin Invest. 81: 1162-1172; McDevitt, M. J. et al. 2000. J. Periodontol. 71:156-163).

The IL-1 cytokines play an important role in the regulation of inflammation and wound healing in the corneal and ocular surface diseases (Fabre, E. J. et al. 1991. Curr Eye Res. 10:585-592; Rosenbaum, J. T. et al. 1995. Invest Opthalmol V is Sci. 36: 2151-2155). Both IL-1a and IL-1B have been found to modulate matrix metalloproteinase (MMP) expression by corneal stromal fibroblasts (Fini, M. E. et al. 1990. Invest Opthalmol V is Sci. 31:1779-1788). Increased levels of IL-1a and IL-1β have been shown in patients with Sjögren syndrome and ocular rosacea (Pflugfelder, S. C. et al. 1999. Curr Eye Res. 19:201-211; Solomon, A. et al. 2001. Invest Opthalmol V is Sci. 42:2283-2292). Levels of proinflammatory forms of IL-1 are directly correlated with the intensity of corneal fluorescein staining and are inversely correlated with conjunctival goblet cell density. In both types of dry eye syndrome, evaporative and aqueous deficiency, as tear clearance from the ocular surface decreases, the concentrations of both isoforms of the proinflammatory cytokine IL-1 increase in the tear fluid (Solomon, A. et al. 2001. Invest Opthalmol V is Sci. 42:2283-2292). The results of a study on the effects of doxycycline on the expression patterns of the IL-1 gene family in the human limbal epithelium in response to a strong inflammatory stimulus, have demonstrated an inhibitory effect of doxycycline on the expression of the inflammatory cytokine IL-1β, with a concomitant upregulation of the anti-inflammatory IL-1Ra (Solomon, A. et al. 2000. Invest Opthalmol V is Sci. 41:2544-57). These results imply that some of the clinically proven benefits of tetracycline compounds (tetracycline, doxycycline, and minocycline) in treating the ocular surface disease of MGD and dry eye may be mediated through their regulatory effects on the synthesis, processing, or release of IL-1.

IL-1 induces ocular surface disease, e.g., the chronic subclinical ocular surface inflammation of MGD and dry eye. The compositions and methods described herein inhibit the activity of human IL-1α and/or IL-1β, as defined by the ability to induce signal transduction or initiate/activate a downstream signaling cascade from an IL-1 receptor. Compositions that contain an inhibitor of human IL-1α or IL-1β function antagonize the activity of an IL-1 receptor. The composition comprises a polynucleotide, a polypeptide, an antibody, a compound, or a small molecule with means to inhibit the transcription, transcript stability, translation, modification, localization, secretion, or function of a polynucleotide or polypeptide encoding human IL-1α or IL-1β. Moreover, the inhibitory polynucleotide or polypeptide composition binds to one or more region(s) of IL-1α or IL-1β comprised by SEQ ID NO: 1 and SEQ ID NO: 2 (IL-1α) or SEQ ID NO: 3 and SEQ ID NO: 4 (IL-1β). The inhibitory polynucleotide or polypeptide composition binds to one or more fragments of IL-1α or IL-1β comprised by SEQ ID NO: 1 and SEQ ID NO: 2 (IL-1a) or SEQ ID NO: 3 and SEQ ID NO: 4 (IL-1β).

A fragment, in the case of these sequences and all others provided herein, is defined as a part of the whole that is less than the whole. Moreover, a fragment ranges in size from a single nucleotide or amino acid within a polynucleotide or polypeptide sequence to one fewer nucleotide or amino acid than the entire polynucleotide or polypeptide sequence. Finally, a fragment is defined as any portion of a complete polynucleotide or polypeptide sequence that is intermediate between the extremes defined above.

Human IL-1a is encoded by the following mRNA sequence (NCBI Accession No. NM_000575 and SEQ ID NO: 1): (For all mRNA transcripts incorporated into the present application, the initiator methionine, encoded by the codon "atg," is bolded and capitalized to delineate the start of the coding region.)

```
accaggcaacaccattgaaggctcatatgtaaaaatccatgccttcctttctcccaatctccattcccaa acttagccactggcttctggctgaggccttacgcatacctcccggggcttgcacacaccttcttctacag aagacacaccttgggcatatcctacagaagaccaggcttctctctggtccttggtagagggctactttac tgtaacagggccagggtggagagttctctcctgaagctccatcccctctataggaaatgtgttgacaata ttcagaagagtaagaggatcaagacttctttgtgctcaaataccactgttctcttctctaccctgcccta accaggagcttgtcacccaaactctgaggtgatttatgccttaatcaagcaaacttccctcttcagaaa agatggctcattttccctcaaaagttgccaggagctgccaagtattctgccaattcaccctggagcacaa tcaacaaattcagccagaacacaactacagctactattagaactattattattaataaattcctctccaa atctagcccttgacttcggatttcacgatttctcccttcctcctagaaacttgataagtttcccgcgct tcccttttctaagactacatgtttgtcatcttataaagcaaaggggtgaataaatgaaccaaatcaata acttctggaatatctgcaaacaacaataatatcagctatgccatctttcactattttagccagtatcgag ttgaatgaacatagaaaaatacaaaactgaattcttccctgtaaattcccgttttgacgacgcacttgt agccacgtagccacgcctacttaagacaattacaaaaggcgaagaagactgactcaggcttaagctgcca gccagagagggagtcatttcattggcgtttgagtcagcaaagaagtcaagATGgccaaagttccagacat
```

-continued

```
gtttgaagacctgaagaactgttacagtgaaaatgaagaagacagttcctccattgatcatctgtctctg aatcagaaatccttctatcatgtaagctatggcccactccatgaaggctgcatggatcaatctgtgtctc tgagtatctctgaaacctctaaaacatccaagcttaccttcaaggagagcatggtggtagtagcaaccaa cgggaaggttctgaagaagagacggttgagtttaagccaatccatcactgatgatgacctggaggccatc gccaatgactcagaggaagaaatcatcaagcctaggtcagcaccttttagcttcctgagcaatgtgaaat acaactttatgaggatcatcaaatacgaattcatcctgaatgacgccctcaatcaaagtataattcgagc caatgatcagtacctcacggctgctgcattacataatctggatgaagcagtgaaatttgacatgggtgct tataagtcatcaaaggatgatgctaaaattaccgtgattctaagaatctcaaaaactcaattgtatgtga ctgcccaagatgaagaccaaccagtgctgctgaaggagatgcctgagatacccaaaaccatcacaggtag tgagaccaacctcctcttcttctgggaaactcacggcactaagaactatttcacatcagttgcccatcca aacttgtttattgccacaaagcaagactactgggtgtgcttggcagggggccaccctctatcactgact ttcagatactggaaaaccaggcgtaggtctggagtctcacttgtctcacttgtgcagtgttgacagttca tatgtaccatgtacatgaagaagctaaatcctttactgttagtcatttgctgagcatgtactgagccttg taattctaaatgaatgtttacactcttttgtaagagtggaaccaacactaacatataatgttgttatttaa agaacaccctatattttgcatagtaccaatcattttaattattattcttcataacaattttaggaggacc agagctactgactatggctaccaaaaagactctacccatattacagatgggcaaattaaggcataagaaa actaagaaatatgcacaatagcagttgaaacaagaagccacagacctaggatttcatgatttcatttcaa ctgtttgccttctactttttaagttgctgatgaactcttaatcaaatagcataagtttctgggacctcagt tttatcattttcaaaatggagggaataatacctaagccttcctgccgcaacagttttttatgctaatcag ggaggtcattttggtaaaatacttcttgaagccgagcctcaagatgaaggcaaagcacgaaatgttattt tttaattattatttatatatgtatttataaatatatttaagataattataatatactatatttatgggaa cccttcatcctctgagtgtgaccaggcatcctccacaatagcagacagtgttttctgggataagtaagt ttgatttcattaatacagggcattttggtccaagttgtgcttatcccatagccaggaaactctgcattct agtacttgggagacctgtaatcatataataaatgtacattaattaccttgagccagtaattggtccgatc tttgactcttttgccattaaacttacctgggcattcttgtttcaattccacctgcaatcaagtcctacaa gctaaaattagatgaactcaactttgacaaccatgagaccactgttatcaaaactttcttttctggaatg taatcaatgtttcttctaggttctaaaaattgtgatcagaccataatgttacattattatcaacaatagt gattgatagagtgttatcagtcataactaaataaagcttgcaacaaaattctctgacaaaaaaaaaaaa aaa.
```

Human IL-1α is encoded by the following amino acid sequence (NCBI Accession No. NM_000575 and SEQ ID NO: 2):

```
MAKVPDMFEDLKNCYSENEEDSSSIDHLSLNQKSFYHVSYGPLHDSE
EEIIKPRSAPFSFLSNVKYNFMRIIKYEFILNDALNQSIIRANDQYLTA
AALHNLDEAVKFDMGAYKSSKDDAKITVILRISKTQLYVTAQDEDQPV
LLKEMPEIPKTITGSETNLLFFWETHGTKNYFTSVAHPNLFIATKQDYW
VCLAGGPPSITDFQILENQA.
```

Human IL-1β is encoded by the following mRNA sequence (NCBI Accession No. NM_000576 and SEQ ID NO: 3):

```
accaaacctcttcgaggcacaaggcacaacaggctgctctgggattctcttcagccaatcttcattgctc aagtgtctgaagcagccATGgcagaagtacctgagctcgccagtgaaatgatggcttattacagtggcaa tgaggatgacttgttctttgaagctgatggccctaaacagatgaagtgctccttccaggacctggacctc tgccctctggatggcggcatccagctacgaatctccgaccaccactacagcaagggcttcaggcaggccg
```

-continued

```
cgtcagttgttgtggccatggacaagctgaggaagatgctggttccctgcccacagaccttccaggagaa tgacctgagcaccttctttcccttcatctttgaagaagaacctatcttcttcgacacatgggataacgag gcttatgtgcacgatgcacctgtacgatcactgaactgcacgctccgggactcacagcaaaaaagcttgg tgatgtctggtccatatgaactgaaagctctccacctccagggacaggatatggagcaacaagtggtgtt ctccatgtcctttgtacaaggagaagaaagtaatgacaaaatacctgtggccttgggcctcaaggaaaag aatctgtacctgtcctgcgtgttgaaagatgataagcccactctacagctggagagtgtagatcccaaaa attacccaaagaagaagatggaaaagcgatttgtcttcaacaagatagaaatcaataacaagctggaatt tgagtctgcccagttccccaactggtacatcagcacctctcaagcagaaaacatgcccgtcttcctggga gggaccaaaggcggccaggatataactgacttcaccatgcaatttgtgtcttcctaaagagagctgtacc cagagagtcctgtgctgaatgtggactcaatccctagggctggcagaaagggaacagaaaggttttttgag tacggctatagcctggactttcctgttgtctacaccaatgcccaactgcctgccttagggtagtgctaag aggatctcctgtccatcagccaggacagtcagctctctcctttcagggccaatcccagccctttttgttg agccaggcctctctcacctctcctactcacttaaagcccgcctgacagaaaccacggccacatttggttc taagaaaccctctgtcattcgctcccacattctgatgagcaaccgcttccctatttatttatttatttgt ttgtttgttttattcattggtctaatttattcaaaggggcaagaagtagcagtgtctgtaaaagagcct agttttttaatagctatggaatcaattcaatttggactggtgtgctctctttaaatcaagtcctttaatta agactgaaaatatataagctcagattatttaaatgggaatatttataaatgagcaaatatcatactgttc aatggttctgaaataaacttcactgaag.
```

Human IL-1β is encoded by the following amino acid sequence (NCBI Accession No. NM_000576 and SEQ ID NO: 4):

MAEVPELASEMMAYYSGNEDDLFFEADGPKQMKCSFQDLDLCPLDGGI

QLRISDHHYSKGFRQAASVVVAMDKLRKMLVPCPQTFQENDLSTFFPFIF

EEEPIFFDTWDNEAYVHDAPVRSLNCTLRDSQQKSLVMSGPYELKALHL

QGQDMEQQVVFSMSFVQGEESNDKIPVALGLKEKNLYLSCVLKDDKPTL

QLESVDPKNYPKKKMEKRFVFNKIEINNKLEFESAQFPNWYISTSQAEN

MPVFLGGTKGGQDITDFTMQFVSS.

Interleukin-1 Receptor (Type 1) Antagonist (IL-1Ra):

IL-1Ra is an endogenous receptor antagonist which is primarily produced by activated monocytes and tissue macrophages, inhibits the activities of the proinflammatory forms of IL-1 by competitively binding to IL-1 receptor. (Gabay, C. et al. 1997. 159: 5905-5913). IL-1Ra is an inducible gene that is typically upregulated in inflammatory conditions, such as rheumatoid arthritis (Arend, W. P. 1993. Adv Immunol. 54: 167-223).

Normal tear fluid has been found to contain high concentrations of IL-1Ra in concentrations 25,000 and 40,000 times greater than both proinflammatory forms of IL-1 (Solomon, A. et al. 2001. Invest Opthalmol V is Sci. 42: 2283-2292). The high concentration of IL-1Ra in the tear fluid may be a natural homeostatic mechanism for preventing inappropriate activation of IL-1-mediated inflammatory events on the ocular surface (Dinarello, C. A. 1996. Blood. 15:2095-2147).

An increased concentration of IL-1Ra has been detected in the tear fluid of patients with dry eye and in the conjunctival epithelium of patients with dry eye syndrome (Solomon, A. et al. 2001. Invest Opthalmol V is Sci. 42: 2283-2292). Despite this increased level of expression, the ratio of IL-1Ra to proinflammatory forms IL-1 dry-eye was significantly lower than in normal subjects. Reports of placebo-controlled clinical trials in which IL-1Ra was administered to patients with rheumatoid arthritis have noted that increasing the ratio of IL-1Ra to the proinflammatory forms significantly improves clinical symptoms (Dinarello, C. A. 2000. N Engl J. Med. 343:732-734).

In the present invention, compositions comprise one or more regions of IL-1Ra transcripts 1, 2, 3, or 4, intacellular IL-1Ra (icIL-1Ra), or their corresponding polypeptide isoforms. Alternatively, compositions comprise the entirety of IL-1Ra transcripts 1, 2, 3, or 4, intacellular IL-1Ra (icIL-1Ra), or their corresponding polypeptide isoforms. Compositions comprising any form of human IL-1Ra, or fragments thereof, inhibit the function of IL-1R1. These polynucleotides and polypeptides are defined by the following sequences.

Human IL-1Ra, transcript 1, is encoded by the following mRNA sequence (NCBI Accession No. NM_173842 and SEQ ID NO: 5):

```
atttctttataaaccacaactctgggcccgcaatggcagtccactgccttgctgcagtcacagaATGgaa atctgcagaggcctccgcagtcacctaatcactctcctcctcttcctgttccattcagagacgatctgcc gaccctctgggagaaaatccagcaagatgcaagccttcagaatctgggatgttaaccagaagaccttcta
```

-continued

```
tctgaggaacaaccaactagttgctggatacttgcaaggaccaaatgtcaatttagaagaaaagatagat
gtggtacccattgagcctcatgctctgttcttgggaatccatggagggaagatgtgcctgtcctgtgtca
agtctggtgatgagaccagactccagctggaggcagttaacatcactgacctgagcgagaacagaaagca
ggacaagcgcttcgccttcatccgctcagacagcggccccaccaccagttttgagtctgccgcctgcccc
ggttggttcctctgcacagcgatggaagctgaccagcccgtcagcctcaccaatatgcctgacgaaggcg
tcatggtcaccaaattctacttccaggaggacgagtagtactgcccaggcctgcctgttcccattcttgc
atggcaaggactgcagggactgccagtcccctgccccagggctccggctatgggggcactgaggacca
gccattgaggggtggaccctcagaaggcgtcacaagaacctggtcacaggactctgcctcctcttcaact
gaccagcctccatgctgcctccagaatggtctttctaatgtgtgaatcagagcacagcagcccctgcaca
aagcccttccatgtcgcctctgcattcaggatcaaaccccgaccacctgcccaacctgctctcctcttgc
cactgcctcttcctccctcattccaccttccatgccctggatccatcaggccacttgatgaccccaac
caagtggctcccacaccctgttttacaaaaaagaaaagaccagtccatgagggaggttttttaagggtttg
tggaaaatgaaaattaggatttcatgattttttttttcagtccccgtgaaggagagcccttcatttgga
gattatgttctttcggggagaggctgaggacttaaaatattcctgcatttgtgaaatgatggtgaaagta
agtggtagcttttccttcttttttcttctttttttgtgatgtcccaacttgtaaaaattaaaagttatgg
tactatgttagcccataatttttttttttccttttaaaacacttccataatctggactcctctgtccagg
cactgctgcccagcctccaagctccatctccactccagatttttacagctgcctgcagtactttacctc
ctatcagaagtttctcagctcccaaggctctgagcaaatgtggctcctggggggttctttcttcctctgct
gaaggaataaattgctccttgacattgtagagcttctggcacttggagacttgtatgaaagatggctgtg
cctctgcctgtctcccccaccgggctgggagctctgcagagcaggaaacatgactcgtatatgtctcagg
tccctgcagggccaagcacctagcctcgctcttggcaggtactcagcgaatgaatgctgtatatgttggg
tgcaaagttccctacttcctgtgacttcagctctgttttacaataaaatcttgaaaatgcctaaaaaaaa
aaaaaaaaa.
```

Human IL-1Ra, transcript 1, is encoded by the following amino acid sequence (NCBI Accession No. NM_173842 and SEQ ID NO: 6):

MEICRGLRSHLITLLLFLFHSETICRPSGRKSSKMQAFRIWDVNQKTFYL
RNNQLVAGYLQGPNVNLEEKIDVVPIEPHALFLGIHGGKMCLSCVKSGDE
TRLQLEAVNITDLSENRKQDKRFAFIRSDSGPTTSFESAACPGWFLCTAM
EADQPVSLTNMPDEGVMVTKFYFQEDE.

Human IL-1Ra, transcript 2, is encoded by the following mRNA sequence (NCBI Accession No. NM_173841 and SEQ ID NO: 7):

```
gggcagctccaccctgggagggactgtggcccaggtactgcccgggtgctactttatgggcagcagctca
gttgagttagagtctggaagacctcagaagacctcctgtcctatgaggccctccccATGgctttagctga
cttgtatgaagaaggaggtggaggaggaggagaaggtgaagacaatgctgactcaaaggagacgatctgc
cgaccctctgggagaaaatccagcaagatgcaagccttcagaatctgggatgttaaccagaagaccttct
atctgaggaacaaccaactagttgctggatacttgcaaggaccaaatgtcaatttagaagaaaagataga
tgtggtacccattgagcctcatgctctgttcttgggaatccatggagggaagatgtgcctgtcctgtgtc
aagtctggtgatgagaccagactccagctggaggcagttaacatcactgacctgagcgagaacagaaagc
aggacaagcgcttcgccttcatccgctcagacagcggccccaccaccagttttgagtctgccgcctgccc
cggttggttcctctgcacagcgatggaagctgaccagcccgtcagcctcaccaatatgcctgacgaaggc
gtcatggtcaccaaattctacttccaggaggacgagtagtactgcccaggcctgcctgttcccattcttg
```

-continued

```
catggcaaggactgcagggactgccagtcccctgcccagggctcccggctatgggggcactgaggacc agccattgaggggtggaccctcagaaggcgtcacaagaacctggtcacaggactctgcctcctcttcaac tgaccagcctccatgctgcctccagaatggtctttctaatgtgtgaatcagagcacagcagccctgcac aaagcccttccatgtcgcctctgcattcaggatcaaaccccgaccacctgcccaacctgctctcctcttg ccactgcctcttcctccctcattccaccttcccatgcctggatccatcaggccacttgatgaccccaa ccaagtggctcccacaccctgttttacaaaaaagaaaagaccagtccatgagggaggtttttaagggttt gtggaaaatgaaaattaggatttcatgatttttttttttcagtcccgtgaaggagagcccttcatttgg agattatgttctttcggggagaggctgaggacttaaaatattcctgcatttgtgaaatgatggtgaaagt aagtggtagcttttcccttcttttcttcttttttttgtgatgtcccaacttgtaaaaattaaaagttatg gtactatgttagccccataatttttttttcctttaaaacacttccataatctggactcctctgtccag gcactgctgcccagcctccaagctccatctccactccagatttttttacagctgcctgcagtactttacct cctatcagaagtttctcagctcccaaggctctgagcaaatgtggctcctgggggttcttcttcctctgc tgaaggaataaattgctccttgacattgtagagcttctggcacttggagacttgtatgaaagatggctgt gcctctgcctgtctccccaccgggctggagctctgcagagcaggaaacatgactcgtatatgtctcag gtccctgcagggccaagcacctagcctcgctcttggcaggtactcagcgaatgaatgctgtatatgttgg gtgcaaagttccctacttcctgtgacttcagctctgttttacaataaaatcttgaaatgcctaaaaaaa aaaaaaaaaaaaaaaaaaaaaaaaaaaaaaaaaaaaaaaa.
```

Human IL-1Ra, transcript 2, is encoded by the following amino acid sequence (NCBI Accession No. NM_173841 and SEQ ID NO: 8):

MALADLYEEGGGGGGEGEDNADSKETICRPSGRKSSKMQAFRIWDVNQKT
FYLRNNQLVAGYLQGPNVNLEEKIDVVPIEPHALFLGIHGGKMCLSCVKS

-continued

GDETRLQLEAVNITDLSENRKQDKRFAFIRSDSGPTTSFESAACPGWFLC

TAMEADQPVSLTNMPDEGVMVTKFYFQEDE.

Human IL-1Ra, transcript 3, is encoded by the following mRNA sequence (NCBI Accession No. NM_000577 and SEQ ID NO: 9):

```
gggcagctccaccctgggagggactgtggcccaggtactgcccgggtgctactttatgggcagcagctca gttgagttagagtctggaagacctcagaagacctcctgtcctatgaggccctccccATGgctttagagac gatctgccgaccctctgggagaaaatccagcaagatgcaagccttcagaatctgggatgttaaccagaag accttctatctgaggaacaaccaactagttgctggatacttgcaaggaccaaatgtcaatttagaagaaa agatagatgtggtacccattgagcctcatgctctgttcttgggaatccatggagggaagatgtgcctgtc ctgtgtcaagtctggtgatgagaccagactccagctggaggcagttaacatcactgacctgagcgagaac agaaagcaggacaagcgcttcgccttcatccgctcagacagcggccccaccaccagttttgagtctgccg cctgccccggttggttcctctgcacagcgatggaagctgaccagcccgtcagcctcaccaatatgcctga cgaaggcgtcatggtcaccaaattctacttccaggaggacgagtagtactgcccaggcctgcctgttccc attcttgcatggcaaggactgcagggactgccagtcccctgcccagggctcccggctatgggggcact gaggaccagccattgaggggtggaccctcagaaggcgtcacaagaacctggtcacaggactctgcctcct cttcaactgaccagcctccatgctgcctccagaatggtctttctaatgtgtgaatcagagcacagcagcc cctgcacaaagcccttccatgtcgcctctgcattcaggatcaaaccccgaccacctgcccaacctgctct cctcttgccactgcctcttcctccctcattccaccttcccatgcctggatccatcaggccacttgatga ccccccaaccaagtggctcccacaccctgttttacaaaaaagaaaagaccagtccatgagggaggtttta agggtttgtggaaaatgaaaattaggatttcatgatttttttttttcagtcccgtgaaggagagcccttc atttggagattatgttctttcggggagaggctgaggacttaaaatattcctgcatttgtgaaatgatgg
```

```
tgaaagtaagtggtagcttttcccttcttttcttcttttttgtgatgtcccaacttgtaaaattaaa agttatggtactatgttagccccataattttttttttccttttaaaacacttccataatctggactcctc tgtccaggcactgctgcccagcctccaagctccatctccactccagattttttacagctgcctgcagtac tttacctcctatcagaagtttctcagctcccaaggctctgagcaaatgtggctcctgggggttctttctt cctctgctgaaggaataaattgctccttgacattgtagagcttctggcacttggagacttgtatgaaaga tggctgtgcctctgcctgtctcccccaccgggctgggagctctgcagagcaggaaacatgactcgtatat gtctcaggtccctgcagggccaagcacctagcctcgctcttggcaggtactcagcgaatgaatgctgtat atgttgggtgcaaagttccctacttcctgtgacttcagctctgttttacaataaaatcttgaaaatgcct aaaaaaaaaaaaaaaaaaaaaaaaaaaaaaaaaaaaaaaaaaaaaaaa.
```

Human IL-1Ra, transcript 3, is encoded by the following amino acid sequence (NCBI Accession No. NM_000577 and SEQ ID NO: 10):

```
MALETICRPSGRKSSKMQAFRIWDVNQKTFYLRNNQLVAGYLQGPNVNLE
EKIDVVPIEPHALFLGIHGGKMCLSCVKSGDETRLQLEAVNITDLSENRK
QDKRFAFIRSDSGPTTSFESAACPGWFLCTAMEADQPVSLTNMPDEGVMV
TKFYFQEDE.
```

Human IL-1Ra, transcript 4, is encoded by the following mRNA sequence (NCBI Accession No. NM_173843 and SEQ ID NO: 11):

```
gggcagctccaccctgggagggactgtggcccaggtactgcccgggtgctactttatgggcagcagctca gttgagttagagtctggaagacctcagaagacctcctgtcctatgaggccctccccatggctttagggggg attataaaactaatcatcaaagccaagaaggcaagagcaagcatgtaccgctgaaaacacaagataactg cataagtaatgactttcagtgcagattcatagctaacccataaactgctggggcaaaaatcatcttggaa ggctctgaacctcagaaaggattcacaagacgatctgccgaccctctgggagaaaatccagcaagATGca agccttcagaatctgggatgttaaccagaagaccttctatctgaggaacaaccaactagttgctggatac ttgcaaggaccaaatgtcaatttagaagaaaagatagatgtggtacccattgagcctcatgctctgttct tgggaatccatggagggaagatgtgcctgtcctgtgtcaagtctggtgatgagaccagactccagctgga ggcagttaacatcactgacctgagcgagaacagaaagcaggacaagcgcttcgccttcatccgctcagac agcggccccaccaccagttttgagtctgccgcctgccccggttggttcctctgcacagcgatggaagctg accagcccgtcagcctcaccaatatgcctgacgaaggcgtcatggtcaccaaattctacttccaggagga cgagtagtactgcccaggcctgcctgttcccattcttgcatggcaaggactgcagggactgccagtcccc ctgccccagggctcccggctatgggggcactgaggaccagccattgagggggtggaccctcagaaggcgtc acaagaacctggtcacaggactctgcctcctcttcaactgaccagcctccatgctgcctccagaatggtc tttctaatgtgtgaatcagagcacagcagccctgcacaaagcccttccatgtcgcctctgcattcagga tcaaacccgaccacctgcccaacctgctctcctcttgccactgcctcttcctccctcattccaccttcc catgccctggatccatcaggccacttgatgaccccaaccaagtggctcccacacctgttttacaaaaa agaaaagaccagtccatgagggaggttttaaggggtttgtggaaaatgaaaattaggatttcatgatttt tttttttcagtccccgtgaaggagagcccttcatttggagattatgttctttcggggagaggctgaggac ttaaaatattcctgcatttgtgaaatgatggtgaaagtaagtggtagcttttcccttcttttcttcttt ttttgtgatgtcccaacttgtaaaaattaaaagttatggtactatgttagccccataattttttttttcc ttttaaaacacttccataatctggactcctctgtccaggcactgctgcccagcctccaagctccatctcc actccagattttttacagctgcctgcagtactttacctcctatcagaagtttctcagctcccaaggctct gagcaaatgtggctcctgggggttctttcttcctctgctgaaggaataaattgctccttgacattgtaga gcttctggcacttggagacttgtatgaaagatggctgtgcctctgcctgtctcccccaccgggctgggag
```

```
ctctgcagagcaggaaacatgactcgtatatgtctcaggtccctgcagggccaagcacctagcctcgctc ttggcaggtactcagcgaatgaatgctgtatatgttgggtgcaaagttccctacttcctgtgacttcagc tctgttttacaataaaatcttgaaaatgcctaaaaaaaaaaaaaaaaaaaaaaaaaaaaaaaaaaaaaaa aaaaaaaaaaaaa.
```

Human IL-1Ra, transcript 4, is encoded by the following amino acid sequence (NCBI Accession No. NM_173843 and SEQ ID NO: 12):

```
MQAFRIWDVNQKTFYLRNNQLVAGYLQGPNVNLEEKIDVVPIEPHALFLG

IHGGKMCLSCVKSGDETRLQLEAVNITDLSENRKQDKRFAFIRSDSGPTT

SFESAACPGWFLCTAMEADQPVSLTNMPDEGVMVTKFYFQEDE.
```

Human intracellular IL-1Ra, icIL-1Ra, is encoded by the following mRNA sequence (NCBI Accession No. M55646 and SEQ ID NO: 13):

```
agctccaccctgggagggactgtggcccaggtactgcccgggtgctactttatgggcagcagctcagttg agttagagtctggaagacctcagaagacctcctgtcctatgaggccctccccATGgctttagagacgatc tgccgaccctctgggagaaaatccagcaagatgcaagccttcagaatctgggatgttaaccagaagacct tctatctgaggaacaaccaactagttgctggatacttgcaaggaccaaatgtcaatttagaagaaaagat agatgtggtacccattgagcctcatgctctgttcttgggaatccatggagggaagatgtgcctgtcctgt gtcaagtctggtgatgagaccagactccagctggaggcagttaacatcactgacctgagcgagaacagaa agcaggacaagcgcttcgccttcatccgctcagacagtggccccaccaccagttttgagtctgccgcctg ccccggttggttcctctgcacagcgatggaagctgaccagcccgtcagcctcaccaatatgcctgacgaa ggcgtcatggtcaccaaattctacttccaggaggacgagtag.
```

Human intracellular IL-1Ra, icIL-1Ra, is encoded by the following amino acid sequence (NCBI Accession No. M55646 and SEQ ID NO: 14):

```
MALETICRPSGRKSSKMQAFRIWDVNQKTFYLRNNQLVAGYLQGPNVNLE

EKIDVVPIEPHALFLGIHGGKMCLSCVKSGDETRLQLEAVNITDLSENRK

QDKRFAFIRSDSGPTTSFESAACPGWFLCTAMEADQPVSLTNMPDEGVM

VTKFYFQEDE.
```

Human Recombinant IL-1Ra:

A recombinant form of human IL-1Ra (rHuIL-1Ra) was developed and tested in animal models for arthritis. This form of rHuIL-1Ra is also known as Anakinra or KINERET® differs from the native nonglycosylated IL-1Ra by the addition of an N-terminal methionine. It binds to IL-1R type I with the same affinity as IL-1β. KINERET® consists of 153 amino acids and has a molecular weight of 17.3 kilodaltons. It is produced by recombinant DNA technology using an E. coli bacterial expression system.

Anakinra has been investigated in several conditions considered mediated at least in part via IL-1. Some evidence suggests involvement of IL-1 in the pathogenesis of rheumatoid arthritis and septic shock (Jiang, Y. et al. 2000. Arthritis Rheum. 43:1001-1009; Fisher, C. J. et al. 1994. JAMA. 271:1836-1843; Okusawa, S. et al. 1988. J Clin Invest. 81:1162-1172; Bresnihan, B. et al. 1998. Rheum Dis Clin North Am. 24(3):615-628; Dayer, J. M. et al. 2001. Curr Opin Rheumatol. 13:170-176; Edwards, C. K. 2001. J Clin Rheumatol. 7:S17-S24). Anakinra has been approved by the FDA for the reduction in signs and symptoms of moderately to severely active rheumatoid arthritis in patients 18 years of age or older who have failed one or more disease-modifying antirheumatic drugs. Considering its high safety profile, administration of Anakinra has also been used in the treatment of arthritis in patients with Juvenile rheumatoid arthritis (Reiff, A. 2005. Curr Rheumatol Rep. 7:434-40). Other indications include prevention of graft-versus-host disease (GVHD) after bone marrow transplantation (Antin, J. H. et al. 1994. Blood. 84:1342-8), uveitis (Teoh, S. C. et al. 2007. Br J Opthalmol. 91: 263-4) osteoarthritis (Caron, J. P. et al. 1996. Arthritis Rheum. 39:1535-44), asthma, inflammatory bowel disease, acute pancreatitis (Hynninen, M. et al. 1999. J Crit. Care. 14:63-8), psoriasis, and type II diabetes mellitus (Larsen, C. M. et al. 2007. N Engl J. Med. 356:1517-26). The systemic safety profile of IL-1Ra is extremely favorable, especially in comparison to other immunosuppressive treatments such as TNF-α blockers, cytotoxic agents, or even steroids.

Topical human recombinant IL-1Ra has been successfully used for prevention of corneal transplant rejection (Yamada, J. et al. 2000. Invest Opthalmol V is Sci. 41:4203-8) and allergic conjunctivitis (Keane-Myers, A. M. et al. 1999. Invest Opthalmol V is Sci. 40:3041-6) in experimental animal models. Similarly, using topical IL-1Ra significantly decreases corneal inflammation and leads to enhanced corneal transparency in the rat model of corneal alkali injury (Yamada, J. et al. 2003. Exp Eye Res. 76:161-7).

A recombinant form of human IL-1Ra (rHuIL-1Ra) was developed and approved for use in humans by subcutaneous injection for the treatment of arthritis. This form of rHuIL-1Ra, also known as Anakinra or KINERET® (Amgen Inc.), differs from the native nonglycosylated IL-1Ra by the addition of an N-terminal methionine. It binds to human IL-1R, type 1, (IL-1R1) with the same affinity as IL-1β. KINERET® consists of 153 amino acids (see SEQ ID NO: 16) and has a molecular weight of 17.3 kilodaltons. It is produced by recombinant DNA technology using an E coli bacterial expression system. This composition comprises one or more regions of SEQ ID NO: 15 or SEQ ID NO: 16. Furthermore, this composition comprises the entire sequence of either SEQ ID NO: 15 or SEQ ID NO: 16.

Anakinra/KINERET® is encoded by the following mRNA sequence (NCBI Accession No. M55646 and SEQ ID NO: 15):

```
agctccaccctgggagggactgtggcccaggtactgcccgggtgctactttatgggcagcagctcagttg agttagagtctggaagacctcagaagacctcctgtcctatgaggccctccccATGgctttagagacgatc tgccgaccctctgggagaaaatccagcaagatgcaagccttcagaatctgggatgttaaccagaagacct tctatctgaggaacaaccaactagttgctggatacttgcaaggaccaaatgtcaatttagaagaaaagat agatgtggtacccattgagcctcatgctctgttcttgggaatccatggagggaagatgtgcctgtcctgt gtcaagtctggtgatgagaccagactccagctggaggcagttaacatcactgacctgagcgagaacagaa agcaggacaagcgcttcgccttcatccgctcagacagtggccccaccaccagttttgagtctgccgcctg ccccggttggttcctctgcacagcgatggaagctgaccagcccgtcagcctcaccaatatgcctgacgaa ggcgtcatggtcaccaaattctacttccaggaggacgagtag.
```

Anakinra/KINERET® is encoded by the following polypeptide sequence (DrugBank Accession No. BTD00060 and SEQ ID NO: 16):

```
MRPSGRKSSKMQAFRIWDVNQKTFYLRNNQLVAGYLQGPNVNLEEKIDVV

PIEPHALFLGIHGGKMCLSCVKSGDETRLQLEAVNITDLSENRKQDKRFA

FIRSDSGPTTSFESAACPGWFLCTAMEADQPVSLTNMPDEGVMVTKFYFQ

EDE
```

IL-1 Receptors:

The composition of the present invention comprises a polynucleotide, a polypeptide, an antibody, a compound, or a small molecule with means to inhibit the transcription, transcript stability, translation, modification, localization, secretion, or function of a polynucleotide or polypeptide encoding the IL-1 receptor, either type 1 or 2. In the present application the IL-1 Receptor, type 1 (IL-1R1), is defined by the polynucleotide sequence of SEQ ID NO: 17 or the polypeptide sequence of SEQ ID NO: 18. In the present application the IL-1 Receptor, type 2 (IL-1R2), transcript variants 1 and 2, are defined by the polynucleotide sequences of SEQ ID NO: 19 and 20, or the polypeptide sequence of SEQ ID NO: 21. IL-1R2 can function as a "decoy" receptor which binds IL-1 cytokines and inhibits IL-1R1. Polynucleotide or polypeptide compositions bind to one or more region(s) of IL-1R1 or IL-1R2, and associated isoforms, comprised by SEQ ID NO: 17-21.

IL-1R1 is encoded by the following mRNA sequence (NCBI Accession No. NM_000877 and SEQ ID NO: 17):

```
tagacgcaccctctgaagatggtgactccctcctgagaagctggacccttggtaaaagacaaggccttc tccaagaagaatATGaaagtgttactcagacttatttgtttcatagctctactgatttcttctctggagg ctgataaatgcaaggaacgtgaagaaaaataattttagtgtcatctgcaaatgaaattgatgttcgtcc ctgtcctcttaacccaaatgaacacaaaggcactataacttggtataaagatgacagcaagacacctgta tctacagaacaagcctccaggattcatcaacacaaagagaaactttggtttgttcctgctaaggtggagg attcaggacattactattgcgtggtaagaaattcatcttactgcctcagaattaaaataagtgcaaaatt tgtggagaatgagcctaacttatgttataatgcacaagccatatttaagcagaaactacccgttgcagga gacggaggacttgtgtgcccttatatggagttttttaaaaatgaaaataatgagttacctaaattacagt ggtataaggattgcaaacctctacttcttgacaatatacactttagtggagtcaaagataggctcatcgt gatgaatgtggctgaaaagcatagagggaactatacttgtcatgcatcctacacatacttgggcaagcaa tatcctattacccgggtaatagaatttattactctagaggaaaacaaaccacaaggcctgtgattgtga gcccagctaatgagacaatggaagtagacttgggatcccagatacaattgatctgtaatgtcaccggcca gttgagtgacattgcttactggaagtggaatgggtcagtaattgatgaagatgacccagtgctagggaa gactattacagtgtggaaaatcctgcaaacaaaagaaggagtaccctcatcacagtgcttaatatatcgg aaattgaaagtagatttttataaacatccatttacctgttttgccaagaatacacatggtatagatgcagc atatatccagttaatatatccagtcactaatttccagaagcacatgattggtatatgtgtcacgttgaca gtcataattgtgtgttctgttttcatctataaaatcttcaagattgacattgtgctttggtacagggatt cctgctatgattttctcccaataaaagcttcagatggaaagacctatgacgcatatatactgtatccaaa gactgttggggaagggtctacctctgactgtgatattttttgtgtttaaagtcttgcctgaggtcttggaa aaacagtgtggatataagctgttcatttatggaagggatgactacgttggggaagacattgttgaggtca
```

-continued ttaatgaaaacgtaaagaaaagcagaagactgattatcattttagtcagagaaacatcaggcttcagctg gctgggtggttcatctgaagagcaaatagccatgtataatgctcttgttcaggatggaattaaagttgtc ctgcttgagctggagaaaatccaagactatgagaaaatgccagaatcgattaaattcattaagcagaaac atggggctatccgctggtcaggggactttacacagggaccacagtctgcaaagacaaggttctggaagaa tgtcaggtaccacatgccagtccagcgacggtcaccttcatctaaacaccagttactgtcaccagccact aaggagaaactgcaaagagaggctcacgtgcctctcgggtagcatggagaagttgccaagagttctttag gtgcctcctgtcttatggcgttgcaggccaggttatgcctcatgctgacttgcagagttcatggaatgta actatatcatcctttatccctgaggtcacctggaatcagattattaagggaataagccatgacgtcaata gcagcccagggcacttcagagtagagggcttgggaagatcttttaaaaaggcagtaggcccggtgtggtg gctcacgcctataatcccagcactttgggaggctgaagtgggtggatcaccagaggtcaggagttcgaga ccagcccagccaacatggcaaaaccccatctctactaaaaatacaaaaatgagctaggcatggtggcaca cgcctgtaatcccagctacacctgaggctgaggcaggagaattgcttgaaccggggagacggaggttgca gtgagccgagtttgggccactgcactctagcctggcaacagagcaagactccgtctcaaaaaaagggcaa taaatgccctctctgaatgtttgaactgccaagaaaggcatggagacagcgaactagaagaaagggcaa gaaggaaatagccaccgtctacagatggcttagttaagtcatccacagcccaagggcggggctatgcctt gtctggggaccctgtagagtcactgaccctggagcggctctcctgagaggtgctgcaggcaaagtgagac tgacacctcactgaggaagggagacatattcttggagaacttttccatctgcttgtattttccatacacat ccccagccagaagttagtgtccgaagaccgaatttttattttacagagcttgaaaactcacttcaatgaac aaagggattctccaggattccaaagttttgaagtcatcttagctttccacaggagggagagaacttaaaa aagcaacagtagcagggaattgatccacttcttaatgctttcctccctggcatgaccatcctgtcctttg ttattatcctgcattttacgtctttggaggaacagctccctagtggcttcctccgtctgcaatgtccctt gcacagcccacacatgaaccatccttcccatgatgccgctcttctgtcatcccgctcctgctgaaacacc tcccaggggctccacctgttcaggagctgaagcccatgctttcccaccagcatgtcactcccagaccacc tccctgcctgtcctccagcttcccctcgctgtcctgctgtgtgaattcccaggttggcctggtggccat gtcgcctgcccccagcactcctctgtctctgctcttgcctcgacccttcctcctcctttgcctaggaggc cttctcgcatttttctctagctgatcagaattttaccaaaattcagaacatcctccaattccacagtctct gggagactttcccctaagaggcgacttcctctccagccttctctctctggtcaggccactgcagagatgg tggtgagcacatctgggaggctggtctccctccagctggaattgctgctctctgagggagaggctgtggt ggctgtctctgtccctcactgccttccaggagcaatttgcacatgtaacatagatttatgtaatgcttta tgtttaaaaacattccccaattatcttatttaattttttgcaattattctaattttatatatagagaaagt gacctatttttttaaaaaaatcacactctaagttctattgaacctaggacttgagcctccatttctggctt ctagtctggtgttctgagtacttgatttcaggtcaataacggtccccctcactccacactggcacgttt gtgagaagaaatgacattttgctaggaagtgaccgagtctaggaatgcttttattcaagacaccaaattc caaacttctaaatgttggaattttcaaaaattgtgtttagattttatgaaaaactcttctactttcatct attctttccctagaggcaaacattcttaaaatgtttcattttcattaaaaatgaaagccaaatttatat gccaccgattgcaggacacaagcacagttttaagagttgtatgaacatggagaggacttttggtttttat atttctcgtatttaatatgggtgaacaccaacttttatttggaataataattttcctcctaaacaaaaac acattgagtttaagtctctgactcttgcctttccacctgctttctcctgggcccgctttgcctgcttgaa ggaacagtgctgttctggagctgctgttccaacagacagggcctagctttcatttgacacacagactaca gccagaagcccatggagcagggatgtcacgtcttgaaaagcctattagatgttttacaaatttaattttg cagattattttagtctgtcatccagaaaatgtgtcagcatgcatagtgctaagaaagcaagccaatttgg -continued

```
aaacttaggttagtgacaaaattggccagagagtgggggtgatgatgaccaagaattacaagtagaatgg cagctggaatttaaggagggacaagaatcaatggataagcgtgggtggaggaagatccaaacagaaaagt gcaaagttattccccatcttccaagggttgaattctggaggaagaagacacattcctagttccccgtgaa cttcctttgacttattgtccccactaaaacaaaacaaaaaacttttaatgccttccacattaattagatt ttcttgcagttttttatggcatttttttaaagatgccctaagtgttgaagaagagtttgcaaatgcaac aaaatatttaattaccggttgttaaaactggtttagcacaatttatattttccctctcttgcctttctta tttgcaataaaaggtattgagccattttttaaatgacattttgataaattatgtttgtactagttgatg aaggagttttttttaacctgtttatataattttgcagcagaagccaaatttttgtatattaaagcacca aattcatgtacagcatgcatcacggatcaatagactgtacttattttccaataaaattttcaaactttgt actgttaaa.
```

IL-1R1 is encoded by the following amino acid sequence (NCBI Accession No. NM_000877 and SEQ ID NO: 18):

```
MKVLLRLICFIALLISSLEADKCKEREEKIILVSSANEIDVRPCPLNPNEHKGTITWYKDDS

KTPVSTEQASRIHQHKEKLWFVPAKVEDSGHYYCVVRNSSYCLRIKISAKFVENEPNLC

YNAQAIFKQKLPVAGDGGLVCPYMEFFKNENNELPKLQWYKDCKPLLLDNIHFSGVKD

RLIVMNVAEKHRGNYTCHASYTYLGKQYPITRVIEFITLEENKPTRPVIVSPANETMEVD

LGSQIQLICNVTGQLSDIAYWKWNGSVIDEDDPVLGEDYYSVENPANKRRSTLITVLNIS

EIESRFYKHPFTCFAKNTHGIDAAYIQLIYPVTNFQKHMIGICVTLTVIIVCSVFIYKIFKIDI

VLWYRDSCYDFLPIKASDGKTYDAYILYPKTVGEGSTSDCDIFVFKVLPEVLEKQCGYK

LFIYGRDDYVGEDIVEVINENVKKSRRLIIILVRETSGFSWLGGSSEEQIAMYNALVQDGI

KVVLLELEKIQDYEKMPESIKFIKQKHGAIRWSGDFTQGPQSAKTRFWKNVRYHMPVQ

RRSPSSKHQLLSPATKEKLQREAHVPLG.
```

IL-1R2, transcript variant 1, is encoded by the following mRNA sequence (NCBI Accession No. NM_004633 and SEQ ID NO: 19):

```
cccgtgaggaggaaaaggtgtgtccgctgccacccagtgtgagcgggtgacaccacccggttaggaaatc ccagctcccaagagggtataaatccctgctttactgctgagctcctgctggaggtgaaagtctggcctgg cagccttccccaggtgagcagcaacaaggccacgtgctgctgggtctcagtcctccacttcccgtgtcct ctggaagttgtcaggagcaATGttgcgcttgtacgtgttggtaatgggagtttctgccttcacccttcag cctgcggcacacacaggggctgccagaagctgccggtttcgtgggaggcattacaagcgggagttcaggc tggaaggggagcctgtagccctgaggtgcccccaggtgccctactggttgtgggcctctgtcagccccg catcaacctgacatggcataaaaatgactctgctaggacggtcccaggagaagaagagacacggatgtgg gcccaggacggtgctctgtggcttctgccagccttgcaggaggactctggcacctacgtctgcactacta gaaatgcttcttactgtgacaaaatgtccattgagctcagagttttttgagaatacagatgctttcctgcc gttcatctcatacccgcaaattttaaccttgtcaacctctggggtattagtatgccctgacctgagtgaa ttcacccgtgacaaaactgacgtgaagattcaatggtacaaggattctcttcttttggataaagacaatg agaaatttctaagtgtgagggggaccactcacttactcgtacacgatgtggccctggaagatgctggcta ttaccgctgtgtcctgacatttgcccatgaaggccagcaatacaacatcactaggagtattgagctacgc atcaagaaaaaaaagaagagaccattcctgtgatcatttcccccctcaagaccatatcagcttctctgg
```

-continued
```
ggtcaagactgacaatcccgtgtaaggtgtttctgggaaccggcacacccttaaccaccatgctgtggtg gacggccaatgacacccacatagagagcgcctacccgggaggccgcgtgaccgaggggccacgccaggaa tattcagaaaataatgagaactacattgaagtgccattgattttttgatcctgtcacaagagaggatttgc acatggattttaaatgtgttgtccataatacccctgagttttcagacactacgcaccacagtcaaggaagc ctcctccacgttctcctggggcattgtgctggccccactttcactggccttcttggttttgggggggaata tggatgcacagacggtgcaaacacagaactggaaaagcagatggtctgactgtgctatggcctcatcatc aagactttcaatcctatcccaagtgaaataaatggaatgaaataattcaaacacaaaaaaaaaaaaaaaa aaaaaaaaaaaaaa.
```

IL-1R2, transcript variant 2, is encoded by the following mRNA sequence (NCBI Accession No. NM_173343 and SEQ ID NO: 20):

```
gggatgggagatactgttgtggtcacctctggaaaatacattctgctactcttaaaaactagtgacgctc atacaaatcaacagaaagagcttctgaaggaagactttaaagctgcttctgccacgtgctgctgggtctc agtcctccacttcccgtgtcctctggaagttgtcaggagcaATGttgcgcttgtacgtgttggtaatggg agtttctgccttcacccttcagcctgcggcacacacaggggctgccagaagctgccggtttcgtgggagg cattacaagcgggagttcaggctgaaggggagcctgtagccctgaggtgccccaggtgccctactggt tgtgggcctctgtcagccccgcatcaacctgacatggcataaaaatgactctgctaggacggtcccagg agaagaagacacggatgtgggcccaggacggtgctctgtggcttctgccagccttgcaggaggactct ggcacctacgtctgcactactagaaatgcttcttactgtgacaaaatgtccattgagctcagagttttg agaatacagatgctttcctgccgttcatctcatacccgcaaattttaaccttgtcaacctctggggtatt agtatgccctgacctgagtgaattcacccgtgacaaaactgacgtgaagattcaatggtacaaggattct cttcttttggataaagacaatgagaaatttctaagtgtgaggggggaccactcacttactcgtacacgatg tggccctggaagatgctggctattaccgctgtgtcctgacatttgcccatgaaggccagcaatacaacat cactaggagtattgagctacgcatcaagaaaaaaaagaagagaccattcctgtgatcatttccccctc aagaccatatcagcttctctggggtcaagactgacaatcccgtgtaaggtgtttctgggaaccggcacac ccttaaccaccatgctgtggtggacggccaatgacacccacatagagagcgcctacccgggaggccgcgt gaccgaggggccacgccaggaatattcagaaaataatgagaactacattgaagtgccattgattttgat cctgtcacaagagaggatttgcacatggattttaaatgtgttgtccataatacccctgagttttcagacac tacgcaccacagtcaaggaagcctcctccacgttctcctggggcattgtgctggccccactttcactggc cttcttggttttgggggggaatatggatgcacagacggtgcaaacacagaactggaaaagcagatggtctg actgtgctatggcctcatcatcaagactttcaatcctatcccaagtgaaataaatggaatgaaataattc aaacacaaaaaaaaaaaaaaaaaaaaaaaaaaaaaaaa.
```

IL-1R2, transcript variants 1 and 2, are encoded by the following amino acid sequence (NCBI Accession No. NM_004633, NM_173343, and SEQ ID NO: 21):

MLRLYVLVMGVSAFTLQPAAHTGAARSCRFRGRHYKREFRLEGEPVALR

CPQVPYWLWASVSPRINLTWHKNDSARTVPGEEETRMWAQDGALWLLP

ALQEDSGTYVCTTRNASYCDKMSIELRVFENTDAFLPPFISYPQILTLST

SGVLVCPDLSEFTRDKTDVKIQWYKDSLLLDKDNEKFLSVRGTTHLLV

HDVALEDAGYYRCVLTFAHEGQQYNITRSIELRIKKKKEETIPVIISPL

KTISASLGSRLTIPCKVFLGTGTPLTTMLWWTANDTHIESAYPGGRV

TEGPRQEYSENNENYIEVPLIFDPVTREDLHMDFKCVVHNTLSFQTL

RTTVKEASSTFSWGIVLAPLSLAFLVLGGIWMHRRCKHRTGKADGL

TVLWPHHQDFQSYPK.

Interleukin-1 Receptor (type 2) Antagonist (IL-1Ra3):

The present invention comprises compositions with means to inhibit or enhance the activity of the human IL-1R2. Compositions that comprise the IL-1R2 antagonist, IL-1Ra3, have either agonist or antagonist activity regarding the efficacy of IL-1R1 function. The composition comprises a polynucleotide, a polypeptide, an antibody, a compound, or a small molecule with means to inhibit the transcription, transcript stability, translation, modification, localization, secretion, or function of a polynucleotide or polypeptide encoding IL-1Ra3. The inhibitory polynucleotide or polypeptide composition binds to one or more region(s) of IL-1Ra3 comprised by SEQ ID NO: 22 and SEQ ID NO: 23.

IL-1Ra3 is encoded by a region or the entirety of the following mRNA sequence (NCBI Accession No. AF_057168 and SEQ ID NO: 22): (for this sequence, the bolded and capitalized codon does not encode methionine, but rather represents the codon that encodes the first amino acid of the corresponding polypeptide)

```
cagaagacctcctgtcctatgaggccctccccatggctttaggtaagctccttccactctcattttttca
cctgagaaatgagagaggaaaatgtctacaattggtgtttatcaaatgctttcaggctctggtgagcaag
cgtccaggaaaatgtcaagcgcatggagctccaggcctgtctggggatctgggcacggggaggcatcca
tgggagaccatgcaggcactctgaggcaggggctgcaagctagtgcctgctggggcagcaggtgaacaga
gaggtgtaactgctgtgacagaagtcatggagtccttggagtgtgagggtcattttccactgttgataga
atagggaaattggtgaaatagccctgttaaatgagagaaagaacagtgtgagctcaatgagaaatactaa
tagaatgtggcactgagccacaaggtctgagggttgattgataaggaagggtggggactgtggagaatta
agggcttggcacaggtcagttccaccagttgtcacaagagaatgcaggctcaggtggccagaacttctcg
cttttccagaagagtccgatattctgatttcattatatatagtattctgattaaaccagacaataaagca
agcagataaaatatttaaagtataagctgccagtttgcaacctccggttaggatttgtgtggggcaaaga
aaaaaactctcaggatcattggtatgtagactctaattttaagtttctaatttaaaattggcccctgagg
ctgggcgtggtggctcacacctgtaatcccagcattttgggaggccaaggtgggtggatctcttgaggtc
aagagttcaaggcctgcctggccaacatggtgaaaccctgtctctattaaaaatacaaaaattagctggg
catggtggtgcatgtctgcaatcttagctacttgggtagctaaggcaggagaattgctggaacccgggag
gtagaggttgcagtgaatggagatcacaccactgcactccagtctgggcaatagagagagacgctctctc
taaaaaaaatatgtaaagataaataaaatgaaataaaataggcctctaatgagcaggccattctcctt
ctgggtcttactttccttgcactccttctgggtgttaagaggaggtctagaggaagctggacaactctt
agcttgtagtaagcacagtggaagtatcagctcttaatgggtcatggacacgttacgaagctaggcgccg
tgctgagcactttacatggtttatcccactgaaccctctcaataacctatgaggaagggctattattgc
tcacattttcagaagaggaaatggatatagagagattagataatttgcccatggccagacagctagtata
agaggaggaggtggattgactgcagacattctgtcttcaaaccactacactatgctatggaggcacagag
acttaatgaaatcatggagaggggaattgctttgtcaaccacaagcagttattccggggcagcagatcc
tcccctgtcccccagtggtacaatggtccctggtgggttgtgctacaatgttagcccatggtcttatgtg
tttttcaaatgtgtaaagtaggatgctggaaccactcttagaaccagataccaatacattgtgaagaaat
aaatctctgtgcttaaaactggttcatcccaaaatattttgaactgacacacaataggtgctaaataaat
gtgtgttaacttgaattggattgaattcgggaaaaaagtgcaataagcttagtgaagacaccatgttccc
tgggtagaggaaccacattctccatctaaggccaggagtatgggaggtatcaatgtttgcccagcacaga
acagggtgccaagaagagaaaagttgacggggtgcatactctgactggaaactggaagggtgagaacaga
gggtaaaggatagagatggaaccatgtgcatacactttgtgttaccttggacaagtcattcatttctctg
gacctctgctttctctctacacaatggggtcccaccacttcccttacagctgacttgtatgaagaaggag
gtggaggaggaggagaaggtgaagacaatgCTGactcaaagggtaaattattttttaggatccaagtttga
aaacaattttaggctactagatatgaacaacatcttgattatgtagttgaaggaaattaaagatgaatgg
tttaattaaaaattaatcagaatgaaaacgattgattactaatatatctgcaatggtttattttcctgag
tggcagactcactaaggttttgaatactcctgtgtgattgctctatgtatgtatgtatgtatgta
tgcatgtatctatctatctgttgtctaatagaatggatcacatctctgctaataaaaacactacactggc
agggtacaattataatcattaactgtgcctggaatttgcagcagcagccaccagaggtaccagtgccctt
```

-continued

```
taagggttcataatttagaataatccaattatctgagttttcagggactgaggggtttggcaaggtgta gaactttcagtaataaagtcaagaaagtcctggacaaaccaaggtagttggtcactctagtccataacca ggtaaagagctttccctgtaacctgtgtaaggttttagaatcatttctttccttattaccaaaaatcctc cccaaattttcaagaaattatgaactaaatagttactctatgagataggagttcagcccaaaagaaacac cataagaacaaatataattcttgcttatgttaaccatgcaatgaagcagagagaaaaagtcagtggcctc tttaggaggactgtagtgtgggaagaaataactaaactgggtttcaatcctggcctggccaggatctgga gcaagtgagttaatctttctaagccttgagtagtttataaaagaatggccactccatagacagagtagcc tgaaccttgagttcttctataaagtcactatgaatttatactcattttgaaagtgggtgtcaatatgtct gtccactttgcacagctgttatgtggacaaaaggagatctgtgtgaaagtgtaacacagagcctaaacta taacaggtaagcaacacagttgtccct.
```

One or more isoforms of IL-1Ra3 comprise the following amino acid sequence (NCBI Accession No. AF_057168 and SEQ ID NO: 23):

DLYEEGGGGGEGEDNADSK.

Interleukin-1 Receptor Accessory Protein (IL-1RAP):

Compositions that inhibit the activity of human IL-1RAP inhibit IL-1RAP binding to an IL-1 cytokine or an IL-1 receptor, and subsequent transduction of downstream intracellular signals. Compositions that comprise an inhibitor of IL-1RAP function antagonize the activity of an IL-1 receptor. The composition comprises a polynucleotide, a polypeptide, an antibody, a compound, or a small molecule with means to inhibit the transcription, transcript stability, translation, modification, localization, secretion, or function of a polynucleotide or polypeptide encoding IL-1RAP. The inhibitory polynucleotide or polypeptide composition binds to one or more region(s) of IL-1RAP, and associated isoforms, comprised by SEQ ID NO: 24-27.

IL-1RAP, transcript variant 1, is encoded by the following mRNA sequence (NCBI Accession No. NM_002182 and SEQ ID NO: 24):

```
tgccgggatccaggtctccggggtccgctttggccagaggcgcggaaggaagcagtgcccggcgacactg cacccatcccggctgcttttgctgcgccctctcagcttcccaagaaaggcatcgtcatgtgatcatcacc taagaactagaacatcagcaggccctagaagcctcactcttgcccctcccttaatatctcaaaggATGa cacttctgtggtgtgtagtgagtctctacttttatggaatcctgcaaagtgatgcctcagaacgctgcga tgactggggactagacaccatgaggcaaatccaagtgtttgaagatgagccagctcgcatcaagtgccca ctctttgaacacttcttgaaattcaactacagcacagcccattcagctggccttactctgatctggtatt ggactaggcaggacccgggaccttgaggagccaattaacttccgcctccccgagaaccgcattagtaagga gaaagatgtgctgtggttccggcccactctcctcaatgacactggcaactatacctgcatgttaaggaac actacatattgcagcaaagttgcatttcccttggaagttgttcaaaaagacagctgtttcaattccccca tgaaactcccagtgcataaactgtatatagaatatggcattcagaggatcacttgtccaaatgtagatgg atattttccttccagtgtcaaaccgactatcacttggtatatgggctgttataaaatacagaattttaat aatgtaatacccgaaggtatgaacttgagtttcctcattgccttaatttcaaataatggaaattacacat gtgttgttacatatccagaaaatggacgtacgtttcatctcaccaggactctgactgtaaaggtagtagg ctctccaaaaaatgcagtgcccctgtgatccattcacctaatgatcatgtggtctatgagaaagaacca ggagaggagctactcattccctgtacggtctattttagttttctgatggattctcgcaatgaggtttggt ggaccattgatggaaaaaaacctgatgacatcactattgatgtcaccattaacgaaagtataagtcatag tagaacagaagatgaaacaagaactcagattttgagcatcaagaaagttacctctgaggatctcaagcgc agctatgtctgtcatgctagaagtgccaaaggcgaagttccaaagcagccaaggtgaagcagaaagtgcc agctccaagatacacagtggaactggcttgtggttttggagccacagtcctgctagtggtgattctcatt gttgtttaccatgtttactggctagagatggtcctattttaccgggctcattttggaacagatgaaacca ttttagatggaaaagagtatgatatttatgtatcctatgcaaggaatgcggaagaagaagaatttgtatt
```

-continued

```
actgaccctccgtggagttttggagaatgaatttggatacaagctgtgcatctttgaccgagacagtctg cctggggaattgtcacagatgagactttgagcttcattcagaaaagcagacgcctcctggttgttctaa gccccaactacgtgctccagggaacccaagccctcctggagctcaaggctggcctagaaaatatggcctc tcggggcaacatcaacgtcattttagtacagtacaaagctgtgaaggaaacgaaggtgaaagagctgaag agggctaagacggtgctcacggtcattaaatggaaagggaaaaatccaagtatccacagggcaggttct ggaagcagctgcaggtggccatgccagtgaagaaaagtcccaggcggtctagcagtgatgagcagggcct ctcgtattcatctttgaaaaatgtatgaaaggaataatgaaaagggtaaaaagaacaaggggtgctccag gaagaaagagtcccccagtcttcattcgcagtttatggtttcataggcaaaataatggtctaagcctc ccaatagggataaatttagggtgactgtgtggctgactattctgcttcctcaggcaacactaaagtttag aaagatatcatcaacgttctgtcaccagtctctgatgccactatgttctttgcaggcaaagacttgttca atgcgaatttccccttctacattgtctatccctgtttttatatgtctccattcttttttaaaatcttaaca tatggagcagccttcctatgaatttaaatatgcctttaaaataagtcactgttgacagggtcatgagtt tccgagtatagttttctttttatcttattttactcgtccgttgaaaagataatcaaggcctacatttta gctgaggataatgaacttttttcctcattcggctgtataatacataaccacagcaagactgacatccact taggatgatacaaagcagtgtaactgaaaatgtttcttttaattgatttaaaggacttgtcttctatacc acccttgtcctcatctcaggtaatttatgaaatctatgtaaacttgaaaaatatttcttaatttttgttt ttgctccagtcaattcctgattatccacaggtcaacccacattttttcattccttctccctatctgctta tatcgcattgctcatttagagtttgcaggaggctccatactaggttcagtctgaaagaaatctcctaatg gtgctatagagagggaggtaacagaaagactcttttagggcattttttctgactcatgaaaagagcacaga aaaggatgtttggcaatttgtcttttaagtcttaaccttgctaatgtgaatactgggaaagtgatttttt ctcactcgttttttgttgctccattgtaaagggcggaggtcagtcttagtggccttgagagttgcttttgg cattaatattctaagagaattaactgtatttcctgtcacctattcactagtgcaggaaatatacttgctc caaataagtcagtatgagaagtcactgtcaatgaaagttgttttgtttgttttcagtaatattttgctgt ttttaagacttggaaaactaagtgcagagtttacagagtggtaaatatctatgttacatgtagattatac atatatatacacacgtgtatatgagatatatatcttatatctccacaaacacaaattatatatatacata tccacacacatacattacatatatctgtgtatataaatccacatgcacatgaaatatatatatatatata atttgtgtgtgtgtatgtgtatgtatatgactttaaatagctatgggtacaatattaaaaaccactggaa ctcttgtccagttttaaattatgtttttactggaatgttttgtgtcagtgttttctgtacatattatt tgttaattcacagctcacagagtgatagttgtcatagttcttgccttccctaagtttatataaataactt aagtattgctacagtttatctaggttgcagtggcatctgctgtgcacagagcttccatggtcactgctaa gcagtagccagccatcgggcattaattgatttcctactatattcccagcagacacatttagaaactaagc tatgttaacctcagtgctcaactatttgaactgttgagtgataaaggaaacaaatataactgtaaatgaa tcttggtatcctgtgaaacagaataattcgtaatttaagaaagcccttatcccggtaacatgaatgttga tgaacaaatgtaaaattatatcctatatttaagtacccataataaatcatttccctctataagtgttatt gattattttaaattgaaaaagtttcacttggatgaaaaaagtagaaaagtaggtcattcttggatctac tttttttttagccttattaatatttttccctattagaaaccacaattactccctctattaacccttcactt actagaccagaaagaacttattccagataagctttgaatatcaattcttacataaactttaggcaaaca gggaatagtctagtcaccaaaggaccattctcttgccaatgctgcattccttttgcacttttggattcca tatttatcccaaatgctgttgggcaccectagaaataccttgatgttttttctatttatatgcctgcctt tggtacttaattttacaaatgctgtaatataaagcatatcaagtttatgtgatacgtatcattgcaagag
```

```
-continued
aatttgtttcaagatttttttttaatgttccagaagatggccaatagagaacattcaagggaaatgggga aacataatttagagaacaagaacaaaccatgtctcaaatttttttaaaaaaaattaatggttttaaatat atgctatagggacgttccatgcccaggttaacaaagaactgtgatatatagagtgtctaattacaaaatc atatacgatttatttaattctcttctgtattgtaacttagatgattcccaaggactctaataaaaaatca cttcattgtatttggaaacaaaaacatcattcattaattacttattttctttccataggttttaatattt tgagagtgtctttttttatttcattcatgaacttttgtattttcattttcatttgatttgtaaatttac ttatgttaaaaataaaccatttattttcagctttg.
```

IL-1RAP, transcript variant 1, is encoded by the following amino acid sequence (NCBI Accession No. NM_002182 and SEQ ID NO: 25):

```
MTLLWCVVSLYFYGILQSDASERCDDWGLDTMRQIQVFEDEPARIKCPL
FEHFLKFNYSTAHSAGLTLIWYWTRQDRDLEEPINFRLPENRISKEKDVL
WFRPTLLNDTGNYTCMLRNTTYCSKVAFPLEVVQKDSCFNSPMKLPVH
KLYIEYGIQRITCPNVDGYFPSSVKPTITWYMGCYKIQNFNNVIPEGMNL
SFLIALISNNGNYTCVVTYPENGRTFHLTRTLTVKVVGSPKNAVPPVIH
SPNDHVVYEKEPGEELLIPCTVYFSFLMDSRNEVWWTIDGKKPDDITI
DVTINESISHSRTEDETRTQILSIKKVTSEDLKRSYVCHARSAKGEVAK
AAKVKQKVPAPRYTVELACGFGATVLLVVILIVVYHVYWLEMVLFYRA
HFGTDETILDGKEYDIYVSYARNAEEEEFVLLTLRGVLENEFGYKLCIFD
RDSLPGGIVTDETLSFIQKSRRLLVVLSPNYVLQGTQALLELKAGLENM
ASRGNINVILVQYKAVKETKVKELKRAKTVLTVIKWKGEKSKYPQGRFW
KQLQVAMPVKKSPRRSSSDEQGLSYSSLKNV.
```

IL-1RAP, transcript variant 2, is encoded by the following mRNA sequence (NCBI Accession No. NM_134470 and SEQ ID NO: 26):

```
tgccgggatccaggtctccggggtccgctttggccagaggcgcggaaggaagcagtgcccggcgacactg cacccatcccggctgcttttgctgcgccctctcagcttcccaagaaaggcatcgtcatgtgatcatcacc taagaactagaacatcagcaggccctagaagcctcactcttgcccctcccttta atatctcaaaggATGa cacttctgtggtgtgtagtgagtctctacttttatggaatcctgcaaagtgatgcctcagaacgctgcga tgactggggactagacaccatgaggcaaatccaagtgtttgaagatgagccagctcgcatcaagtgccca ctctttgaacacttcttgaaattcaactacagcacagcccattcagctggccttactctgatctggtatt ggactaggcaggaccgggaccttgaggagccaattaacttccgcctccccgagaaccgcattagtaagga gaaagatgtgctgtggttccggcccactctcctcaatgacactggcaactatacctgcatgttaaggaac actacatattgcagcaaagttgcatttcccttggaagttgttcaaaaagacagctgtttcaattcccca tgaaactcccagtgcataaactgtatatagaatatggcattcagaggatcacttgtccaaatgtagatgg atattttccttccagtgtcaaaccgactatcacttggtatatgggctgttataaaatacagaatttaat aatgtaatacccgaaggtatgaacttgagtttcctcattgccttaatttcaaataatggaaattacacat gtgttgttacatatccagaaaatggacgtacgtttcatctcaccaggactctgactgtaaaggtagtagg ctctccaaaaaatgcagtgcccctgtgatccattcacctaatgatcatgtggtctatgagaaagaacca ggagaggagctactcattccctgtacggtctattttagttttctgatggattctcgcaatgaggtttggt ggaccattgatggaaaaaacctgatgacatcactattgatgtcaccattaacgaaagtataagtcatag tagaacagaagatgaaacaagaactcagattttgagcatcaagaaagttacctctgaggatctcaagcgc agctatgtctgtcatgctagaagtgccaaaggcgaagttgccaaagcagccaaggtgaagcagaaaggta atagatgcggtcagtgatgaatctctcagctccaaattaacattgtggtgaataaggacaaaaggagaga ttgagaacaagagagctccagcacctagcccgacggcatctaacccatagtaatgaatcaaacttaaatg aaaaatatgaaagttttcatctatgtaagatactcaaaatattgtttctgatattgttagtaccgtaatg cccaaatgtagctaaaaaaatcgacgtgagtacagtgagacacaattttgtgtctgtacaattatgaaaa attaaaaacaaagaaaatattcaaagctaccaaagatagaaaaaactggtagagccacatattgttggtg
```

-continued

```
aattattaagacccttttaaaaatcattcatggtagagtttaagagtcataaaaaagattgcatcatctg acctaagactttcggaattttttcctgaacaaataacagaaagggaattatataccttttaatattattag aagcattatctgtagttgtaaaacattattaatagcagccatccaattgtatgcaactaattaaggtatt gaatgtttattttccaaaaatgcataattataatattattttaaacactatgtatcaatatttaagcagg tttataatataccagcagccacaattgctaaaatgaaaatcatttaaattatgattttaaatggtataaa catgatttctatgttgatagtactatattattctacaataaatggaaattataaagccttcttgtcagaa gtgctgctcctaaaaaaaaaaaaaaaaaaaaaa.
```

IL-1RAP, transcript variant 2, is encoded by the following amino acid sequence (NCBI Accession No. NM_134470 and SEQ ID NO: 27):

```
MTLLWCVVSLYFYGILQSDASERCDDWGLDTMRQIQVFEDEPARIKC

PLFEHFLKFNYSTAHSAGLTLIWYWTRQDRDLEEPINFRLPENRISKEK

DVLWFRPTLLNDTGNYTCMLRNTTYCSKVAFPLEVVQKDSCFNSPMK

LPVHKLYIEYGIQRITCPNVDGYFPSSVKPTITWYMGCYKIQNFNNVIP

EGMNLSFLIALISNNGNYTCVVTYPENGRTFHLTRTLTVKVVGSPKNA

VPPVIHSPNDHVVYEKEPGEELLIPCTVYFSFLMDSRNEVWWTIDGK

KPDDITIDVTINESISHSRTEDETRTQILSIKKVTSEDLKRSYVCHARS

AKGEVAKAAKVKQKGNRCGQ.
``` interleukin-1 Receptor Associated Kinase 1 (IRAK1):

The invention also comprises compositions and methods to inhibit the activity of human IRAK1, defined as the ability of this protein to bind an IL-1 receptor following ligation of this receptor with IL-1, as well as to transduce downstream signals leading to an inflammatory response. Compositions that comprise an inhibitor of IRAK1 antagonize downstream signaling from an IL-1 receptor. The composition comprises a polynucleotide, a polypeptide, an antibody, a compound, or a small molecule with means to inhibit the transcription, transcript stability, translation, modification, localization, secretion, or function of a polynucleotide or polypeptide encoding IRAK1. The inhibitory polynucleotide or polypeptide composition binds to one or more region(s) of IRAK1, and associated isoforms, comprised by SEQ ID NO: 28-33.

IRAK1, transcript variant 1, is encoded by the following mRNA sequence (NCBI Accession No. NM_001569 and SEQ ID NO: 28):

```
cgcggacccggccggcccaggcccgcgcccgccgcggccctgagaggccccggcaggtcccggcccggcg gcggcagccATGgccggggggccgggcccgggggagcccgcagccccggcgcccagcacttcttgtacg aggtgccgccctgggtcatgtgccgcttctacaaagtgatggacgccctggagcccgccgactggtgcca gttcgccgccctgatcgtgcgcgaccagaccgagctgcggctgtgcgagcgctccgggcagcgcacggcc agcgtcctgtggccctggatcaaccgcaacgcccgtgtggccgacctcgtgcacatcctcacgcacctgc agctgctccgtgcgcgggacatcatcacagcctggcaccctcccgccccgcttccgtccccaggcaccac tgccccgaggcccagcagcatccctgcaccecgccgaggccgaggcctggagccccccggaagttgccatcc tcagcctccaccttcctctccccagcttttccaggctcccagacccattcagggcctgagctcggcctgg tcccaagccctgcttccctgtggcctccaccgccatctccagcccctttcttctaccaagccaggcccaga gagctcagtgtccctcctgcagggagcccgcccctttccgttttgctggcccctctgtgagatttcccgg ggcacccacaacttctcggaggagctcaagatcggggagggtggctttgggtgcgtgtaccgggcggtga tgaggaacacggtgtatgctgtgaagaggctgaaggagaacgctgacctggagtggactgcagtgaagca gagcttcctgaccgaggtggagcagctgtccaggtttcgtcacccaaacattgtggactttgctggctac tgtgctcagaacggcttctactgcctggtgtacggcttcctgcccaacggctccctggaggaccgtctcc actgccagacccaggcctgcccacctctctcctggcctcagcgactggacatccttctgggtacagcccg ggcaattcagtttctacatcaggacagccccagcctcatccatggagacatcaagagttccaacgtcctt ctggatgagaggctgacacccaagctgggagactttggcctggcccggttcagccgctttgccgggtcca gccccagccagagcagcatggtggcccggacacagacagtgcggggcaccctggcctacctgcccgagga gtacatcaagacgggaaggctggctgtggacacggacaccttcagctttggggtggtagtgctagagacc ttggctggtcagagggctgtgaagacgcacggtgccaggaccaagtatctgaaagacctggtggaagagg
```

-continued

```
aggctgaggaggctggagtggctttgagaagcacccagagcacactgcaagcaggtctggctgcagatgc
ctgggctgctcccatcgccatgcagatctacaagaagcacctggaccccaggcccgggccctgcccacct
gagctgggcctgggcctgggccagctggcctgctgctgcctgcaccgccgggccaaaaggaggcctccta
tgacccaggtgtacgagaggctagagaagctgcaggcagtggtggcgggggtgcccgggcattcggaggc
cgccagctgcatcccccttccccgcaggagaactcctacgtgtccagcactggcagagcccacagtggg
gctgctccatggcagccctggcagcgccatcaggagccagtgcccaggcagcagagcagctgcagagag
gccccaaccagcccgtggagagtgacgagagcctaggcggcctctctgctgccctgcgctcctggcactt
gactccaagctgccctctggacccagcacccctcagggaggccggctgtcctcaggggggacacggcagga
gaatcgagctgggggagtggcccaggatcccggcccacagccgtggaaggactggcccttggcagctctg
catcatcgtcgtcagagccaccgcagattatcatcaaccctgcccgacagaagatggtccagaagctggc
cctgtacgaggatggggccctggacagcctgcagctgctgtcgtccagctccctcccaggcttgggcctg
gaacaggacaggcaggggcccgaagaaagtgatgaatttcagagctgatgtgttcacctgggcagatccc
ccaaatccggaagtcaaagttctcatggtcagaagttctcatggtgcacgagtcctcagcactctgccgg
cagtgggggtgggggcccatgcccgcggggagagaaggaggtggccctgctgttctaggctctgtgggc
ataggcaggcagagtggaaccctgcctccatgccagcatctgggggcaaggaaggctggcatcatccagt
gaggaggctggcgcatgttgggaggctgctggctgcacagacccgtgaggggaggagaggggctgctgtg
cagggtgtggagtagggagctggctcccctgagagccatgcagggcgtctgcagcccaggcctctggca
gcagctctttgcccatctctttggacagtggccaccctgcacaatggggccgacgaggcctagggccctc
ctacctgcttacaatttggaaaagtgtggccgggtgcggtggctcacgcctgtaatcccagcactttggg
aggccaaggcaggaggatcgctggagcccagtaggtcaagaccagccagggcaacatgatgagaccctgt
ctctgccaaaaaatttttttaaactattagcctggcgtggtagcgcacgcctgtggtcccagctgctggg
aggctgaagtaggaggatcatttatgcttgggaggtcgaggctgcagtgagtcatgattgtatgactgca
ctccagcctgggtgacagagcaagaccctgtttcaaaaagaaaaaccctgggaaaagtgaagtatggctg
taagtctcatggttcagtcctagcaagaagcgagaattctgagatcctccagaaagtcgagcagcaccca
cctccaacctcgggccagtgtcttcaggctttactggggacctgcgagctggcctaatgtggtggcctgc
aagccaggccatccctgggcgccacagacgagctccgagccaggtcaggcttcggaggccacaagctcag
cctcaggcccaggcactgattgtggcagaggggccactacccaaggtctagctaggcccaagacctagtt
acccagacagtgagaagcccctggaaggcagaaaagttgggagcatggcagacagggaagggaaacattt
tcagggaaaagacatgtatcacatgtcttcagaagcaagtcaggtttcatgtaaccgagtgtcctcttgc
gtgtccaaaagtagcccagggctgtagcacaggcttcacagtgattttgtgttcagccgtgagtcacact
acatgccccgtgaagctgggcattggtgacgtccaggttgtccttgagtaataaaaacgtatgttgcaa
taaaaaaaaaaaaaaaaa.
```

IRAK1, transcript variant 1, is encoded by the following amino acid sequence (NCBI Accession No. NM_001569 and SEQ ID NO: 29):

MAGGPGPGEPAAPGAQHFLYEVPPWVMCRFYKVMDALEPADWCQFAALI

VRDQTELRLCERSGQRTASVLWPWINRNARVADLVHILTHLQLLRARDI

ITAWHPPAPLPSPGTTAPRPSSIPAPAEAEAWSPRKLPSSASTFLSPAF

PGSQTHSGPELGLVPSPASLWPPPPSPAPSSTKPGPESSVSLLQGAR

PFPPFCWPLCEISRGTHNFSEELKIGEGGFGCVYRAVMRNTVYAVKRLKE

NADLEWTAVKQSFLTEVEQLSRFRHPNIVDFAGYCAQNGFYCLVYGFLP

NGSLEDRLHCQTQACPPLSWPQRLDILLGTARAIQFLHQDSPSLIHGDI

KSSNVLLDERLTPKLGDFGLARFSRFAGSSPSQSSMVARTQTVRGTL

AYLPEEYIKTGRLAVDTDTFSFGVVVLETLAGQRAVKTHGARTKYLKDL

VEEEAEEAGVALRSTQSTLQAGLAADAWAAPIAMQIYKKHLDPRPGPC

PPELGLGLGQLACCCLHRRAKRRPPMTQVYERLEKLQAVVAGVPGHS

EAASCIPPSPQENSYVSSTGRAHSGAAPWQPLAAPSGASAQAAEQLQ

RGPNQPVESDESLGGLSAALRSWHLTPSCPLDPAPLREAGCPQGDTA

-continued

GESSWGSGPGSRPTAVEGLALGSSASSSSEPPQIIINPARQKMVQKLAL
YEDGALDSLQLLSSSSLPGLGLEQDRQGPEESDEFQS.

IRAK1, transcript variant 2, is encoded by the following mRNA sequence (NCBI Accession No. NM_001025242 and SEQ ID NO: 30):

cgcggacccggccggcccaggcccgcgcccgccgcggccctgagaggccccggcaggtcccggcccggcg
gcggcagccATGgccggggggccgggccggggagcccgcagccccggcgcccagcacttcttgtacg
aggtgccgccctgggtcatgtgccgcttctacaaagtgatggacgccctggagcccgccgactggtgcca
gttcgccgccctgatcgtgcgcgaccagaccgagctgcggctgtgcgagcgctccgggcagcgcacggcc
agcgtcctgtggccctggatcaaccgcaacgcccgtgtggccgacctcgtgcacatcctcacgcacctgc
agctgctccgtgcgcgggacatcatcacagcctggcaccctcccgcccgcttccgtccccaggcaccac
tgccccgaggcccagcagcatcctgcacccgccgaggccgaggcctggagcccccggaagttgccatcc
tcagcctccaccttcctctcccagcttttccaggctcccagacccattcagggcctgagctcggcctgg
tcccaagccctgcttccctgtggcctccaccgccatctccagcccttcttctaccaagccaggcccaga
gagctcagtgtccctcctgcagggagcccgccccttccgttttgctggcccctctgtgagatttcccgg
ggcacccacaacttctcggaggagctcaagatcggggagggtggctttgggtgcgtgtaccgggcggtga
tgaggaacacggtgtatgctgtgaagaggctgaaggagaacgctgacctggagtggactgcagtgaagca
gagcttcctgaccgaggtggagcagctgtccaggtttcgtcacccaaacattgtggactttgctggctac
tgtgctcagaacggcttctactgcctggtgtacggcttcctgcccaacggccctggaggaccgtctcc
actgccagacccaggcctgcccacctctctcctggcctcagcgactggacatccttctgggtacagcccg
ggcaattcagtttctacatcaggacaccccagcctcatccatggagacatcaagagttccaacgtcctt
ctggatgagaggctgacacccaagctgggagactttggcctggcccggttcagccgctttgccgggtcca
gccccagccagagcagcatggtggcccggacacagacagtgcggggcaccctggcctacctgcccgagga
gtacatcaagacgggaaggctggctgtggacacggacaccttcagctttggggtggtagtgctagagacc
ttggctggtcagagggctgtgaagacgcacggtgccaggaccaagtatctgaaagacctggtggaagagg
aggctgaggaggctggagtggctttgagaagcacccagagcacactgcaagcaggtctggctgcagatgc
ctgggctgctcccatcgccatgcagatctacaagaagcacctggaccccaggcccgggccctgcccacct
gagctgggcctgggcctgggccagctggcctgctgctgcctgcaccgccgggccaaaaggaggcctccta
tgacccaggagaactcctacgtgtccagcactggcagagcccacagtggggctgctccatggcagcccct
ggcagcgccatcaggagccagtgcccaggcagcagagcagctgcagagaggcccaaccagcccgtggag
agtgacgagagcctaggcggcctctctgctgccctgcgctcctggcacttgactccaagctgccctctgg
acccagcacccctcagggaggccggctgtcctcaggggacacggcaggagaatcgagctgggggagtgg
cccaggatcccggcccacagccgtggaaggactggcccttggcagctctgcatcatcgtcgtcagagcca
ccgcagattatcatcaaccctgcccgacagaagatggtccagaagctggccctgtacgaggatggggccc
tggacagcctgcagctgctgtcgtccagctccctcccaggcttgggcctggaacaggacaggcagggcc
cgaagaaagtgatgaatttcagagctgatgtgttcacctgggcagatcccccaaatccggaagtcaaagt
tctcatggtcagaagttctcatggtgcacgagtcctcagcactctgccggcagtgggggtgggggcccat
gcccgcggggagagaaggaggtggccctgctgttctaggctctgtgggcataggcaggcagagtggaac
cctgcctccatgccagcatctgggggcaaggaaggctggcatcatccagtgaggaggctggcgcatgttg
ggaggctgctggctgcacagacccgtgaggggaggagaggggctgctgtgcaggggtgtggagtagggag
ctggctcccctgagagccatgcagggcgtctgcagcccaggcctctggcagcagctctttgcccatctct
ttggacagtggccaccctgcacaatgggggccgacgaggcctagggcccctcctacctgcttacaatttgga -continued

```
aaagtgtggccgggtgcggtggctcacgcctgtaatcccagcactttgggaggccaaggcaggaggatcg
ctggagcccagtaggtcaagaccagccagggcaacatgatgagacctgtctctgccaaaaaatttttta
aactattagcctggcgtggtagcgcacgcctgtggtcccagctgctggggaggctgaagtaggaggatca
tttatgcttgggaggtcgaggctgcagtgagtcatgattgtatgactgcactccagcctgggtgacagag
caagaccctgtttcaaaaagaaaaccctgggaaaagtgaagtatggctgtaagtctcatggttcagtcc
tagcaagaagcgagaattctgagatcctccagaaagtcgagcagcacccacctccaacctcgggccagtg
tcttcaggctttactggggacctgcgagctggcctaatgtggtggcctgcaagccaggccatccctgggc
gccacagacgagctccgagccaggtcaggcttcggaggccacaagctcagcctcaggcccaggcactgat
tgtggcagaggggccactacccaaggtctagctaggcccaagacctagttacccagacagtgagaagccc
ctggaaggcagaaaagttgggagcatggcagacagggaagggaaacattttcagggaaaagacatgtatc
acatgtcttcagaagcaagtcaggtttcatgtaaccgagtgtcctcttgcgtgtccaaaagtagcccagg
gctgtagcacaggcttcacagtgattttgtgttcagccgtgagtcacactacatgccccgtgaagctgg
gcattggtgacgtccaggttgtccttgagtaataaaaacgtatgttgcaataaaaaaaaaaaaaaaaaa.
```

IRAK1, transcript variant 2, is encoded by the following amino acid sequence (NCBI Accession No. NM_001025242 and SEQ ID NO: 31):

```
MAGGPGPGEPAAPGAQHFLYEVPPWVMCRFYKVMDALEPADWCQFAALIVRDQTELR
LCERSGQRTASVLWPWINRNARVADLVHILTHLQLLRARDIITAWHPPAPLPSPGTTAPR
PSSIPAPAEAEAWSPRKLPSSASTFLSPAFPGSQTHSGPELGLVPSPASLWPPPPSPAPSST
KPGPESSVSLLQGARPFPFCWPLCEISRGTHNFSEELKIGEGGFGCVYRAVMRNTVYAV
KRLKENADLEWTAVKQSFLTEVEQLSRFRHPNIVDFAGYCAQNGFYCLVYGFLPNGSL
EDRLHCQTQACPPLSWPQRLDILLGTARAIQFLHQDSPSLIHGDIKSSNVLLDERLTPKLG
DFGLARFSRFAGSSPSQSSMVARTQTVRGTLAYLPEEYIKTGRLAVDTDTFSFGVVVLET
LAGQRAVKTHGARTKYLKDLVEEEAEEAGVALRSTQSTLQAGLAADAWAAPIAMQIY
KKHLDPRPGPCPPELGLGLGQLACCCLHRRAKRRPPMTQENSYVSSTGRAHSGAAPWQ
PLAAPSGASAQAAEQLQRGPNQPVESDESLGGLSAALRSWHLTPSCPLDPAPLREAGCP
QGDTAGESSWGSGPGSRPTAVEGLALGSSASSSSEPPQIIINPARQKMVQKLALYEDGAL
DSLQLLSSSSLPGLGLEQDRQGPEESDEFQS.
```

IRAK1, transcript variant 3, is encoded by the following mRNA sequence (NCBI Accession No. NM_001025243 and SEQ ID NO: 32):

```
cgcggacccggccggcccaggcccgcgcccgcgcgcgggccctgagaggccccggcaggtcccggcccggcg
gcggcagccATGgccggggggccgggcccgggggagcccgcagccccggcgcccagcacttcttgtacg
aggtgccgccctgggtcatgtgccgcttctacaaagtgatggacgccctggagcccgccgactggtgcca
gttcgccgcccctgatcgtgcgcgaccagaccgagctgcggctgtgcgagcgctccgggcagcgcacggcc
agcgtcctgtggccctggatcaaccgcaacgcccgtgtggccgacctcgtgcacatcctcacgcacctgc
agctgctccgtgcgcgggacatcatcacagcctggcaccctcccgccccgcttccgtccccaggcaccac
tgccccgaggcccagcagcatccctgcaccgccgaggccgaggcctggagcccccggaagttgccatcc
tcagcctccaccttcctctccccagcttttccaggctcccagacccattcagggcctgagctcggcctgg
tcccaagccctgcttccctgtggcctccaccgccatctccagccccttcttctaccaagccaggcccaga
```

```
gagctcagtgtccctcctgcagggagcccgccccttccgttttgctggcccctctgtgagatttcccgg
ggcacccacaacttctcggaggagctcaagatcggggaggggtggctttgggtgcgtgtaccgggcggtga
tgaggaacacggtgtatgctgtgaagaggctgaaggagaacgctgacctggagtggactgcagtgaagca
gagcttcctgaccgaggtggagcagctgtccaggtttcgtcacccaaacattgtggactttgctggctac
tgtgctcagaacggcttctactgcctggtgtacggcttcctgcccaacggctccctggaggaccgtctcc
actgccagacccaggcctgccacctctcctggcctcagcgactggacatccttctgggtacagcccg
ggcaattcagtttctacatcaggacagccccagcctcatccatggagacatcaagagttccaacgtcctt
ctggatgagaggctgacacccaagctgggagactttggcctggcccggttcagccgctttgccgggtcca
gccccagccagagcagcatggtggcccggacacagacagtgcggggcaccctggcctacctgcccgagga
gtacatcaagacgggaaggctggctgtggacacggacaccttcagctttggggtggtagtgctagagacc
ttggctggtcagagggctgtgaagacgcacggtgccaggaccaagtatctggtgtacgagaggctagaga
agctgcaggcagtggtggcgggggtgcccgggcattcggaggccgccagctgcatccccccttccccgca
ggagaactcctacgtgtccagcactggcagagcccacagtggggctgctccatggcagcccctggcagcg
ccatcaggagccagtgcccaggcagcagagcagctgcagagaggccccaaccagcccgtggagagtgacg
agagcctaggcggcctctctgctgccctgcgctcctggcacttgactccaagctgccctctggacccagc
acccctcagggaggccggctgtcctcaggggacacggcaggagaatcgagctgggggagtggcccagga
tcccggcccacagccgtggaaggactggcccttggcagctctgcatcatcgtcgtcagagccaccgcaga
ttatcatcaaccctgcccgacagaagatggtccagaagctggccctgtacgaggatggggccctggacag
cctgcagctgctgtcgtccagctccctcccaggcttgggcctggaacaggacaggcaggggcccgaagaa
agtgatgaatttcagagctgatgtgttcacctgggcagatcccccaaatccggaagtcaaagttctcatg
gtcagaagttctcatggtgcacgagtcctcagcactctgccggcagtgggggtggggccccatgcccgcg
ggggagagaaggaggtggccctgctgttctaggctctgtgggcataggcaggcagagtggaaccctgcct
ccatgccagcatctgggggcaaggaaggctggcatcatccagtgaggaggctggcgcatgttgggaggct
gctggctgcacagacccgtgaggggaggagaggggctgctgtgcaggggtgtggagtagggagctggctc
ccctgagagccatgcagggcgtctgcagcccaggcctctggcagcagctcttttgcccatctctttggaca
gtggccaccctgcacaatggggccgacgaggcctagggcccctcctacctgcttacaatttggaaaagtgt
ggccgggtgcggtggctcacgcctgtaatcccagcactttgggaggccaaggcaggaggatcgctggagc
ccagtaggtcaagaccagccagggcaacatgatgagaccctgtctctgccaaaaaatttttttaaactatt
agcctggcgtggtagcgcacgcctgtggtcccagctgctggggaggctgaagtaggaggatcatttatgc
ttgggaggtcgaggctgcagtgagtcatgattgtatgactgcactccagcctgggtgacagagcaagacc
ctgtttcaaaaagaaaaaccctgggaaaagtgaagtatggctgtaagtctcatggttcagtcctagcaag
aagcgagaattctgagatcctccagaaagtcgagcagcacccacctccaacctcgggccagtgtcttcag
gctttactggggacctgcgagctggcctaatgtggtggcctgcaagccaggccatccctgggcgccacag
acgagctccgagccaggtcaggcttcggaggccacaagctcagcctcaggcccaggcactgattgtggca
gaggggccactacccaaggtctagctaggcccaagacctagttacccagacagtgagaagcccctggaag
gcagaaaagttgggagcatggcagacagggaagggaaacattttcagggaaaagacatgtatcacatgtc
ttcagaagcaagtcaggtttcatgtaaccgagtgtcctcttgcgtgtccaaaagtagcccagggctgtag
cacaggcttcacagtgattttgtgttcagccgtgagtcacactacatgccccgtgaagctgggcattgg
tgacgtccaggttgtccttgagtaataaaaacgtatgttgcaataaaaaaaaaaaaaaaaaaa.
```

IRAK1, transcript variant 3, is encoded by the following amino acid sequence (NCBI Accession No. NM_001025243 and SEQ ID NO: 33):

MAGGPGPGEPAAPGAQHFLYEVPPWVMCRFYKVMDALEPADWCQFAALIVRDQTELR

LCERSGQRTASVLWPWINRNARVADLVHILTHLQLLRARDIITAWHPPAPLPSPGTTAPR

PSSIPAPAEAEAWSPRKLPSSASTFLSPAFPGSQTHSGPELGLVPSPASLWPPPPSPAPSST

KPGPESSVSLLQGARPFPFCWPLCEISRGTHNFSEELKIGEGGFGCVYRAVMRNTVYAV

KRLKENADLEWTAVKQSFLTEVEQLSRFRHPNIVDFAGYCAQNGFYCLVYGFLPNGSL

EDRLHCQTQACPPLSWPQRLDILLGTARAIQFLHQDSPSLIHGDIKSSNVLLDERLTPKLG

DFGLARFSRFAGSSPSQSSMVARTQTVRGTLAYLPEEYIKTGRLAVDTDTFSFGVVVLET

LAGQRAVKTHGARTKYLVYERLEKLQAVVAGVPGHSEAASCIPPSPQENSYVSSTGRA

HSGAAPWQPLAAPSGASAQAAEQLQRGPNQPVESDESLGGLSAALRSWHLTPSCPLDP

APLREAGCPQGDTAGESSWGSGPGSRPTAVEGLALGSSASSSSEPPQIIINPARQKMVQK

LALYEDGALDSLQLLSSSSLPGLGLEQDRQGPEESDEFQS.

Silencing Expression with MicroRNAs

The present invention comprises compositions with means to inhibit the activity of IL-1α, IL-1b, IL-1R1, IL-1R2, Il-1Ra3, IL-1RAP, or IRAK1, by delivering microRNA (miRNA) molecules to an ocular or adnexal tissue with an appropriate pharmaceutical carrier. Compositions that comprise an miRNA targeted to either IL-1α, IL-1b, IL-1R1, IL-1R2, Il-1Ra3, IL-1RAP, or IRAK1 antagonize the function of IL-1R1. The composition comprises one or more miRNA(s) that bind to one or more regions of IL-1α, IL-1b, IL-1R1, IL-1R2, Il-1Ra3, IL-1RAP, or IRAK1. The following table contains exemplary miRNAs that have been shown to partially or completely silence the expression of human IL-1α or IL-1R1.

inhibition, prevention, diminution, reduction, decrease, repression, or interruption intracellular signaling initiated, communicated, or transduced from an IL-1 receptor. In one aspect of the invention, inhibition, prevention, diminution, reduction, decreases, repression, or interruption of intracellular signaling initiated, communicated, or transduced from an IL-1 receptor is achieved by preventing or decreasing binding of an IL-1 cytokine to an IL-1R. Alternatively, or in addition, transduction of intracellular signaling from an IL-1R is prevented by removing, silencing, or mutating a downstream effector or target within a signaling cascade. The expression and/or function or activity of downstream effectors and/or targets are removed (e.g. deleted, knocked-out, sequestered, denatured, degraded, etc.), silenced (degraded, transcriptionally or translationally repressed), or mutated (nucleotide or amino acid sequence encoding the

TABLE 1

Summary of miRNAs, their human target genes, nucleotide sequences, and their sequence identifier numbers.

| Target Gene | miRNA | Polynucleotide sequence (5' to 3') | SEQ ID NO: |
| --- | --- | --- | --- |
| IL-1α | miR-30c | UGUAAACAUCCUACACUCUCAGC | 34 |
| IL-1α | miR-30b | UGUAAACAUCCUACACUCAGC | 35 |
| IL-1α | miR-30a-5p | UGUAAACAUCCUCGACUGGAAGC | 36 |
| IL-1α | miR-24 | UGGCUCAGUUCAGCAGGAACAG | 37 |
| IL-1R1 | miR-135b | UAUGGCUUUUCAUUCCUAUGUG | 38 |
| IL-1R1 | miR-326 | CCUCUGGGCCCUUCCUCCAG | 39 |
| IL-1R1 | miR-184 | UGGACGGAGAACUGAUAAGGGU | 40 |
| IL-1R1 | miR-214 | ACAGCAGGCACAGACAGGCAG | 41 |
| IL-1R1 | miR-203 | GUGAAAUGUUUAGGACCACUAG | 42 |
| IL-1R1 | miR-331 | GCCCCUGGGCCUAUCCUAGAA | 43 |
| IL-1R1 | miR-205 | UCCUUCAUUCCACCGGAGUCUG | 44 |

IL-1 and IL-1R-Mediated Signaling

As used herein, the term "inhibit an activity of an inflammatory interleukin-1 cytokine" is meant to describe the active product is altered to encode a non-functional product) by genetic modification or administration of a therapeutic compound.

Exemplary downstream effectors and/or targets include, but are not limited to, one or more isoforms or homologs of an IL-1 (interleukin 1), an IL-1α (interleukin 1 alpha), an IL-1β (interleukin 1 beta), an IL-1R (interleukin 1 receptor, type I), an IL-1Ra (IIL-1R antagonist), an IL-1RAcP (IL-1R accessory protein), a TOLLIP (TOLL interacting protein), an IRAK1 (IL-1R associated kinase 1), an IRAK2 (IL-1R associated kinase 2), an IRAK 3 (IL-1R associated kinase 3), a MYD88 (myeloid differentiation primary response gene 88), an ECSIT (evolutionarily conserved signaling intermediate in Toll pathways), a TRAF6 (TNF-receptor associated factor 6), a MEKK1 (MAP ERK kinase kinase 1), a TAB1 (TAK1 binding protein 1), a TAK1 (transforming growth factor b activated kinase 1), a NIK (NFkB Inducing Kinase), a RKIP (Raf kinase inhibitor protein), a MEK3 (Mitogen-Activated Protein Kinase Kinase 3; MEK3 or MKK3), a MEK6 (Mitogen-Activated Protein Kinase Kinase 6; MEK6 or MKK6), a MAPK14 (mitogen activated protein kinase 14), a MAPK8 (mitogen activated protein kinase 8), a MEKK1 (mitogen activated protein kinase kinase kinase 1), a MAP3K14 (mitogen activated protein kinase kinase kinase 14), a MEKK7 (mitogen activated protein kinase kinase kinase 7 or MKK7), a MAP3K7IP1 (mitogen activated protein kinase kinase kinase 7 interacting protein 1), a JNK (Jun N-terminal kinase), p38 (also known as p38 MAPK or p38 mitogen activated protein kinase), cJUN (jun oncogene), AP-1 (activator protein 1; transcription factor), IL-6 (interleukin 6, also known as interferon beta 2), TNFα (tumor necrosis factor-alpha), a TNF (tumor necrosis factor superfamily member), an IFNα (interferon alpha, interferon alpha 1), an IFNβ (interferon beta, interferon beta 1), a TGFβ1 (transforming growth factor beta 1), a TGFβ2 (transforming growth factor beta 2), a TGFβ3 (transforming growth factor beta 3), an IKKα (inhibitor of kappa light polypeptide gene enhancer in B-cells, kinase alpha), an IKKβ (inhibitor of kappa light polypeptide gene enhancer in B-cells, kinase beta), a IκBα (nuclear factor of kappa light polypeptide gene enhancer in B-cells inhibitor, alpha), a Chuk (conserved helix-loop-helix ubiquitous kinase), and a NFκB (nuclear factor of kappa light polypeptide gene enhancer in B-cells 1; also known as p105). Additional signaling molecules and relationships are defined by O'Neill, L. A. J. and Greene, C. 1998. Journal of Leukocyte Biology. 63: 650-657.

The inhibition of an activity of an inflammatory interleukin-1 cytokine is determined by sampling an ocular or adnexal tissue or fluid and determining the abundance of a polynucleotide or polypeptide which encodes for component of an IL-1R signaling cascade. An increase or decrease in the abundance of a polynucleotide or polypeptide which encodes for component of an IL-1R signaling cascade following administration of a therapeutic composition of the invention compared to the abundance of the component of an IL-1R signaling cascade prior to the administration indicates inhibition of an activity of an inflammatory interleukin-1 cytokine.

Figure 4:
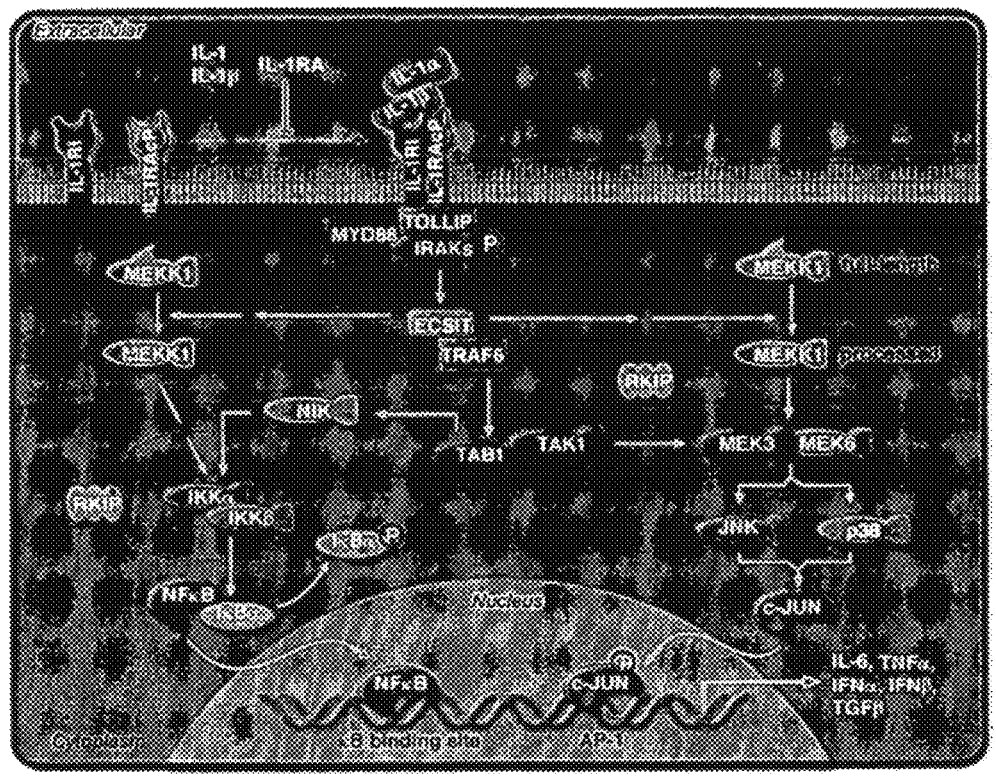
FIG. 4 is a schematic representation of signaling pathways that are transduced from the IL-1R and the downstream effectors involved in carrying these intracellular signals (drawing reproduced from BioCarta website).

Specifically, FIG. 4 shows the functional interrelationships between components of two exemplary signaling cascades. The arrows between components in this figure indicate that the component preceding the arrow activates the component following the arrow. Conversely, the blunted lines indicated that the component preceding the blunted line inhibits the activity or function of the component following the blunted line.

Briefly, the IL-1R, type I, binds IL-1β, however, IL-1R requires the IL-1 receptor accessory protein (IL-1RAcP) to transduce a signal. IL-1 binding causes activation of two kinases, IRAK-1 and IRAK-2, associated with the IL-1 receptor complex. IRAK-1 (IL-1 Receptor Associated Kinase) activates and recruits TRAF6 to the IL-1 receptor complex. TRAF6 activates two pathways, one leading to NF-kB activation and another leading to c-jun activation. The TRAF associated protein ECSIT leads to c-Jun activation through the Map kinase/JNK signaling system. TRAF6 also signals through the TAB1/TAK1 kinases to trigger the degradation of 1-kB, and activation of NF-kB.

For instance, in certain embodiments of the invention, a decrease in the abundance or absence of the processed form of MEKK1, a decrease in the abundance or absence of phosphorylated IκBα, a decrease in the abundance or absence of phosphorylated c-JUN, a decrease in the abundance or absence of ICAM-1, or a decrease in the abundance or absence of IL-6, TNFα, IFNα, IFNβ, TGFβ in an ocular or adnexal tissue or fluid is indicative of inhibition of an inflammatory interleukin-1 cytokine. Similarly, a decrease or absence of activity or function of any of the above-listed components is indicative of inhibition of an inflammatory interleukin-1 cytokine.

Pharmaceutically-Appropriate Carriers

Exemplary compounds incorporated to facilitate and expedite transdermal delivery of topical compositions into ocular or adnexal tissues include, but are not limited to, alcohol (ethanol, propanol, and nonanol), fatty alcohol (lauryl alcohol), fatty acid (valeric acid, caproic acid and capric acid), fatty acid ester (isopropyl myristate and isopropyl n-hexanoate), alkyl ester (ethyl acetate and butyl acetate), polyol (propylene glycol, propanedione and hexanetriol), sulfoxide (dimethylsulfoxide and decylmethylsulfoxide), amide (urea, dimethylacetamide and pyrrolidone derivatives), surfactant (sodium lauryl sulfate, cetyltrimethylammonium bromide, polaxamers, spans, tweens, bile salts and lecithin), terpene (d-limonene, alpha-terpeneol, 1,8-cineole and menthone), and alkanone (N-heptane and N-nonane). Moreover, topically-administered compositions comprise surface adhesion molecule modulating agents including, but not limited to, a cadherin antagonist, a selectin antagonist, and an integrin antagonist.

Optionally, the composition further contains a compound selected from the group consisting of a physiological acceptable salt, poloxamer analogs with carbopol, carbopol/hydroxypropyl methyl cellulose (HPMC), carbopol-methyl cellulose, carboxymethylcellulose (CMC), hyaluronic acid, cyclodextrin, and petroleum.

Drug Delivery by Contact Lens

The invention comprises a contact lens and a composition that inhibits an activity of an inflammatory interleukin-1 cytokine. For example, the composition is incorporated into or coated onto said lens. The composition is chemically bound or physically entrapped by the contact lens polymer. Alternatively, a color additive is chemically bound or physically entrapped by the polymer composition that is released at the same rate as the therapeutic drug composition, such that changes in the intensity of the color additive indicate changes in the amount or dose of therapeutic drug composition remaining bound or entrapped within the polymer. Alternatively, or in addition, an ultraviolet (UV) absorber is chemically bound or physically entrapped within the contact lens polymer. The contact lens is either hydrophobic or hydrophilic.

Exemplary materials used to fabricate a hydrophobic lens with means to deliver the compositions of the present invention include, but are not limited to, amefocon A, amsilfocon A, aquilafocon A, arfocon A, cabufocon A, cabufocon B, carbosilfocon A, crilfocon A, crilfocon B, dimefocon A, enflufocon A, enflofocon B, erifocon A, fluorofocon A, flusilfocon A, flusilfocon B, flusilfocon C, flusilfocon D, flusilfocon E, hexafocon A, hofocon A, hybufocon A, itabisfluorofocon A, itafluorofocon A, itafocon A, itafocon B, kolfocon A, kolfocon B, kolfocon C, kolfocon D, lotifocon A, lotifocon B, lotifocon C, melafocon A, migafocon A, nefocon A, nefocon B, nefocon C, onsifocon A, oprifocon A, oxyfluflocon A, paflufocon B, paflufocon C, paflufocon D, paflufocon E, paflufocon F, pasifocon A, pasifocon B, pasifocon C, pasifocon D, pasifocon E, pemufocon A, porofocon A, porofocon B, roflufocon A, roflufocon B, roflufocon C, roflufocon D, roflufocon E, rosilfocon A, satafocon A, siflufocon A, silafocon A, sterafocon A, sulfocon A, sulfocon B, telafocon A, tisilfocon A, tolofocon A, trifocon A, unifocon A, vinafocon A, and wilofocon A.

Exemplary materials used to fabricate a hydrophilic lens with means to deliver the compositions of the present invention include, but are not limited to, abafilcon A, acofilcon A, acofilcon B, acquafilcon A, alofilcon A, alphafilcon A, amfilcon A, astifilcon A, atlafilcon A, balafilcon A, bisfilcon A, bufilcon A, comfilcon A, crofilcon A, cyclofilcon A, darfilcon A, deltafilcon A, deltafilcon B, dimefilcon A, droxfilcon A, elastofilcon A, epsilfilcon A, esterifilcon A, etafilcon A, focofilcon A, galyfilcon A, genfilcon A, govafilcon A, hefilcon A, hefilcon B, hefilcon C, hilafilcon A, hilafilcon B, hioxifilcon A, hioxifilcon B, hioxifilcon C, hydrofilcon A, lenefilcon A, licryfilcon A, licryfilcon B, lidofilcon A, lidofilcon B, lotrafilcon A, lotrafilcon B, mafilcon A, mesafilcon A, methafilcon B, mipafilcon A, nelfilcon A, netrafilcon A, ocufilcon A, ocufilcon B, C, ocufilcon D, ocufilcon E, ofilcon A, omafilcon A, oxyfilcon A, pentafilcon A, perfilcon A, pevafilcon A, phemfilcon A, polymacon, senofilcon A, silafilcon A, siloxyfilcon A, surfilcon A, tefilcon A, tetrafilcon A, trilfilcon A, vifilcon A, vifilcon B, and xylofilcon A.

EXAMPLES

Example 1: The Ocular Surface Disease Index (OSDI)

The Ocular Surface Disease Index (OSDI) is a 12-item questionnaire that provides a rapid assessment of the symptoms of ocular irritation consistent with ocular surface disease, including posterior blepharitis and dry eye disease, and their impact on vision-related functioning (FIG. 1). The 12 items of the OSDI questionnaire are graded on a scale of 0 to 4, where 0 indicates none of the time; 1, some of the time; 2, half of the time; 3, most of the time; and 4, all of the time. The total OSDI score is then calculated on the basis of the following formula: OSDI=[(sum of scores for all questions answered)×100]/[(total number of questions answered)×4]. Thus, the OSDI is scored on a scale of 0 to 100, with higher scores representing greater disability. A negative change from baseline indicates an improvement in vision-related function and the ocular inflammatory disorders described herein. For the therapeutic method described herein, treatment is considered more effective than control (vehicle) as indicated by a mean change (decrease) from baseline for the OSDI of >10 units compared to control.

Therapeutic treatment is considered more effective than the vehicle as indicated by a mean change from baseline of average score (0-100) for the Ocular Surface Disease Index (OSDI) of >10 units better than vehicle.

Example 2: Tear Film Break-up Time

The standard TBUT measurement is performed by moistening a fluorescein strip with sterile non-preserved saline and applying it to the inferior tarsal conjunctiva. After several blinks, the tear film is examined using a broad beam of the slit lamp with a blue filter. The time lapse between the last blink and the appearance of the first randomly distributed dark discontinuity in the fluorescein stained tear film is measured three times and the mean value of the measurements is calculated. The tear break-up time is evaluated prior to the instillation of any eye drops and before the eyelids are manipulated in any way. Break-up times less than 10 seconds are considered abnormal. A positive change from baseline indicates improvement in symptoms of the ocular inflammatory disorders described herein. The treatment described herein, leads to an improvement in TBUT significantly greater than that observed from treatment with vehicle alone.

Example 3: Corneal and Conjunctival Staining

Corneal staining is a measure of epithelial disease, or break in the epithelial barrier of the ocular surface, typically seen with ocular surface disorders such as posterior blepharitis and dry eye, among others. Importantly, corneal staining can exist even without clinically evident dry eye, if there is significant lid disease, such as posterior blepharitis. Corneal staining is highly correlated with ocular discomfort in many, though not all patients; in general corneal staining is associated with high scores in the OSDI, as described above. For corneal fluorescein staining, saline-moistened fluorescein strips or 1% sodium fluorescein solution are used to stain the tear film. The entire cornea is then examined using slit-lamp evaluation with a yellow barrier filter (#12 Wratten) and cobalt blue illumination (staining is more intense when it is observed with a yellow filter). Staining is graded according to the Oxford Schema (FIG. 2).

Conjunctival staining is a measure of epithelial disease or break in the epithelial barrier of the ocular surface, typically seen with ocular surface disorders such as posterior blepharitis and dry eye, among others. Importantly, conjunctival staining, similar to corneal staining, can exist even without clinically evident dry eye, if there is significant lid disease, such as posterior blepharitis. Conjunctival staining can also correlate with symptoms of ocular irritation and high OSDI scores as described above. Conjunctival staining is performed under the slit-lamp using lissamine green. Saline-moistened strip or 1% lissamine green solution is used to stain the tear film, and interpalpebral conjunctival staining is evaluated more than 30 seconds, but less than 2 minutes, later. Using white light of moderate intensity, only the interpalpebral region of the nasal and temporal conjunctival staining is graded using the Oxford Schema (above). The treatment described herein leads to decreases in ocular staining scores beyond what is observed with the vehicle alone.

Therapeutic treatment is considered more effective than vehicle as indicated by a mean change from baseline in average score (0-5 scale) for corneal and conjunctival staining of >1 unit better than vehicle, e.g. as detected using the Oxford Schema.

Example 4: Schirmer Test

The Schirmer test is performed in the presence and in the absence of anesthesia by placing a narrow filter-paper strip (5×3 5 mm strip of Whatman #41 filter paper) in the inferior cul-de-sac. This test is conducted in a dimly lit room. The patient gently closes his/her eyes until five minutes have elapsed and the strips are removed. Because the tear front will continue advancing a few millimeters after it has been removed from the eyes, the tear front is marked with a ball-point pen at precisely five minutes. Aqueous tear production is measured by the length in millimeters that the strip wets during 5 minutes. Results of 10 mm or less for the Schirmer test without anesthesia and 5 mm or less for the Schirmer test with anesthesia are considered abnormal. A positive change from baseline indicates improvement of one or more symptoms of an ocular inflammatory disorder described herein.

Example 5: Meibomian Gland Evaluation

In the center of the lower lid, 10 adjacent central glands are located on both sides and the glands are expressed by applying a firm digital pressure at the base of the glands. The number of glands expressed for each eye is documented. The quality of secretion is described as follows:
Clear excreta or clear with small particles (0)
Opaque excreta with normal viscosity (1)
Opaque excreta with increased viscosity (2)
Secretions retain shape after expression (3)
Posterior blepharitis is associated with lid inflammation and alterations in the quantity and/or quality of the meibomian gland secretions, with severe disease associated with quality grades 2-3, as described above. The treatment described herein leads to improvement in meibomian secretion characterized by a decrease in this score; for example, from 3 to 2, or from 2 to 1. An improvement is indicated by a mean change from baseline (0-3 scale) for meibomian gland secretion quality of >1 unit better than vehicle.

Example 6: Lid and Lid Margin Erythema

Lid margin vascular injection (erythema) is defined as a red discoloration, compared to the surrounding eyelid skin and is graded as follows:
None (0): none
Mild (1): redness localized to a small region of the lid margin(s) or skin
Moderate (2): redness of most of the lid margin(s)
Severe (3): redness of most or all the lid margin(s) and skin
Very Severe (4): marked diffuse redness of both lid margins and skin
The presence or absence of tarsal telangiectasis is also noted. Lid telangiectasia is defined as the presence of at least two blood vessels along the eyelid margin.

Example 7: Conjunctiva Hyperemia

Bulbar conjunctival hyperemia is graded as follows:
None (0): none
Mild (1): slight localized injection
Moderate (2): pink color, confined to palpebral or bulbar conjunctiva
Severe (3): red color of the palpebral and/or bulbar conjunctiva
Very Severe (4): marked dark redness of the palpebral and/or bulbar conjunctiva
The presence or absence of tarsal papillary hypertrophy is also noted.

Example 8: Topical Administration of IL-1Ra for Treating Posterior Blepharitis

The following study evaluates the therapeutic benefit of topically administering a solution comprising a known, and commercially-available, recombinant IL-1 receptor antagonist, Anakinra (Kineret®), versus vehicle to subjects with inflammatory conditions affecting one or more ocular and/or adnexal tissues.

The following is a prospective, single-center, randomized, double-masked, vehicle-controlled, parallel-group clinical study. There is one active treatment group and one vehicle treated group. Patients who meet the requirements of the inclusion/exclusion criteria at the screening visit are separated into a moderate stratum and a severe stratum based on the meibomian gland secretion quality. Within each stratum, patients are randomized to either 2.5% topical human recombinant IL-1Ra or vehicle in even allocations. There are a minimum of 20 patients in each treatment group in the moderate stratum and a minimum of 10 patients in each treatment group in the severe stratum. This study consists of 6 scheduled visits over four months (Table 2).

Subjects who present signs or reported symptoms consistent with inflammatory disease affecting an ocular or adnexal tissue are further evaluated prior to treatment using the above-described Ocular Surface Disease Index (OSDI). Exemplary subjects are Male and female patients with signs and symptoms of posterior blepharitis (provided that not more than 7 glands are not expressible) with or without aqueous deficiency excluding those patients with end-stage lacrimal gland (Schirmer reading without anesthesia <3 mm/5 min or if their dry eye disease is the result of destruction of conjunctival goblet cells or scarring). A subject is included in the following study if he or she meets the following criteria: male or female; at least 18 years of age; has not worn contact lenses for at least 2 weeks prior to the study and agrees to not wear contact lenses during study; patient is in generally good & stable overall health. patient must have a diagnosis of posterior blepharitis as defined in FIG. 5; a negative urine pregnancy test result for women of childbearing potential; women of childbearing potential must agree to use adequate contraception (hormonal or barrier method of birth control) prior to study entry and for the duration of study participation; normal lid position and closure; ability to understand and provide informed consent to participate in this study; and willingness to follow study instructions and likely to complete all required visits.

Subjects are excluded if they had used topical steroids or the commercially-available drug, Restasis, within the past 2 weeks as well as tetracycline compounds (tetracycline, doxycycline, and minocycline) within the last month or isotretinoin (Accutane) within the past 6 months. Subjects who report any previous treatment with Anakinra (Kineret®) or any therapeutic agent targeted at IL-1 blockade are similarly excluded. Furthermore, a subject is excluded from the following study if he or she: has a history of Stevens-Johnson syndrome or ocular pemphigoid; has a history of eyelid surgery; has had intra-ocular surgery or ocular laser surgery within 3 months; has a history of microbial keratitis, including herpes; has active ocular allergies; has a corneal epithelial defect >1 $mm^2$; has used topical steroids or Restasis within the past 2 weeks; has experienced any change in dosage of tetracycline compounds (tetracycline, doxycycline, and minocycline) within the last month; has used isotretinoin (Accutane) within the past 6 months; has had any previous treatment with Anakinra (Kineret®) or any therapeutic agent targeted at IL-1 blockade; is a pregnant or lactating woman; has signs of current infection, including fever and current treatment with antibiotics; has liver, renal, or hematologic disease; has a history of cancer; has used any other investigational drug.

Under certain circumstances, subjects are withdrawn from the following study. The following criteria are used to determine when a subject must be removed or permitted to leave the study. Individuals are discontinued early from the study due to the following reasons, including, but not limited to: protocol violations, adverse events, lack of efficacy, pregnancy, and administrative reasons (e.g., inability to continue, lost to follow-up).

Screening Visit

Prospective patients as defined by inclusion/exclusion criteria are considered for entry into this study. The study design and treatment regimen are discussed with each patient. Those wishing to participate are examined for entry into the study with the following exams:

Medical and ophthalmic histories
Patient questionnaire (OSDI) (see Example 1 and FIG. 1)
Best corrected visual acuity (BCVA) (Snellen chart)
Fluorescein tear break-up time (TBUT) (see Example 2)
Cornea and conjunctival staining (see Example 3
Schirmer test without anesthesia (see Example 4)
Schirmer test with anesthesia (see Example 4)
Meibomian gland evaluation (see Example 5)
Biomicroscopy
Intraocular pressure
Fundus examination To avoid the influence of one procedure on another, dry eye tests and ocular surface evaluation are done in the following sequence because the Schirmer test can disrupt tear film stability and cause false-positive ocular surface dye staining: measurement of tear film break-up time (TBUT), ocular surface dye staining pattern (fluorescein and lissamine green staining), Schirmer's test without and with anesthesia, and meibomian gland evaluation (FIG. 6).

After the eye examinations, each patient who qualifies to continue in the study (according to the inclusion/exclusion criteria) is instructed to instill one drop of the randomly assigned masked treatment three times a day in both eyes. The topical solution of 2.5% (25 mg/ml) concentration of Kineret is formulated and prepared from commercially available preservative-free solution of Kineret® (Amgen, Thousand Oaks, Calif.) by the MEEI hospital pharmacy using aseptic technique. For the control group, vehicle [Refresh Liquigel (1% Carboxymethylcellulose)] is used three times a day in both eyes. During the treatment phase, patients are instructed to instill 1 drop of study medication three times a day for 3 months; 1 drop in each eye upon waking in the morning, at noon, and at bedtime.

To reduce the chance of systemic absorption of Kineret, patients are asked to put digital pressure on lacrimal ducts for five minutes. Patients are advised not use artificial tears or other topical medications 30 minutes before or 30 minutes after instilling the study medication to prevent dilution of the study medication. This study does not include blood sampling or any pharmacokinetic measures.

Compliance Visit

Each patient returns for a compliance visit at 2 weeks (Table 2). At this visit, the investigator asks direct questions about patient compliance with the study treatment and adverse events. Patients can be discontinued from the study because of adverse events and protocol violations, but every effort is made to enhance compliance and maintain subjects on the treatment protocol.

Follow-up Visits

To determine the safety and efficacy of topical IL-1Ra for management of posterior blepharitis, 5 follow-up visits (eye exam) are scheduled at day 1, week 2, 6, 12, and 16 (see Table 2). Patients are instructed to strictly follow the study visit schedule. In each follow-up visit, the patient is asked to fill out the OSDI questionnaires (FIG. 1). In addition to a comprehensive eye examination, tear function and ocular surface tests including TBUT, cornea and conjunctival staining tests, meibomian gland evaluation, and Schirmer tests, are performed.

TABLE 2

Schedule of Events and Procedures

| | Visit | | | | | |
|---|---|---|---|---|---|---|
| | 1 | 2 | 3 | 4 | 5 | 6 |
| | Time Period | | | | | |
| | Screening Visit | Day 1 (Safety Visit) | Week 2 (Compliance Visit) | Week 6 | Week 12 | Week 16 |
| Obtain Informed Consent | X | | | | | |
| Inclusion/exclusion criteria | X | | | | | |
| OSDI questionnaire | X | | X | X | X | X |
| Medical & Ophthalmic History | X | | | | | |
| Pregnancy Test | X | | | | | |
| BCVA | X | | X | X | X | X |
| TBUT | X | | X | X | X | X |
| Cornea & Conj. Staining | X | | X | X | X | X |
| Schirmer without Anesthesia | X | | X | X | X | X |
| Schirmer with Anesthesia | X | | X | X | X | X |
| Meibomian Gland Evaluation | X | | X | X | X | X |
| Biomicroscopy | X | X | X | X | X | X |
| Intraocular Pressure | X | | X | X | X | X |
| Funduscopy | X | | X | X | X | X |
| Compliance Check | | X | X | X | X | |
| Adverse Event Query | | X | X | X | X | X |

Concurrent Therapies

Concurrent enrollment in another clinical investigational drug or device study is prohibited. The use of any concurrent medication, prescription or over-the-counter, is recorded along with the reason the medication is taken. During the study, all concomitant medication treatment regimens, ocular hygiene treatments (i.e., lid scrubs and warm compresses), or insertion of punctal plugs are kept as constant as permitted by accepted medical practice.

Using artificial tears is permissible at screening visits and during the study. However, concomitant use of artificial tears is monitored. At each study visit, patients are queried about the average number of times they used artificial tears each day during the past week and the number of days during the past week when they did not use any artificial tears.

Systemic and topical ophthalmic medications that could interfere with the response to study medications or the interpretation of the study results are prohibited during the study. This includes any systemic or topical steroid, cyclosporine, and tetracycline compound.

When necessary for the treatment of patients, administration of a prohibited therapy is done with the safety of the study participant as the primary consideration. The administration of a prohibited medication or procedure is considered a protocol violation and the patient may be discontinued from the study.

During the course of study, if the patient complains of mild to moderate form of ocular surface symptoms, more frequent use of artificial tears (Refresh®) is encouraged without unmasking the patient. If treatment with artificial tears is inadequate, or the patient develops a severe form of ocular surface disease and dry eye, for the safety and proper treatment of the subject, the investigator can unmask the subject's treatment assignment to determine which treatment has been assigned and institute appropriate follow-up care. However, the patient is kept in the study so that an "intention to treat" analysis can be performed.

Efficacy Measures

Several signs of the efficacy of administration of therapeutic compounds of the invention are monitored. The objective signs are meibomian gland secretion quality, meibomian gland occlusion, tear break-up time, corneal and conjunctival staining, and Schirmer test (with and without anesthesia). The subjective endpoints are the OSDI questionnaire score. All these variables are carefully measured at baseline and all visits toward the end of follow up (Table 2).

The following are non-limiting examples of primary efficacy variables: Meibomian gland secretion quality; Tear Break-up time; Cornea and Conjunctival staining score; and the OSDI questionnaire score. Alternatively, or in addition, secondary efficacy variables are used to determine the therapeutic value of administration of compositions of the invention. Nonlimiting examples of secondary efficacy variables include: Meibomian gland occlusion; Schirmer test without anesthesia; Schirmer test with anesthesia. Primary and/or secondary efficacy variables are considered.

In this study, the treatment with topical IL-1Ra is considered efficacious if the 2.5% solution shows a mean change from baseline (0-3 scale) for meibomian gland secretion quality of >1 unit better than vehicle at the week-12 visit. Alternatively, the treatment with topical IL-1Ra is considered efficacious if the 2.5% solution shows a mean change from baseline in average score (0-5 scale) for corneal and conjunctival staining of >1 unit better than vehicle at the week-12 visit.

Safety Measures

The primary safety variable monitored is the occurrence of adverse events. The severity of each adverse event observed (ocular and systemic) is rated from mild (awareness of sign or symptom, but easily tolerated) to severe (incapacitating with inability to work or do usual activity). The relationship of the event to the study medication is assessed by the investigator as none, unlikely, possible, probable, or definite. Safety variables are evaluated at baseline and at all study visits.

At each visit throughout the study, the investigator begins querying for adverse events by asking each patient a general, non-directed question such as "How have you been feeling since the last visit?" Directed questioning and examination is then done as appropriate. The investigator asks questions to subjects at each visit to determine if they have had any changes to the use of concomitant medications since the previous visit. A comprehensive eye examination including best-corrected visual acuity, measuring intraocular pressure, evaluation of the condition of the lid/lashes, conjunctiva, cornea, anterior chamber, iris/pupil, lens, vitreous, macula and optic nerve is performed. Any changes in the study eye from the baseline visit is recorded.

Statistical Procedures

Power and Sample Size Considerations:

TABLE 3

Estimated Prevalence for Anticipated Ordered Categories of Meibomian Quality Scores

| Scenario | | | Meibomian |
| --- | --- | --- | --- |
| High | Moderate | Low | Score |
| 0.20 | 0.28 | 0.40 | 0 |
| 0.28 | 0.32 | 0.28 | 1 |
| 0.32 | 0.25 | 0.20 | 2 |
| 0.20 | 0.20 | 0.12 | 3 |
| Mean (SD) = 1.52 (1.02) | Mean (SD) = 1.32 (1.09) | Mean (SD) = 1.04 (1.04) | |

In order to estimate the power of the study, it is assumed that 50% of the subjects are randomized to topical IL1-Ra and 50% to vehicle. A conservative estimate can then be constructed of study power, according to Sullivan and D'Agostino (Sullivan, L. M. and D'Agostino, R. B. 2003. Stat Med. 22(8):1317-34), using a t-test comparison of the predicted distribution of primary endpoints within ordered categories. Power estimates using this method are conservative because the actual analysis uses data from two eyes while appropriately accounting for their correlation, which has been demonstrated to have greater power as compared to methods based on using the person as the unit of analysis.

The work of Sullivan and D'Agostino indicates that the t-test performs well for the comparison of ordinal scales with 3 to 5 ordinal categories. Estimates of power are based on three scenarios (high, moderate, and low) for the anticipated distribution of scores in the placebo group. As displayed in Table 3 above, a mean score between 1.04 and 1.52 is anticipated, with a standard deviation between 1.02 and 1.09. A clinically meaningful difference is a reduction of 1 in the mean score, or approximately 1 standard deviation.

Based on the two-sample t-test, with Bonferonni adjustment for multiple comparisons (four primary outcome variables) an observer would have ≥80% power to detect a mean difference of 1 standard deviation for sample sizes of 28, 30, and 28, per group, under the high, moderate, and low scenarios, respectively. As noted, actual power would be enhanced through use of scores from both eyes of study participants, with consideration of the correlation between fellow eyes in the analysis. Therefore, the sample size of N=30 per group was chosen.

Statistical Analysis:

For efficacy variables and any other variables except for safety, all subjects are analyzed with the treatment to which they were randomized (the intent-to-treat population). For safety variables, subjects are analyzed with the treatment actually received (the safety population).

The primary analysis for the proposed study is based on a standard intention-to-treat analysis with each study participant analyzed with respect to the randomized treatment assignment, regardless of eventual compliance. A secondary analysis may include imputation of missing data for select variables. A per-protocol analysis, disqualifying patients or patient visits, might also be done, but is not planned because observational analyses of actual treatment use could introduce bias if the pattern of use is in some way related to the outcome.

Despite the randomized nature of the treatment assignments, in this relatively small sample of study subjects there may be imbalances with regard to potential confounding variables. Thus, as an initial step in the analysis, those assigned to active treatment versus those randomized to vehicle are compared with regard to demographic characteristics and potential confounding variables, using the nonparametric Wilcoxon rank sum test for continuous or ordinal variables, and chi-square or Fisher's exact tests for categorical variables.

To assess the effect of topical IL-1Ra treatment, the distribution of a) meibomian gland secretion score, and b) corneal and conjunctival staining scores between patients assigned to topical IL-1Ra and those assigned to vehicle are compared using the stratified Wilcoxon rank sum test with variance correction for clustering effects as recently developed by Rosner and Glynn (Rosner, et al. 2003. Biometrics. 59(4): 1089-98). Based on simulation studies, analyses of opthalmologic data that use the information from two eyes and appropriately account for their correlation have greater power than methods based on a single eye or the average of the two eyes (Rosner, et al. 2003. Biometrics. 59(4): 1089-98; Glynn, R. J. and Rosner, B. 1994. Stat Med. 13(10): 1023-36). This method uses large sample theory to incorporate clustering effects to ordinal outcomes such as the clinical scoring scales used here. It can be implemented with standard software (e.g. SAS PROC RANK), and provides a valid test for either balanced or unbalanced clustered data in the presence or absence of tied rankings in datasets in which there are ≥20 clusters per group. The test may be used in place of the cluster-mean procedure (e.g. as would result from analysis using SAS PROC MIXED), and provides unbiased p-values where the standard Wilcoxon test is inappropriate. These analyses are then extended to control for potential confounding by variables using the stratified version of the test. A logical cut-point for stratification of continuous variables would be the median level among the vehicle treated group.

Prior to the development of these methods, studies have generally used the person as the unit of analysis, using either a composite score or data from one eye per subject. However, information is potentially lost by collapsing eye-specific grades into a single person-specific grade.

In secondary analyses, the effect of topical IL-1Ra on other outcomes such as the OSDI score and tear break up time is also explored. Similarly, these analyses use the stratified Wilcoxon test with variance correction.

In general, a two-sided test with p-value less than or equal to 0.0125 is considered statistically significant. This level of significance was arrived at by dividing the overall type 1 error rate of 0.05 by 4, which is the number of comparisons in the primary analysis.

Although patients are evaluated at multiple time points throughout the study, the primary endpoint is on the last observation while on treatment during the 3-month study period.

Example 9: Effect of IL-1Ra on Intraocular Pressure (IOP)

IL-1Ra was administered to one eye of wild type BALB/c mice and the mean intraocular pressure (IOP) of the both the treated and the non-treated (contralateral eye) were measured. Data from these experiments show that administration of IL-1Ra is sufficient to reduce IOP by a statistically significant amount over the course of one day, and particularly, over the duration of one night (Table 4, below, and FIG. 3). IOP is a risk factor for the development of glaucoma. Importantly, the compositions and methods used were effective on wild type, or normal, subjects. As such, this example is proof-of-concept that the compositions and methods of the invention are effective for treating elevated intraocular pressure or ocular hypertension that has been caused by a variety of mechanisms, including, but not limited to IL-1-mediated inflammation.

TABLE 4

Effect of one drop of topical IL-1Ra (2.5%) on Intraocular pressure (IOP) during the Day (after 6 hours) and Overnight (after 12 hours) in BALB/c mice.

|  | N | Contralateral Eye | Treated Eye | Difference (Contralateral Eye − Treated Eye) | % Reduction | P value |
| --- | --- | --- | --- | --- | --- | --- |
| Day (after 6 h) | 5 | 9.1 ± 0.46 | 8.0 ± 0.27 | 1.1 ± 0.51 | 11.5 ± 0.05 | 0.095 |
| Overnight (After 12 h) | 5 | 13.7 ± 0.90 | 10.3 ± 0.75 | 3.4 ± 0.38 | 24.7 ± 0.02 | 0.0009 |

Data are expressed as the mean IOP (mm Hg) ± SEM. P value is for treated eye versus the contralateral eye (paired t-test).

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for inhibiting or reducing dry eye disease in a subject characterized as suffering from dry eye disease, comprising locally administering to an ocular tissue or an ocular adnexal tissue of the subject a composition that inhibits the binding of an inflammatory interleukin-1 (IL-1) cytokine to an IL-1 receptor, wherein said composition consists of a pharmaceutical carrier and a polypeptide consisting of the amino acid sequence of SEQ ID NO: 16; wherein the subject characterized as suffering from dry eye disease is identified by detection of a sign or symptom selected from the group consisting of epithelial overexpression of an inflammatory cytokine, vascular hyperplasia or thickening of eyelid margin, neovascularization of eyelid margin or corneal periphery, increase of leukocytes at an ocular surface, or overexpression of a matrix metalloprotease at an ocular surface; and wherein said method inhibits or reduces the severity of at least one of said signs or symptoms.

2. The method of claim 1, wherein said dry eye disease comprises infectious blepharitis.

3. The method of claim 1, wherein said dry eye disease comprises non-infectious blepharitis.

4. The method of claim 1, wherein said method does not comprise administration of an antibiotic compound.

5. The method of claim, 1 wherein said composition is present in a concentration of 0.1-10% (mg/ml).

6. The method of claim 1, wherein the form of said composition is in a form of a solid, a paste, an ointment, a gel, a liquid, an aerosol, a mist, a polymer, a film, an emulsion, or a suspension.

7. The method of claim 1, wherein said composition is administered topically.

8. The method of claim 1, wherein said method does not comprise systemic administration or substantial dissemination to non-ocular tissue.

9. The method of claim 1, wherein said pharmaceutical carrier is selected from the group consisting of a physiological acceptable salt, poloxamer analogs with carbopol, carbopol/HPMC, carbopol-methyl cellulose, carboxymethylcellulose (CMC), hyaluronic acid, cyclodextrin, and petroleum.

10. The method of claim 1, wherein said dry eye disease is associated with posterior blepharitis or meibomian gland dysfunction.

11. The method of claim 1, wherein said dry eye disease comprises aqueous deficiency dry eye or evaporative dry eye.

12. The method of claim 1, wherein said pharmaceutical carrier is an aqueous carrier.

* * * * *

UNITED STATES PATENT AND TRADEMARK OFFICE
CERTIFICATE OF CORRECTION

PATENT NO. : 10,105,441 B2
APPLICATION NO. : 12/298380
DATED : October 23, 2018
INVENTOR(S) : Reza Dana et al.

Page 1 of 1

It is certified that error appears in the above-identified patent and that said Letters Patent is hereby corrected as shown below:

In the Claims

At Column 142, Claim 6, Line number 43, after "wherein", delete "the form of".

Signed and Sealed this
Twenty-second Day of January, 2019

Andrei Iancu
*Director of the United States Patent and Trademark Office*